(12) United States Patent
Yim et al.

(10) Patent No.: US 11,434,217 B2
(45) Date of Patent: Sep. 6, 2022

(54) METHOD FOR SYNTHESIS OF LOBARIC ACID AND ANALOG THEREOF

(71) Applicant: KOREA INSTITUTE OF OCEAN SCIENCE & TECHNOLOGY, Busan (KR)

(72) Inventors: Joung Han Yim, Gyeonggi-do (KR); Il-Chan Kim, Gyeonggi-do (KR); Se Jong Han, Gyeonggi-do (KR); Ui Joung Youn, Incheon (KR); Hong Kum Lee, Gyeonggi-do (KR); Jun Hyuck Lee, Incheon (KR); Tai Kyoung Kim, Incheon (KR); Kwon Joo Yeo, Chungcheongbuk-do (KR)

(73) Assignee: KOREA INSTITUTE OF OCEAN SCIENCE AND TECHNOLOGY, Busan (KR)

( * ) Notice: Subject to any disclaimer, the term of this patent is extended or adjusted under 35 U.S.C. 154(b) by 191 days.

(21) Appl. No.: 16/958,794

(22) PCT Filed: Jul. 23, 2018

(86) PCT No.: PCT/KR2018/008254
§ 371 (c)(1),
(2) Date: Mar. 27, 2021

(87) PCT Pub. No.: WO2019/132148
PCT Pub. Date: Jul. 4, 2019

(65) Prior Publication Data
US 2021/0246112 A1 Aug. 12, 2021

(30) Foreign Application Priority Data
Dec. 29, 2017 (KR) .................. 10-2017-0183674

(51) Int. Cl.
*C07D 307/88* (2006.01)
(52) U.S. Cl.
CPC .................. *C07D 307/88* (2013.01)
(58) Field of Classification Search
CPC .................................. C07D 307/88
See application file for complete search history.

(56) References Cited

U.S. PATENT DOCUMENTS

2014/0073614 A1  3/2014 Yim et al.

FOREIGN PATENT DOCUMENTS

| KR | 10-2012-0036026 | * | 4/2012 |
| KR | 1020120036025 A | | 4/2012 |
| KR | 1020120036026 A | | 4/2012 |
| KR | 1020120121274 A | | 11/2012 |
| KR | 10-2014-0052396 | * | 5/2014 |
| KR | 1020140052396 A | | 5/2014 |

OTHER PUBLICATIONS

Bhattarai, H., et al., "A New Pseudodepsidone from the Antarctic Lichen Stereocaulon Alpinum and its Antioxidant, Antibacterial Activity", "The Journal of Antibiotics", pp. 559-561, vol. 66.
Huneck, S., "The Significance of Lichens and Their Metabolites", "Naturwissenschaften", 1999, pp. 559-570, vol. 86.
Ingolfsdottir, K., "Molecules of Interest: Usnic acid", "Phytochemistry", 2002, pp. 729-736, vol. 61.
Kumar, S., et al., "Lichen Metabolites. 1. Inhibitory Action Against Leukotriene B4 Biosynthesis by a Non-Redox Mechanism", "J. Nat. Prod.", Jun. 1999, pp. 817-820, vol. 62.
Morita, H., et al., "Antimitotic Activity of Lobaric Acid and a New Benzofuran, Sakisacaulon A From Stereocaulon Sasakii", "Bioorganic and Medicinal Chemistry Letters", 2009, pp. 3679-3681, vol. 19.
Oksanen, I., "Ecological and Biotechnological Aspects of Lichens", "Appl. Microbiol Biotechnol", 2006, pp. 723-734, vol. 73.
Seo, C., et al., "Protein tyrosine phosphatase 1B inhibitory effects of depsidone and pseudodepsidone metabolites from the Antarctic . . . ", "Bioorganic & Medicinal Chemistry Letters", Mar. 26, 2009, pp. 2801-2803, vol. 19.
Ismed, F., et al., "Lobarin from the Sumatran lichen, Stereocaulon halei", Fitoterapia, 2012, pp. 1693-1698, vol. 83, Publisher: Elsevier.
Kim, T.K., et al., "Total Synthesis of Lobaric Acid and Its Derivatives from the Antarctic Lichen Stereocaulon alpinum", Journal of Natural Products, 2018, pp. 1460-1467, vol. 81, Publisher: ACS Publications.

* cited by examiner

*Primary Examiner* — D Margaret M Seaman
(74) *Attorney, Agent, or Firm* — Hultquist, PLLC; Steven J. Hultquist

(57) ABSTRACT

The present invention can synthesize lobaric acid and four analogues thereof, which are five phenolic lichen metabolites isolated from an extract of the Antarctic lichen *Stereocaulon alpinum* and selectively inhibit PTP1B, by a simple, economic and efficient chemical synthesis method.

6 Claims, 43 Drawing Sheets

METHOD FOR SYNTHESIS OF LOBARIC ACID AND ANALOG THEREOF

CROSS-REFERENCE TO RELATED APPLICATIONS

This application is a U.S. national phase under the provisions of 35 U.S.C. § 371 of International Patent Application No. PCT/KR2018/008254 filed Jul. 23, 2018, which in turn claims priority under 35 U.S.C. § 119 of Korean Patent Application No. 10-2017-0183674 filed Dec. 29, 2017. The disclosures of such International Patent Application No. PCT/KR2018/008254 and Korean Patent Application No. 10-2017-0183674 are hereby incorporated herein by reference in their respective entireties, for all purposes.

TECHNICAL FIELD

The present invention relates to methods for synthesis of lobaric acid and analogues thereof, and more particularly, to methods of synthesizing lobaric acid and analogues thereof, which exhibit the effect of selectively inhibiting PTP1B, in a simple, economic and efficient manner.

BACKGROUND ART

Lichens are known to produce unique secondary metabolites different from those of higher plants (Ingolfsdottir, K., Phytochemistry, 61:729, 2002). Secondary metabolites produced by lichens are mostly depsides, depsidones and dibenzofurans, and these compounds are considered associated with the low growth rate of lichens (Kumar, K. C. S. et al., *J. Nat. Prod.*, 62:817, 1999; Huneck, S., Naturwissenschaften, 86:559, 1999). In addition, various biological activities of lichen metabolites, including antibiotic, antimycobacterial, antiviral, analgesic and antipyretic properties, have been indicated by screening processes (Ingolfsdottir, K., Phytochemistry, 61:729, 2002; Kumar, K. C. S. et al., *J. Nat. Prod.*, 62:817, 1999). Thus, interest has grown in the development of medicines using lichen metabolites.

In recent years, it has been reported that metabolites extracted from Antarctic lichens have a variety of biological activities such as antibiotic, antimycobacterial, antiviral, anti-inflammatory, anti-allergic, antipyretic, anti-proliferative and cytotoxic effects (Oksanen I, Appl Microbiol Biotechnol 2006; 73:723-34). In addition, these metabolites are widely used in the fields of natural cosmetics and medicines, and are known to have few side effects compared to industrial products. However, adequate information regarding the health-promoting properties of bioactive substances in lichens and similar species having pharmaceutical potential is not available.

In 2009, the Korea Polar Research Institute extracted five phenolic lichen metabolites from the lichen *Stereocaulon alpinum*, identified the structures of the metabolites, and then confirmed that these metabolites acted selectively on PTP1B, a member of the protein tyrosine phosphatase family, and exhibited antidiabetic effects when administered to disease model animals. In addition, it was found that the $IC_{50}$ value of lobaric acid as a major metabolite was 0.87 μM. Of these metabolites, three metabolites, lobarin, lobastin and sodium lobarate, are disclosed in Korean Patent Nos. 10-1481140, 10-1481141 and 10-145162.

Accordingly, the present inventors have made extensive efforts to economically and efficiently synthesize lobaric acid and analogues thereof (lobastin, lobastin, methyllobarin and sakisacaulon A), which are five phenolic lichen metabolites that selectively inhibit PTP1B, and as a result, have found that the five phenolic lichen metabolites can be synthesized economically with high yield by simple chemical synthesis methods, thereby completing the present invention.

SUMMARY OF THE INVENTION

It is an object of the present invention to provide a method of synthesizing lobaric acid and lobaric acid analogues (lobastin, lobastin, methyllobarin and sakisacaulon A), which selectively inhibit PTP1B, in an economic and efficient manner.

To achieve the above object, the present invention provides a method of preparing a lobaric acid analogue of Formula 3 or 5, the method comprising a step of subjecting a compound of Formula 10 to a coupling reaction with a compound of Formula 16 or 21, followed by a deprotection reaction:

[Formula 10]

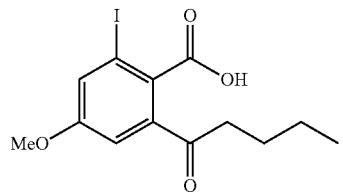

[Formula 16]

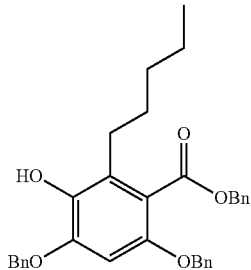

[Formula 21]

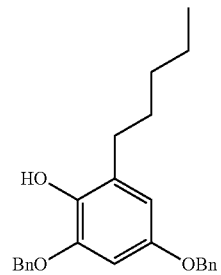

[Formula 3]

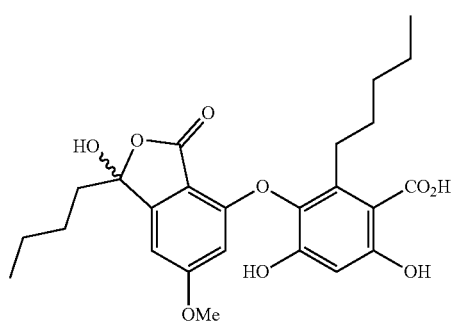

[Formula 5]

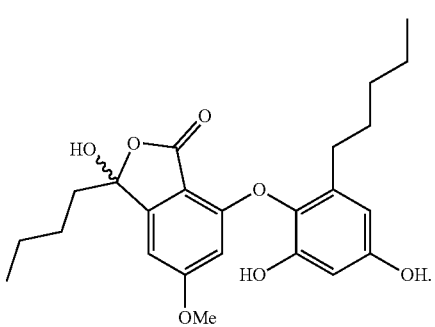

The present invention also provides a method of preparing lobaric acid, the method comprising protecting the carboxylic acid of a lobaric acid analogue of Formula 3 to obtain a compound of Formula 23, and relactonizing the compound of Formula 23 to obtain a lobaric acid of Formula 1:

[Formula 1]

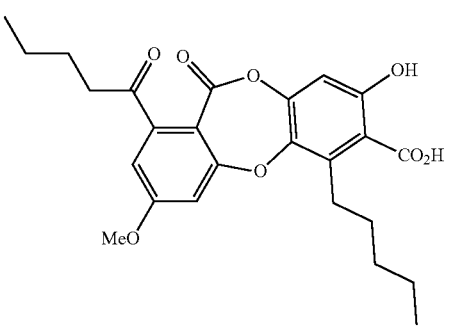

[Formula 23]

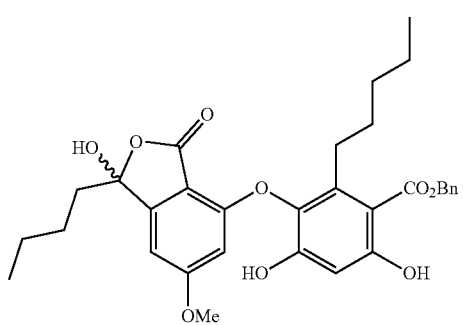

[Formula 3]

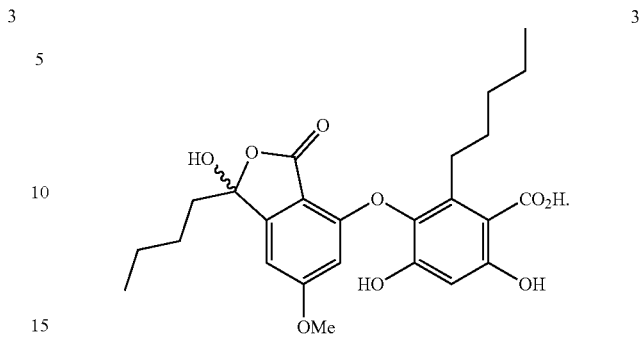

The present invention also provides a method of preparing a lobaric acid analogue, the method comprising reacting a lobaric acid of the following Formula 1 with a strongly nucleophilic strong base or a weakly nucleophilic strong base to obtain the lobaric acid analogue:

[Formula 1]

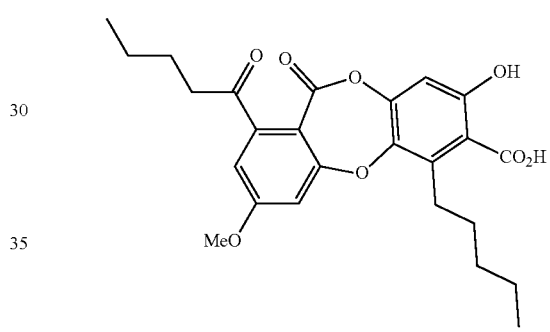

DETAILED DESCRIPTION AND PREFERRED EMBODIMENTS OF THE INVENTION

Figure 1:
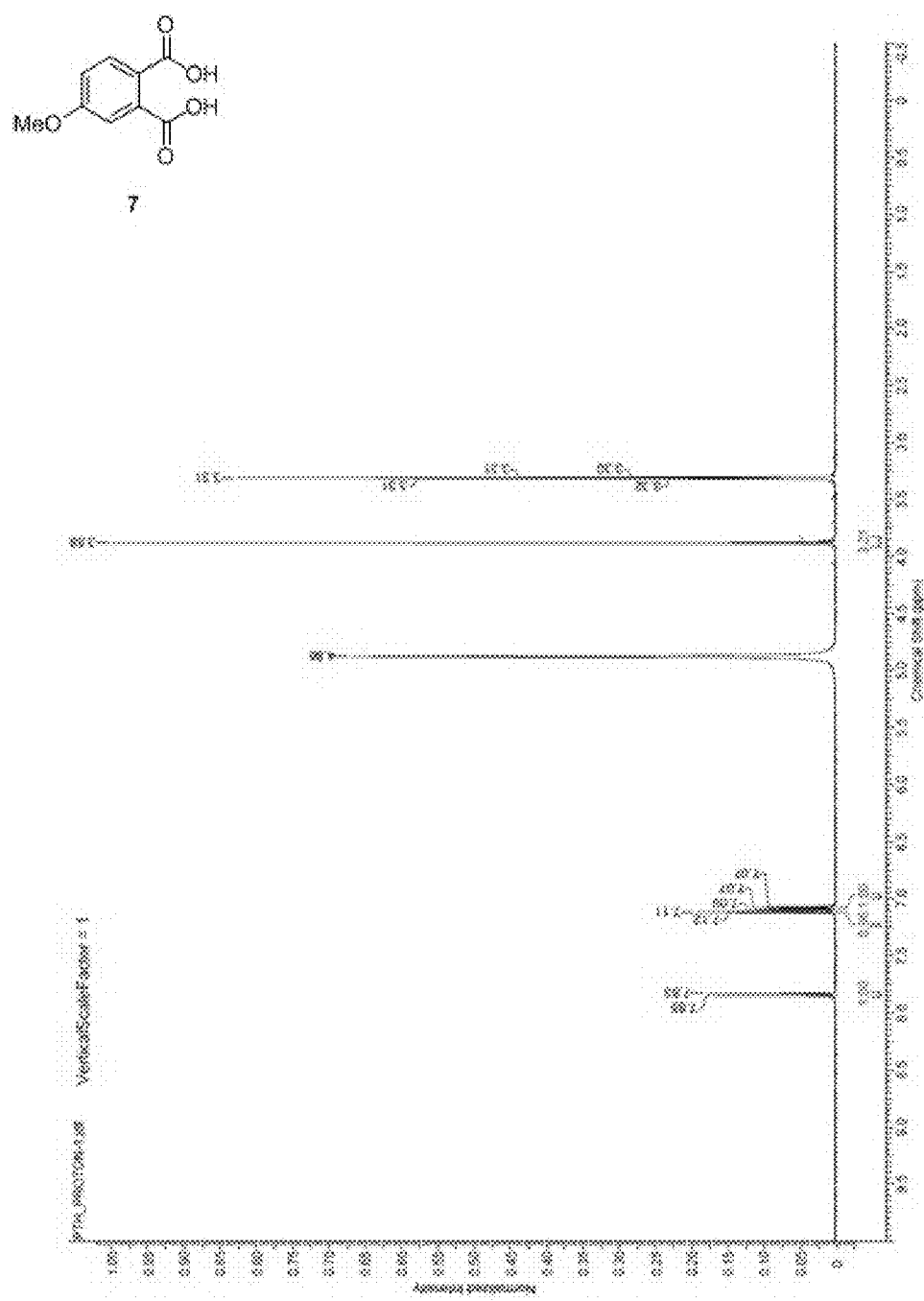
FIG. 1 is the 400 MHz $^1$H-NMR spectrum (in $CD_3OD$) of a compound of Formula 7 according to one example of the present invention.

Unless otherwise defined, all technical and scientific terms used in the present specification have the same meanings as commonly understood by those skilled in the art to which the present disclosure pertains. In general, the nomenclature used in the present specification is well known and commonly used in the art.

The present invention provides methods for simple synthesis of compounds that selectively inhibit PTP1B, in which the compounds are five phenolic lichen metabolites isolated from an extract of the Antarctic lichen *Stereocaulon alpinum*.

According to the present invention, it is possible to obtain five analogues (pseudodepsidone analogue compounds) from lobaric acid by human serum plasma culture. Four major compounds have PTP1B inhibitory activity, and lobaric acid and four analogues thereof may be synthesized by similar synthesis methods. The lobaric acid depsidone structure is flexible and reversible.

[Reaction Scheme 1]

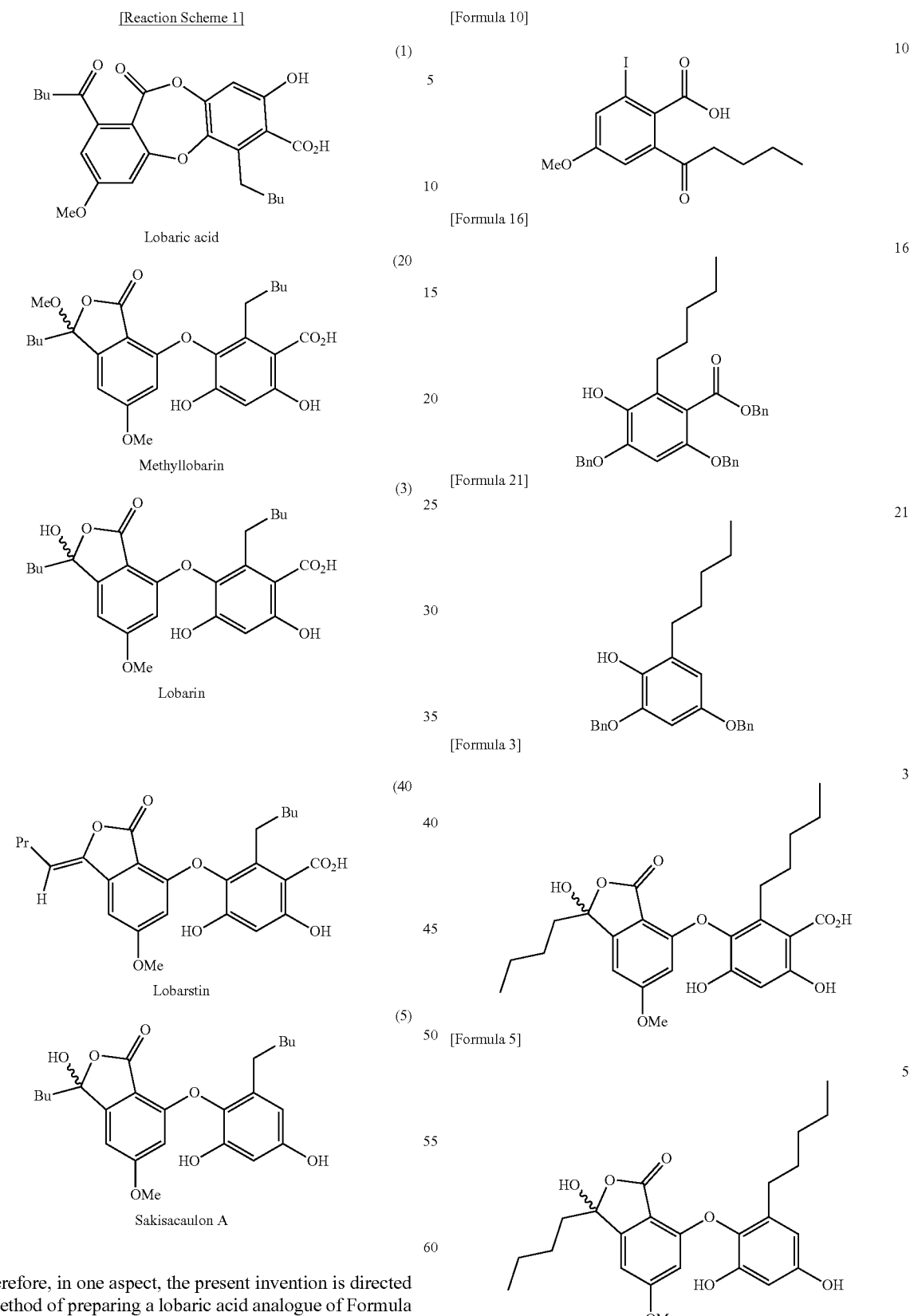

Therefore, in one aspect, the present invention is directed to a method of preparing a lobaric acid analogue of Formula 3 or 5, the method comprising a step of subjecting a compound of Formula 10 to a coupling reaction with a compound of Formula 16 or 21, followed by a deprotection reaction:

In the present invention, the compound of Formula 10 may be produced by a method comprising steps of: (a)

subjecting 4-halogen phthalic anhydride to Ullmann coupling and ring-opening reactions by addition of a metal methoxide, such as sodium methoxide (NaOMe), to obtain 4-methoxy-phthalic acid of Formula 7; (b) reacting the obtained compound of Formula 7 with acetic anhydride to obtain a compound of Formula 8; (c) subjecting the methyl ester moiety of the obtained compound of Formula 8 to Grignard reaction in a solvent, such as THF or ethyl ester, to obtain a compound of Formula 9; and (d) subjecting the obtained compound of Formula 9 to ortho-iodination by addition of an iodoacetate cation-containing compound to obtain the compound of Formula 10:

[Formula 7]

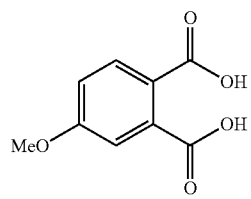

7

[Formula 8]

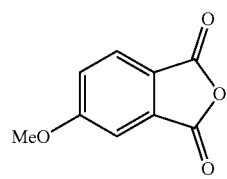

8

[Formula 9]

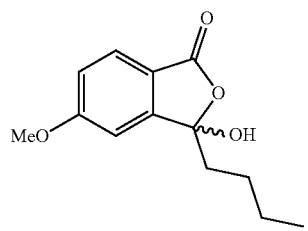

9

[Formula 10]

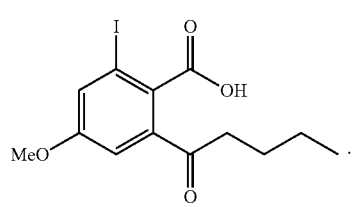

10 obtain a compound of Formula 14; (c) formylating the compound of Formula 14 with a phosphorus oxychloride compound in DMF as a solvent to obtain an aldehyde compound of Formula 15; and (d) reacting the compound of Formula 15 with chloroperoxybenzoic acid in a solvent, such as methylene chloride (MC) or ethylene dichloride (EDC), to obtain the compound of Formula 16:

[Formula 13]

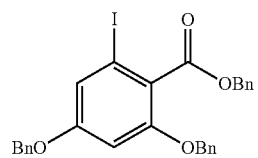

13

[Formula 14]

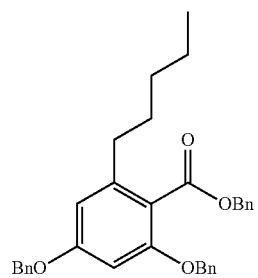

14

[Formula 15]

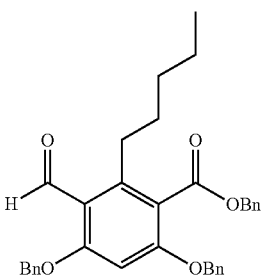

15

[Formula 16]

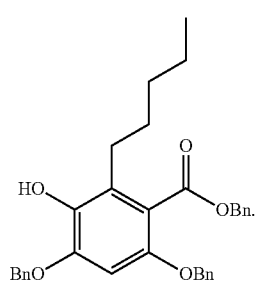

16

In the present invention, the compound of Formula 16 may be produced by a method comprising steps of: (a) protecting the dihydroxy group and carboxylic acid functional group of 2,4-dihydroxybenzoic acid, and then subjecting the 2,4-dihydroxybenzoic acid to ortho-iodination by addition of an iodoacetate cation-containing compound to obtain a compound of Formula 13; (b) alkylating the compound of Formula 13 by addition of pentylboronic acid to In the present invention, the compound of Formula 21 may be produced by a method comprising steps of: (a)

formylating an olivetol compound of Formula 17 with a phosphorus oxychloride compound in dimethylformamide (DMF) as a solvent to obtain a compound of Formula 18; (b) oxidizing the aldehyde of the compound of Formula 18 in a solvent to obtain a compound of Formula 19; (c) protecting the dihydroxy group and carboxylic acid functional group of the compound of Formula 19 with benzyl bromide to obtain a compound of Formula 14; (d) protecting the dihydroxy group of benzoic acid of the olivetol compound of Formula 17 in a solvent, followed by formylation with a phosphorus oxychloride compound to obtain a compound of Formula 20; and (e) reacting the compound of Formula 20 with chloroperoxybenzoic acid in a solvent, such as MC or EDC, to obtain the alcohol compound of Formula 21:

[Formula 17]

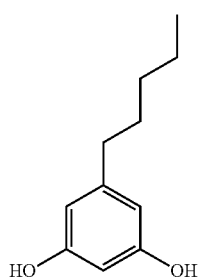

[Formula 18]

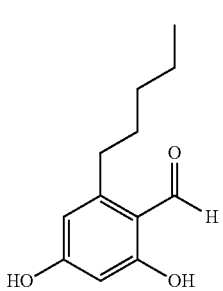

[Formula 19]

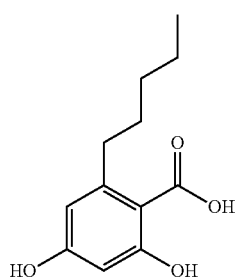

[Formula 14]

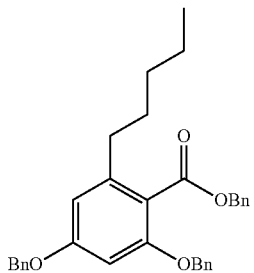

[Formula 20]

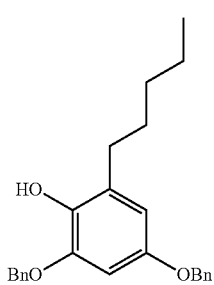

[Formula 21]

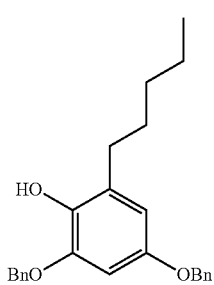

Reaction Scheme 2 below shows a reaction based on retrosynthesis. As shown therein, lobaric acid (Formula 1) may be obtained by reacting an A-ring part with a B-ring part. The major step of synthesis of the A-ring is a C—H activated iodination reaction at the ortho position of benzoic acid. The alkyl chain of the B ring may be extended by Suzuki coupling reaction. Arylether-type lobarin having the A and B rings coupled together may be produced by Ullmann aryl ether coupling reaction. Finally, a 7-membered lactone ring is produced by esterification.

[Reaction Scheme 2]

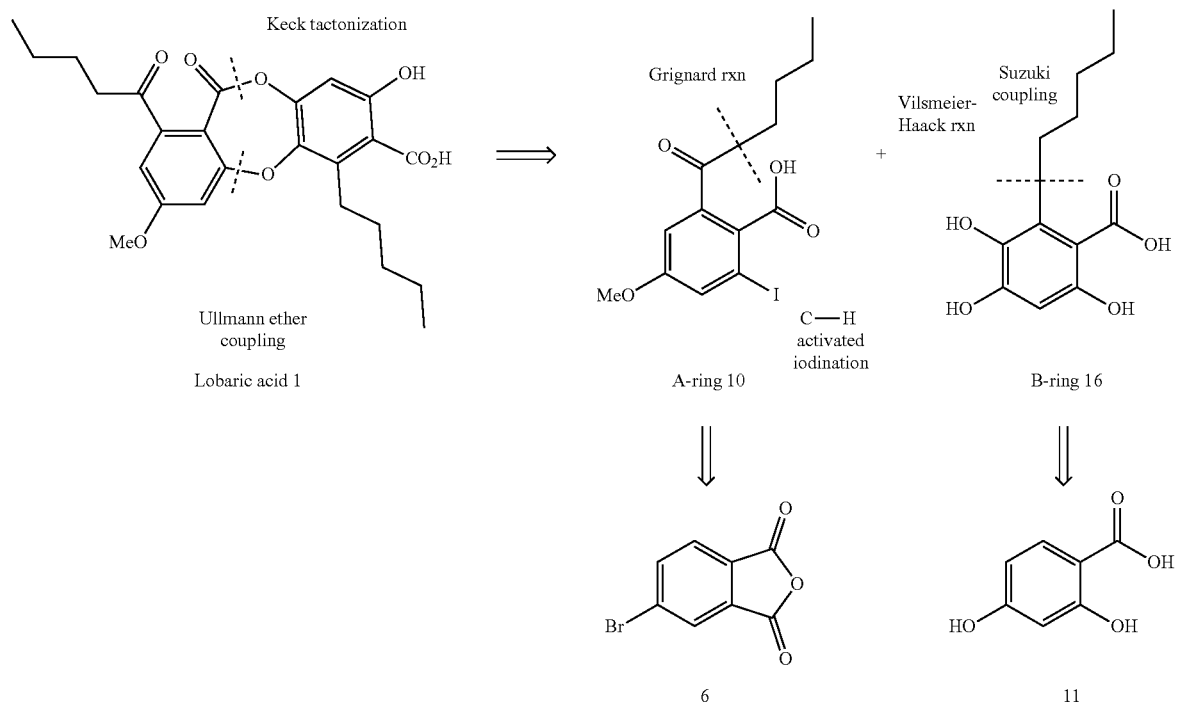

Synthesis of lobaric acid (1) starts with the production of the A-ring (Reaction Scheme 3). The starting material is 4-bromo phthalic anhydride. 4-methoxy-phthalic acid (7) is obtained from the phthalic anhydride by Ullmann coupling with sodium methoxide and ring-opening with an excess of sodium methoxide. 4-methoxy-phthalic anhydride (8) is obtained from the 4-methoxy-phthalic acid by reaction with acetic anhydride under heating and reflux in an anhydrous THF solution. Compound (9) is produced by the Grignard reaction of the methyl ester moiety in a THF solution at room temperature. Counter cation iodoacetate can aid in the C—H activated ortho iodination reaction. A-ring (10) is obtained by heating compound (9) together with palladium, iodine and the counter cation IPh(OAc)$_2$ in a DMF solution at 60° C.

[Reaction Scheme 3] Synthesis of Ring-A

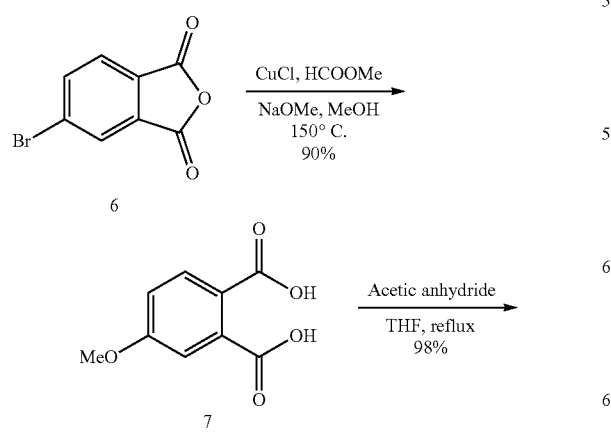

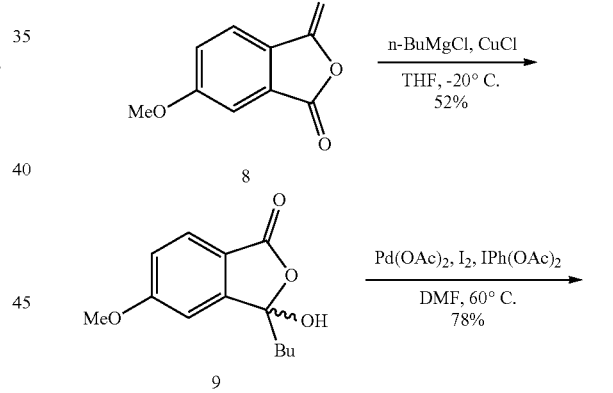

A starting material for synthesis of B-ring which is another part is 2,4-dihydroxybenzoic acid (Reaction Scheme 4). Compound (12) may be obtained in an approximate yield by protecting the dihydroxy group and carboxylic acid moiety of the starting material with a benzyl group. Thereafter, ortho iodination of compound (12) may be performed in a manner similar to iodination of the A-ring to obtain compound (13). According to a modification of a known method, compound (13) is alkylated with pentylboronic acid by Suzuki reaction to obtain compound (14). Compound (14) is subjected to regioselective Vilsmeier-Haack formylation in DMF to obtain aldehyde compound (15). Aldehyde (15) is reacted with m-chloroperoxybenzoic acid (mCPBA) in MC to obtain alcohol compound (16). Compound (16) may be synthesized using olivetol as a starting material. Compound 16 is subjected to Vilsmeier-Haack reaction with POC13 in DMF as a solvent to obtain 2,4-dihydroxy-6-pentylbenzaldehyde (18). The aldehyde is oxidized with carboxylic acid to obtain the compound 2,4-dihydrozyl-6-pentylbenzoic acid (19). The two hydroxyl groups and the benzoic acid are protected with a benzyl group to obtain compound (14). A subsequent process is performed in the same manner to obtain compound 16.

A starting material for synthesis of dicarboxylic acid-type B ring-2 is olivetol. Compound (18) is obtained by performing a formylation reaction in the same manner as described above with synthesis of the B-ring. Protection of the dicarboxyl group is performed using benzyl bromide and potassium carbonate in a DMF solvent. Next, B-ring 2 product (21) is produced through hydroxylation.

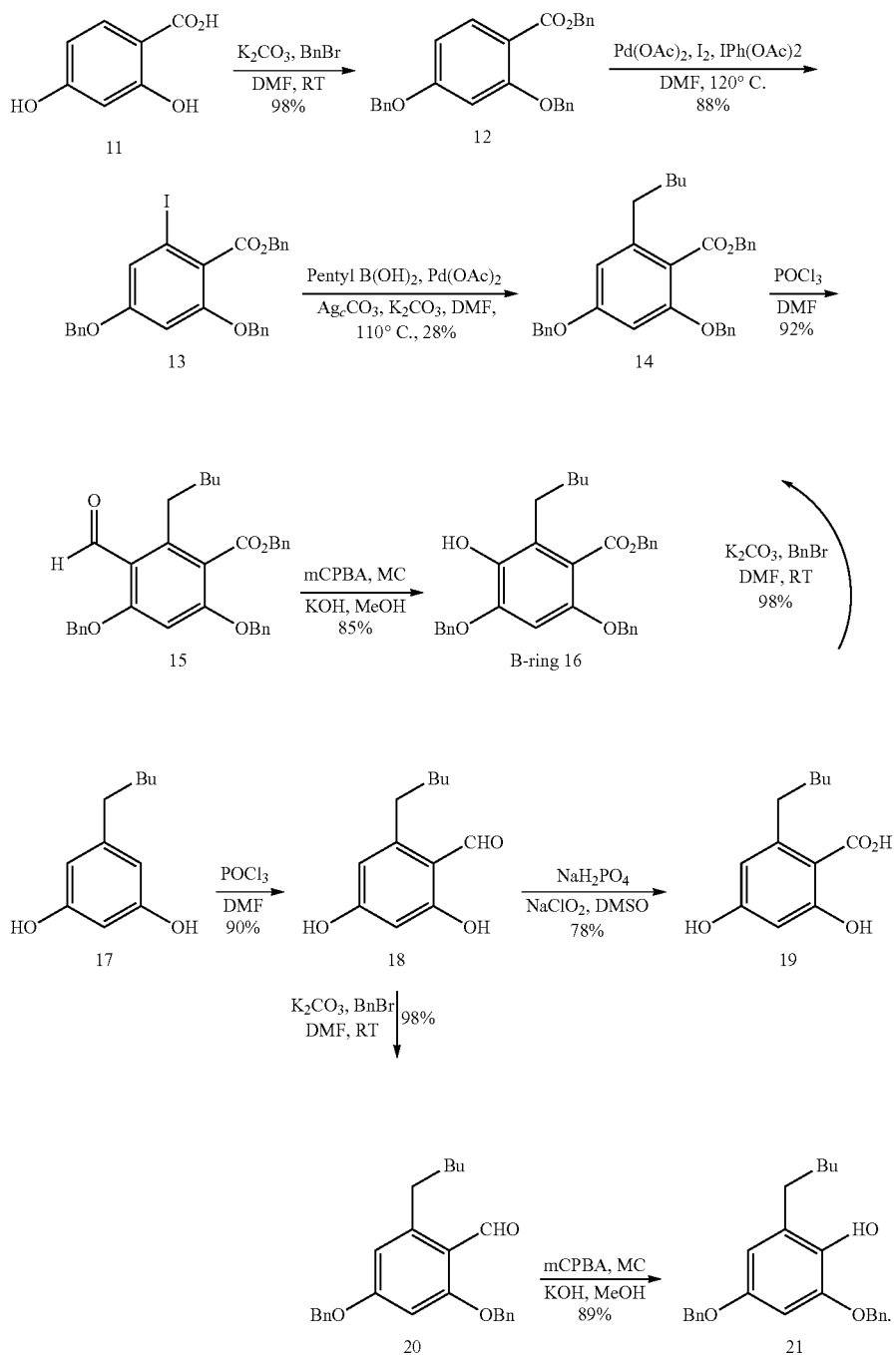

[Reaction Scheme 4] Synthesis of B-ring and B rings-2

For diaryl ether coupling, the A-ring and the B-ring are subjected to Ullmann coupling reaction under heating in DMSO/K₃PO₄ using copper as a catalyst and picolinic acid as a ligand. A 5-membered lactone ring is produced under high-temperature reaction conditions. After the coupling reaction, the benzyl protecting group of product (22) is deprotected using Pd/C and H₂ gas.

[Reaction Scheme 5] Coupling of A-ring and B-ring and deprotection reaction

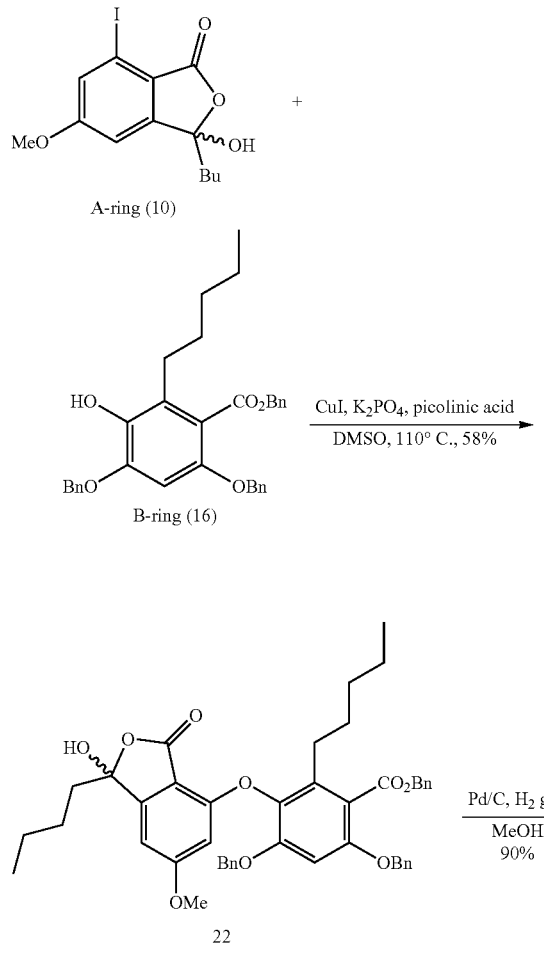

[Reaction Scheme 6]

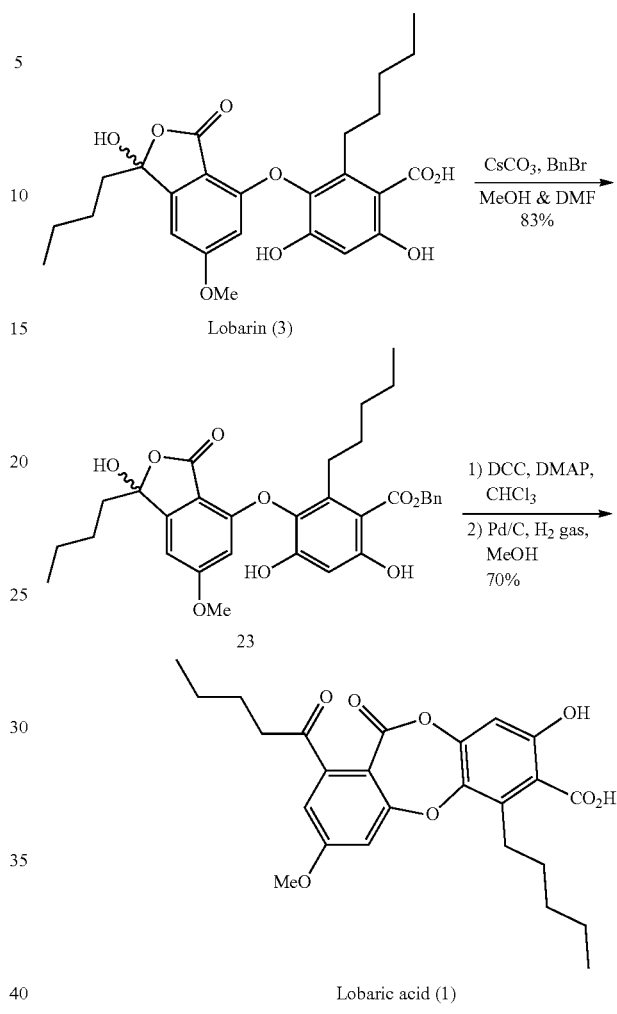

Lobarin (3) may be converted into lobaric acid by protection of the carboxyl group, followed by a 7-membered ring relactonization reaction.

Therefore, in another aspect, the present invention is directed to a method of preparing lobaric acid, the method comprising subjecting a lobaric acid analogue of Formula 3 to a relactonization reaction in a solvent to obtain a lobaric acid of Formula 1:

[Formula 1]

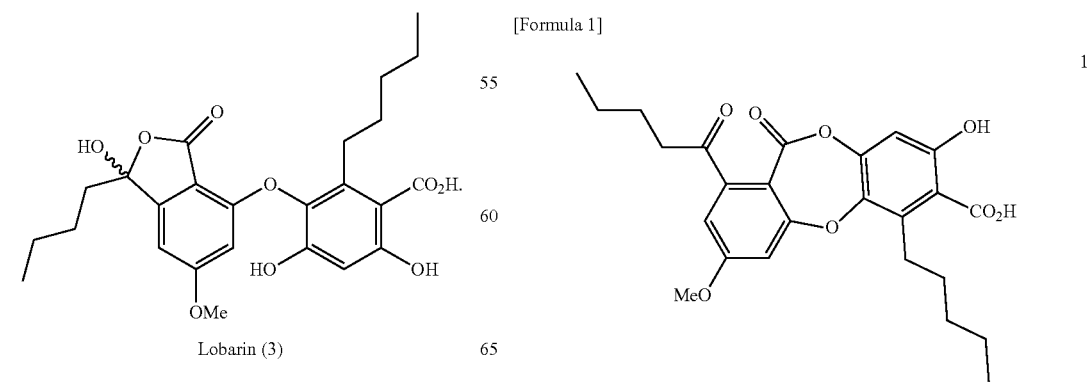

-continued

[Formula 3]

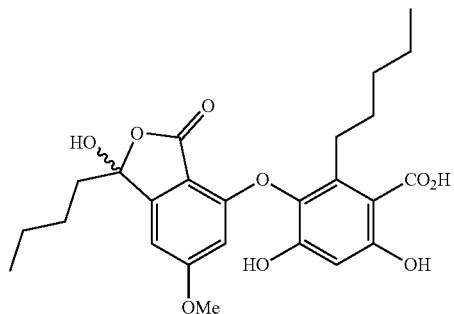

3

[Formula 23]

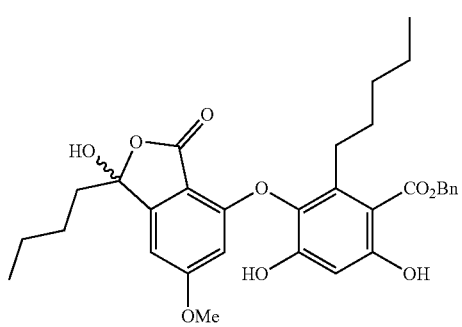

23

[Formula 1]

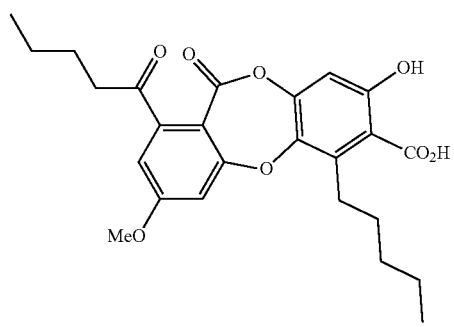

1

In still another aspect, the present invention is also directed to a method of preparing a lobaric acid analogue, the method comprising reacting a lobaric acid of the following Formula 1 with a strongly nucleophilic strong base or a weakly nucleophilic strong base to obtain the lobaric acid analogue:

In the present invention, when a strongly nucleophilic strong base such as sodium hydroxide or sodium methoxide is used, a methyllobarin of the following Formula 2 or a lobarin of the following Formula 3 may be produced:

[Formula 2]

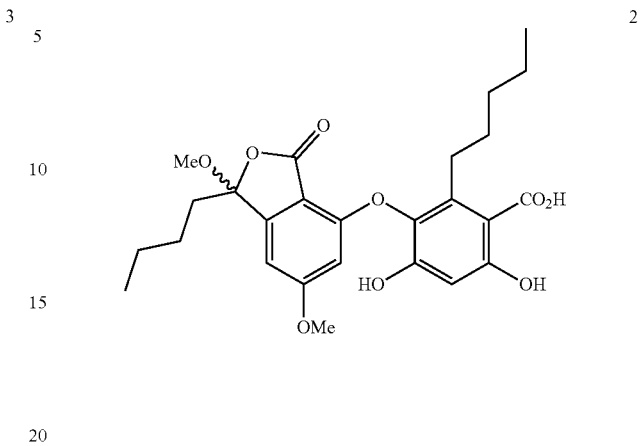

2

[Formula 3]

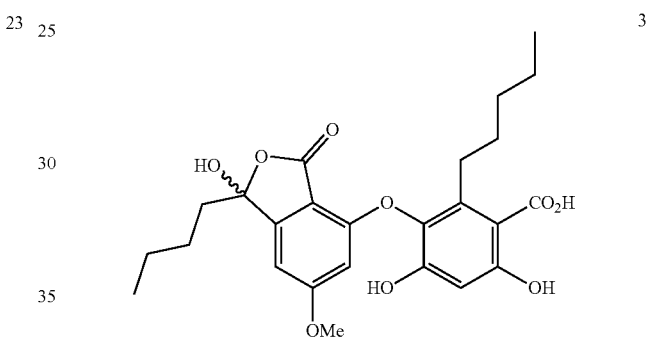

3

In the present invention, when a weakly nucleophilic strong base such as sodium hexamethyldisilazane is used, a lobastin of the following Formula 6 may be produced:

[Formula 6]

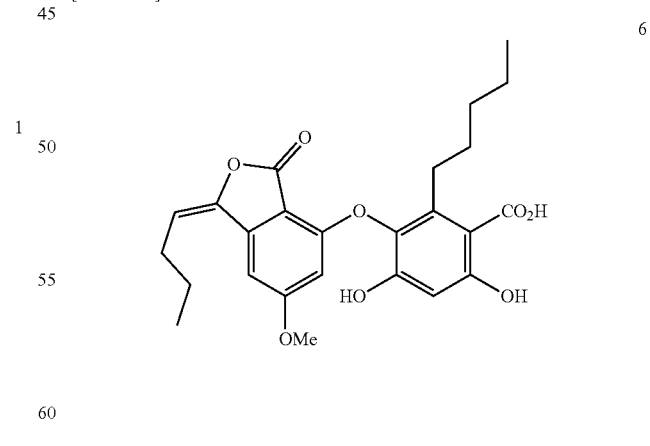

6

In the present invention, a reaction scheme for synthesis of a lobaric acid analogue from lobaric acid is as follows.

[Reaction Scheme 7]

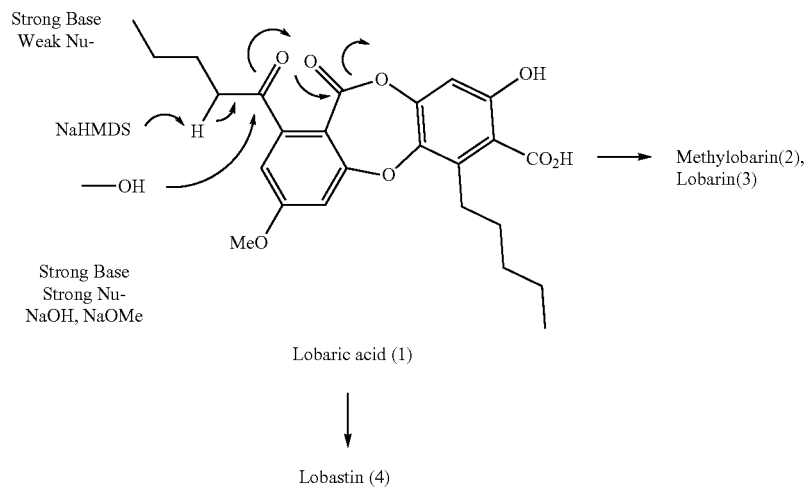

Various derivatives may be produced from the lobaric acid depsidone structure. Strongly basic and highly nucleophilic sodium hydroxide attacks ketone, and a tandem reaction with depsidone ester produces five-membered or 7-membered ring opened lobarin (3). In addition, the very weakly nucleophilic strong base NaHMDS may remove α-protons, and lobastin can be obtained by producing a five-membered ring having almost the same chain as lobarin.

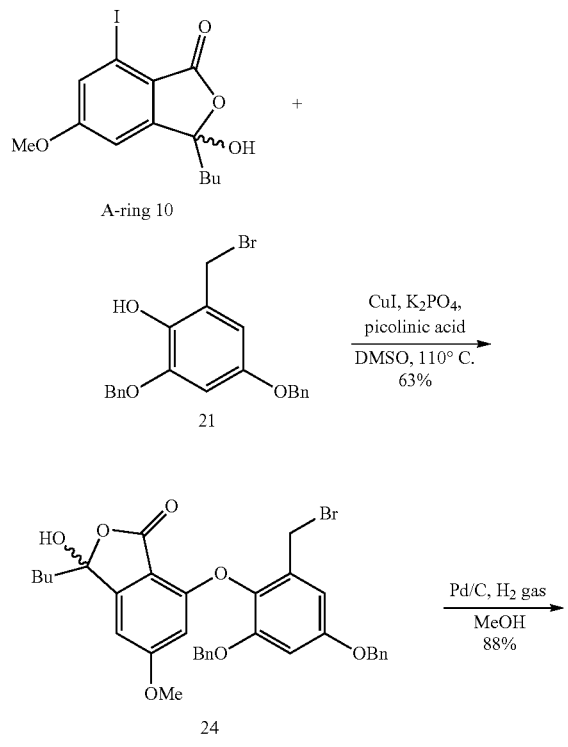

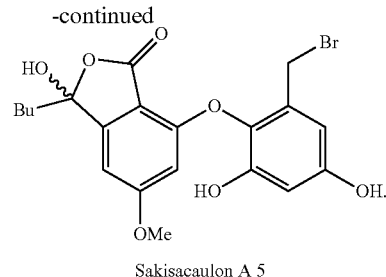

Sakisacaulon A 5

For diaryl ether coupling, the ring-A and the B ring-2 (21) are subjected to Ullmann coupling reaction under heating in DMSO/$K_3PO_4$ using copper as a catalyst and picolinic acid as a ligand to obtain coupling product (24). After the coupling reaction, the benzyl protecting group of the product 24 is deprotected using Pd/C and $H_2$ gas to obtain sakisacaulon A (5).

Hereinafter, the present invention will be described in more detail with reference to examples. It will be obvious to skilled in the art that these examples are provided merely to illustrate the present invention, and the scope of the present invention is not limited by these examples.

EXAMPLES

All glassware was dried completely in a drying oven and cooled with dry argon gas before use. All reactions were carried out in an inert argon atmosphere.

Unless otherwise specified, anhydrous solvents and reagents were purchased from Aldrich. TCI was used without further purification. Solvents and liquid reagents were added by a syringe. Thin-film chromatography was performed using a 0.25 mm silica gel plate (Merck). Flash column chromatography was performed using silica gel 60 (230-400 mesh, Merck) containing the described solvent. Organic extracts were dried with the drying agent $MgSO_4$, $NaHCO_3$ or $Na_2SO_4$, and concentrated under reduced pressure using a rotary evaporator. Infrared spectra were recorded using a Thermo Scientific Nicolet 6700 FT-IR spectrometer. High-resolution mass spectra were obtained using an AB Sciex Triple TOF 4600 instrument. $^1H$ and $^{13}C$ NMR spectra were measured using an Agilent 400 MHz spectrometer in CDCl₃, CD₃OD and dimethyl sulfoxide-D₆ solutions. Chemical shifts were expressed as parts per million (ppm) in downfield from TMS, and a deuterium-containing solvent was used as a reference material.

Example 1

Synthesis of Lobarin (3)

Example 1-1

Synthesis of 4-Methoxy-Phthalic Acid (7)

[Formula 7]

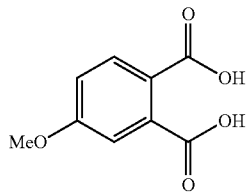

7

MeONa (2 g, 37 mmol), MeOH (30 ml), CuCl (90 mg, 0.67 mmol), HCOOMe (0.4 ml, 6.7 mmol) and 4-bromophthalic anhydride (3 g, 16.8 mmol) were added to a 100-ml dry sealed tube and heated at 120° C. for 8 hours with stirring. After completion of the reaction, the reactor was cooled to room temperature. The mixture was stirred for 0.5 hours and concentrated under reduced pressure. Ethyl acetate and 1N HCl were added to the residue. The mixture was separated into two layers, and the aqueous phase was extracted three times with ethyl acetate. The obtained organic phase was dried with anhydrous Na₂SO₄, concentrated, and then purified by recrystallization from ethyl acetate. The yield was 90%.

Figure 2:
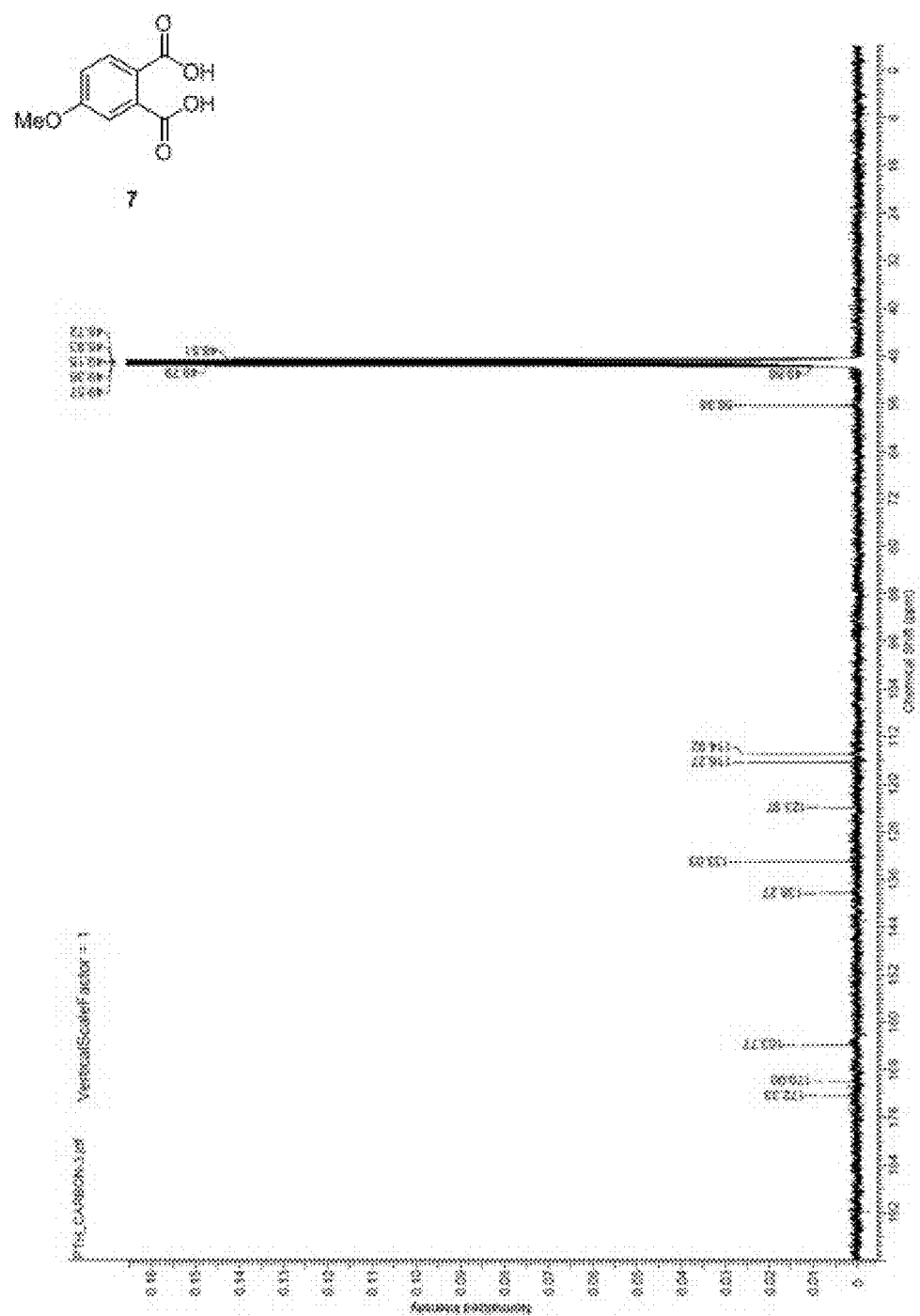
FIG. 2 is the 101 MHz $^{13}$C-NMR (in $CD_3OD$) of a compound of Formula 7 according to one example of the present invention.

FIG. 1 shows the 400 MHz ¹H-NMR spectrum (in CD₃OD) of the compound of Formula 7, and FIG. 2 shows the 101 MHz ¹³C-NMR (in CD₃OD) of the compound of Formula 7.

¹H NMR (400 MHz, acetone-$d_6$) δ=7.84 (d, J=8.6, 1H), 7.11 (d, J=2.4, 1H), 7.09 (dd, J=2.4, 8.6, 1H), 3.88 (s, 3H); ¹³C NMR (101 MHz, CD₃OD) δ=172.3, 170.0, 163.8, 138.3, 133.0, 124.0, 116.3, 115.0, 56.4; HRMS (ESI-TOF) m/z calculated for $C_9H_9O_5$ [M+H]⁺: 197.0450, found: 197.0440.

Example 1-2

Synthesis of 4-Methoxy-Phthalic Anhydride (8)

[Formula 8]

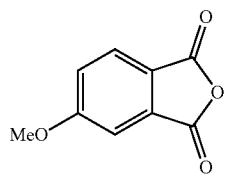

8

4-methoxy phthalic acid (3 g, 15.3 mmol) was added to a dried flask and dissolved in anhydrous THF. Acetic anhydride (4 ml, 42.3 mmol) was added thereto, followed by reflux under heating for about 4 hours. After cooling to room temperature, concentration under reduced pressure afforded the compound of Formula 8.

HRMS (ESI-TOF) m/z calculated for $C_9H_7O_4$ [M+H]⁺: 179.0344, found: 179.0340.

Example 1-3

Synthesis of 3-Butyl-3-Hydroxy-5-Methoxyisobenzofuran-1-(3H)-One (9)

[Formula 9]

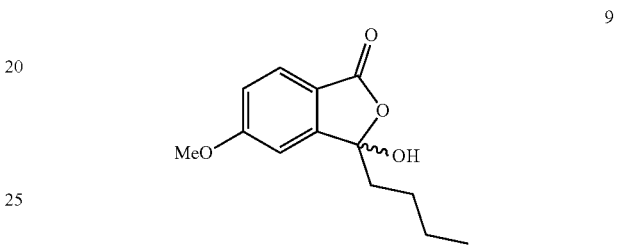

9

4-methoxy-phthalic anhydride (8) (3 g, 16.8 mmol) and copper chloride (158 mg, 1.2 mmol) were dried completely and dissolved in 200 ml of THF in a round flask. The solution was cooled to −20° C., and 9.3 ml of 2.0M butyl magnesium chloride was added slowly thereto. After completion of the addition, the mixture was stirred at −20° C. for about 12 hours, and the reaction was terminated by addition of 1N HCl. The reaction product was extracted with EA and purified by a silica gel column using hexane and EA. The yield was 52%.

Figure 3:
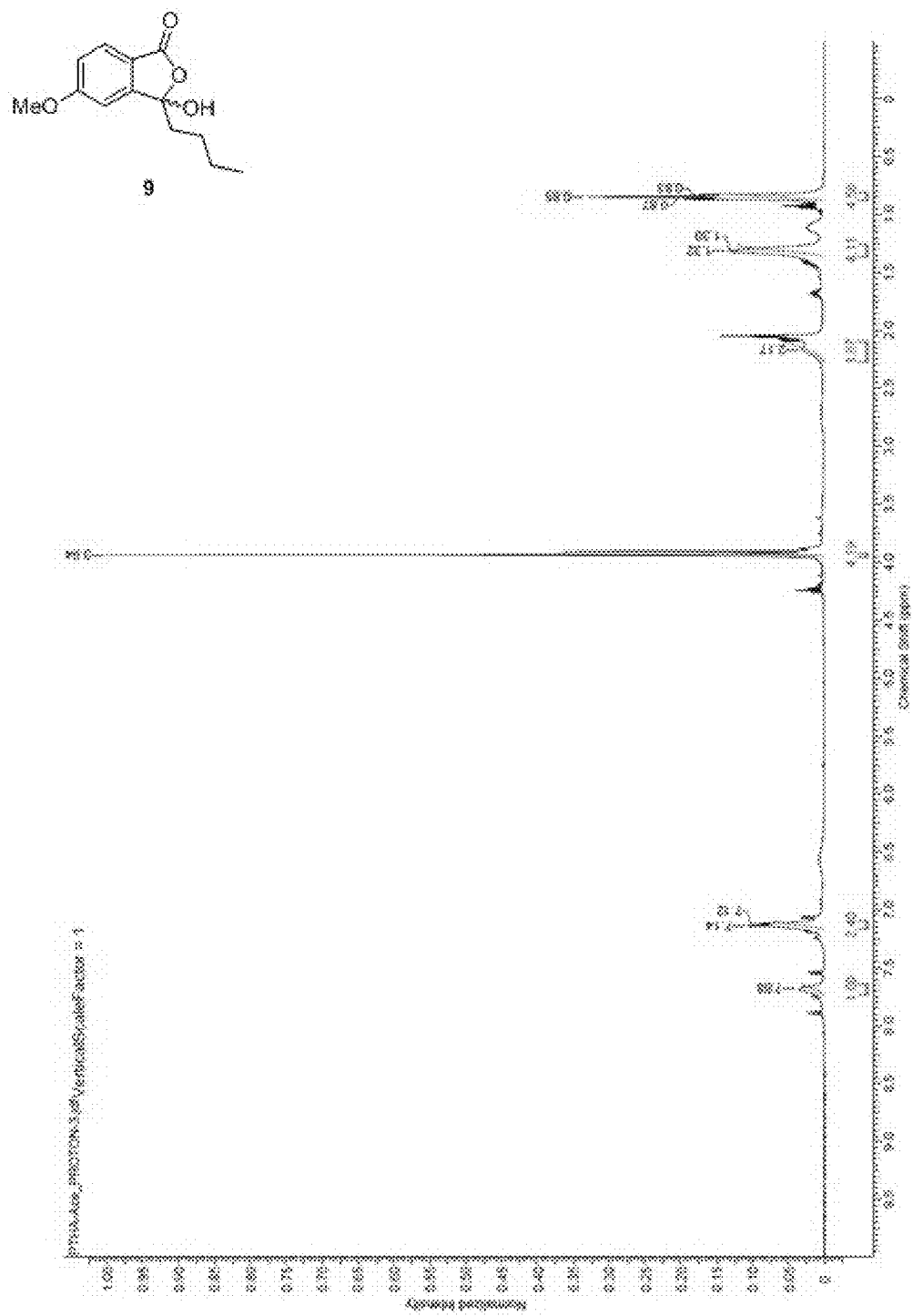
FIG. 3 is the 400 MHz $^1$H-NMR spectrum (in acetone-$D_6$) of a compound of Formula 9 according to one example of the present invention.
Figure 4:
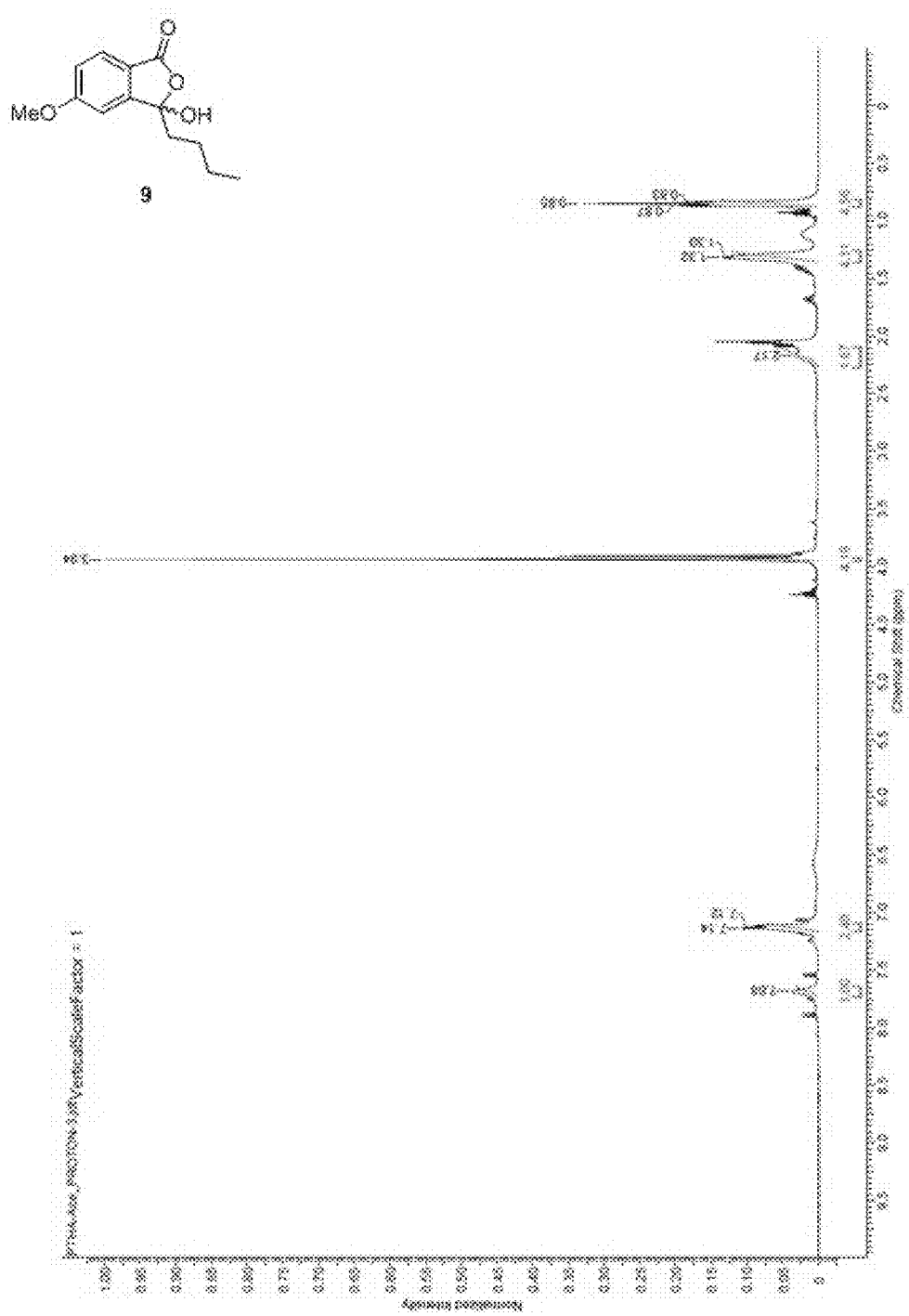
FIG. 4 is the 101 MHz $^{13}$C-NMR (in acetone-$D_6$) of a compound of Formula 9 according to one example of the present invention.

FIG. 3 shows the 400 MHz ¹H-NMR spectrum (in acetone-$d_6$) of the compound of Formula 9, and FIG. 4 shows the 101 MHz ¹³C-NMR (in acetone-$d_6$) of the compound of Formula 9.

¹H NMR (400 MHz, Acetone $d_6$) δ=7.68 (s, 1H), 7.14 (s, 1H), 7.12 (s, 1H), 3.94 (s, 3H), 2.17 (m, 2H), 1.32 (m, 4H), 0.85 (t, J=7.3, 3H); ¹³C NMR (101 MHz, Acetone $d_6$) δ=168.4, 167.3, 166.0, 153.4, 127.1, 120.3, 118.2, 107.6, 55.5, 39.4, 26.5, 23.2, 14.2; HRMS (ESI-TOF) m/z calculated for $C_{13}H_{17}O_4$ [M+H]⁺: 237.1127, found: 237.1121.

Example 1-4

Synthesis of 3-Butyl-3-Hydroxy-7-Iodo-5-Methoxy-isobenzofuran-1-(3H)-One (10)

[Formula 10]

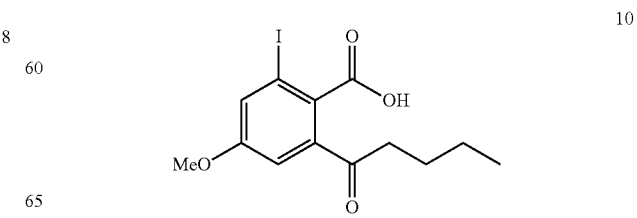

10

In a 1000-ml round-bottom flask, compound 9 (6 g, 25.4 mmol), Pd(OAc)$_2$ (570 mg, 2.5 mmol), (diacetoxy)benzene (9.8 g, 30.5 mmol) and iodine (7.7 g, 30.5 mmol) were dissolved in DMF in air. The reaction flask was sealed with a cap, and the reaction mixture was stirred at 60° C. for 12 hours. The reaction mixture was cooled to room temperature, diluted with ethyl acetate, and then washed with 1N HCl. The organic phase was washed with brine, dried with Na$_2$SO$_4$, and then concentrated in a rotary evaporator. The product was purified by silica column chromatography. The yield was 78%.

Figure 5:
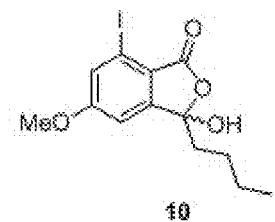
FIG. 5 is the 600 MHz $^1$H-NMR spectrum (in $CD_3OD$) of a compound of Formula 10 according to one example of the present invention.
Figure 5:
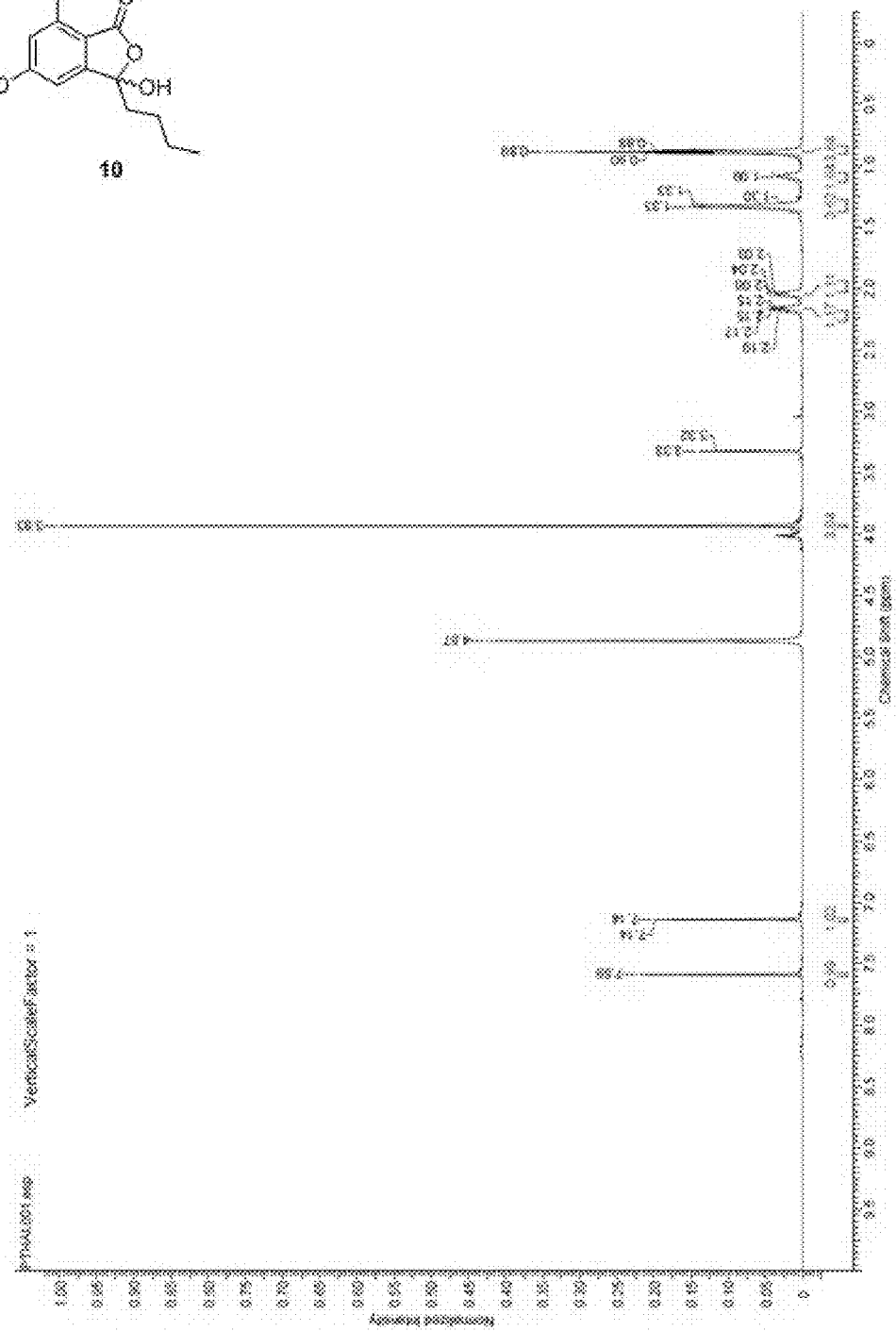
Figure 6:
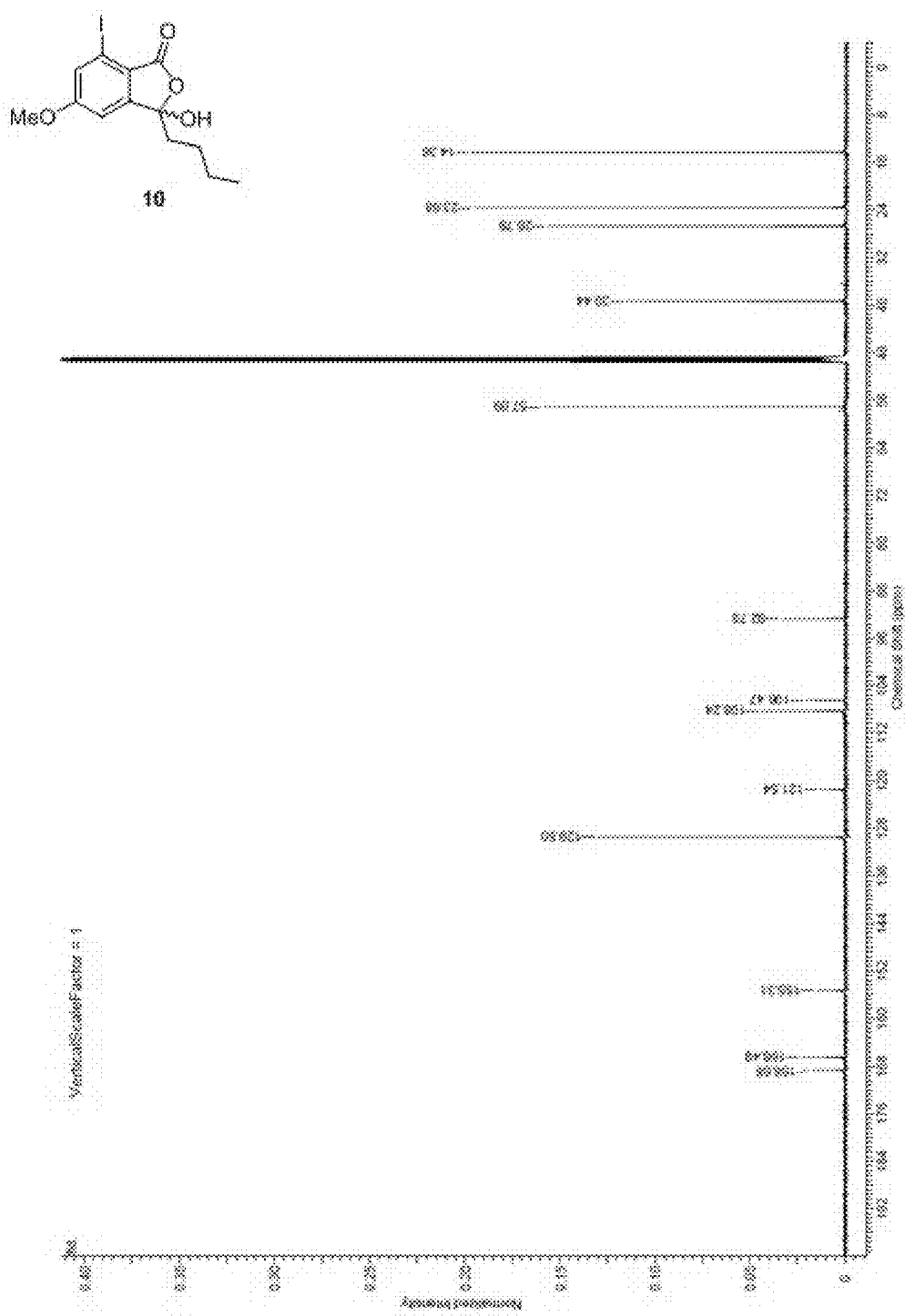
FIG. 6 is the 150 MHz $^{13}$C-NMR spectrum (in $CD_3OD$) of a compound of Formula 10 according to one example of the present invention.
Figure 7:
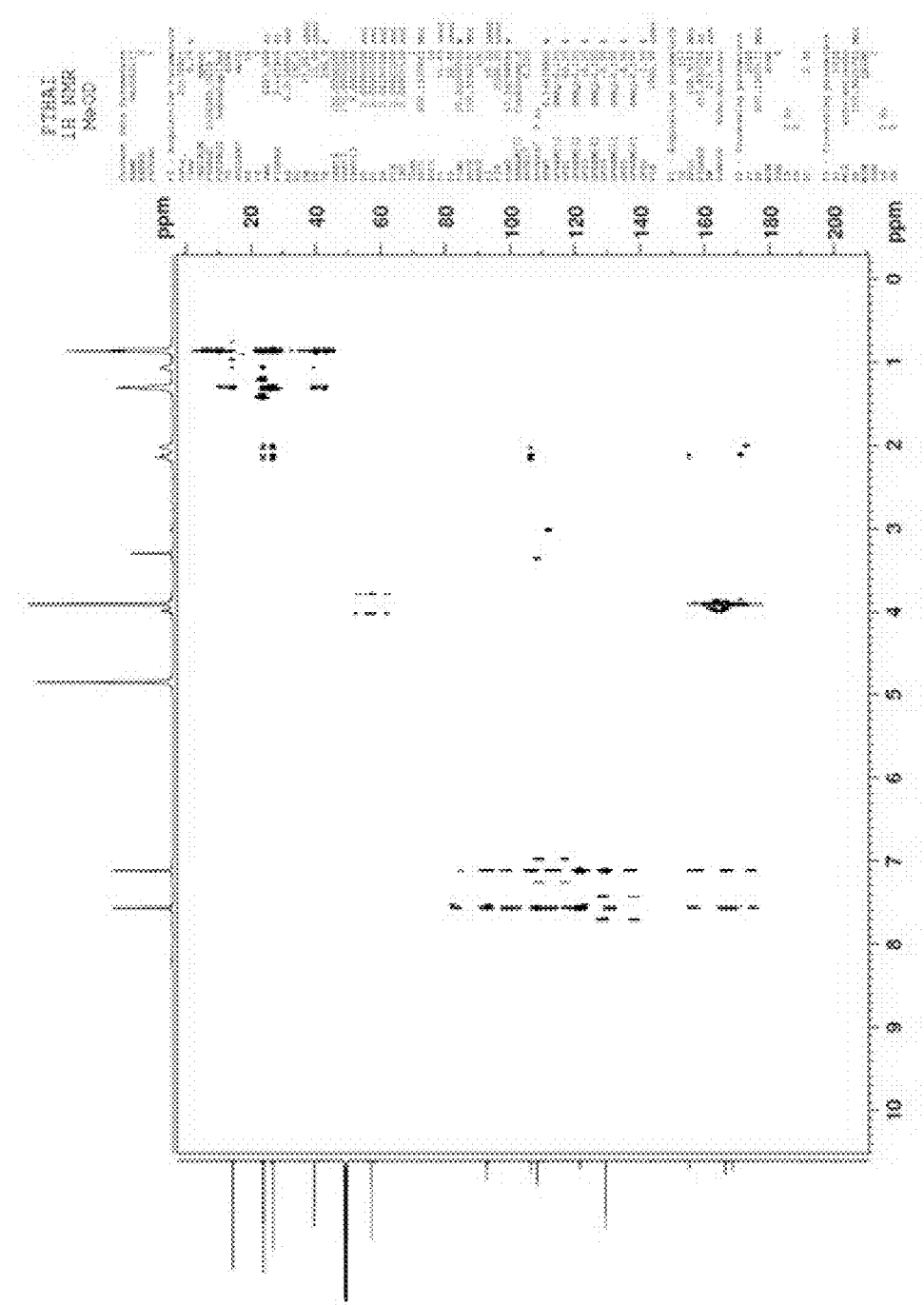
FIG. 7 is the HMBC spectrum (in $CD_3OD$) of a compound of Formula 10 according to one example of the present invention.

FIGS. 5, 6 and 7 show the 600 MHz $^1$H-NMR spectrum (in CD$_3$OD), 150 MHz $^{13}$C-NMR spectrum (in CD$_3$OD) and HMBC spectrum (in CD$_3$OD) of the compound of Formula 10, respectively.

$^1$H NMR (600 MHz, CD$_3$OD) δ=7.59 (d, J=1.0, 1H), 7.14 (d, J=1.0, 1H), 3.93 (s, 3H), 2.19-2.03 (m, 2H)), 1.33 (m, 3H), 1.09 (m, 1H), 0.89 (t, J=6.8, 3H); $^{13}$C NMR (151 MHz, CD$_3$OD) δ=168.7, 166.5, 155.3, 129.5, 121.5, 108.2, 106.5, 93.8, 57.1, 39.4, 26.8, 23.7, 14.4; HRMS (ESI-TOF) m/z calculated for C$_{13}$H$_{16}$IO$_4$ [M+H]$^+$: 363.0093, found: 363.0084.

Example 1-5

Synthesis of Benzyl 2,4-Bis(Benzyloxy)Benzoate (12)

[Formula 12]

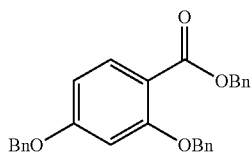

12

The starting material 2,4-dihydroxy benzoic acid (20 g, 130 mmol) was dissolved in 200 ml of DMF in a 2L round-bottom flask. Benzyl bromide (62 ml, 519 mmol) and potassium carbonate (72 g, 519 mmol) were added to the reaction flask at room temperature. After stirring at room temperature for 12 hours, the reaction temperature was increased to 90° C., followed by stirring for 1 hour. Ethyl acetate and 1N HCl were added to the reaction residue. The mixture was separated into two layers, and the aqueous phase was extracted three times with ethyl acetate. The obtained organic layer was dried with anhydrous Na$_2$SO$_4$, concentrated, and then purified by recrystallization from MeOH. The yield was 98%.

Figure 8:
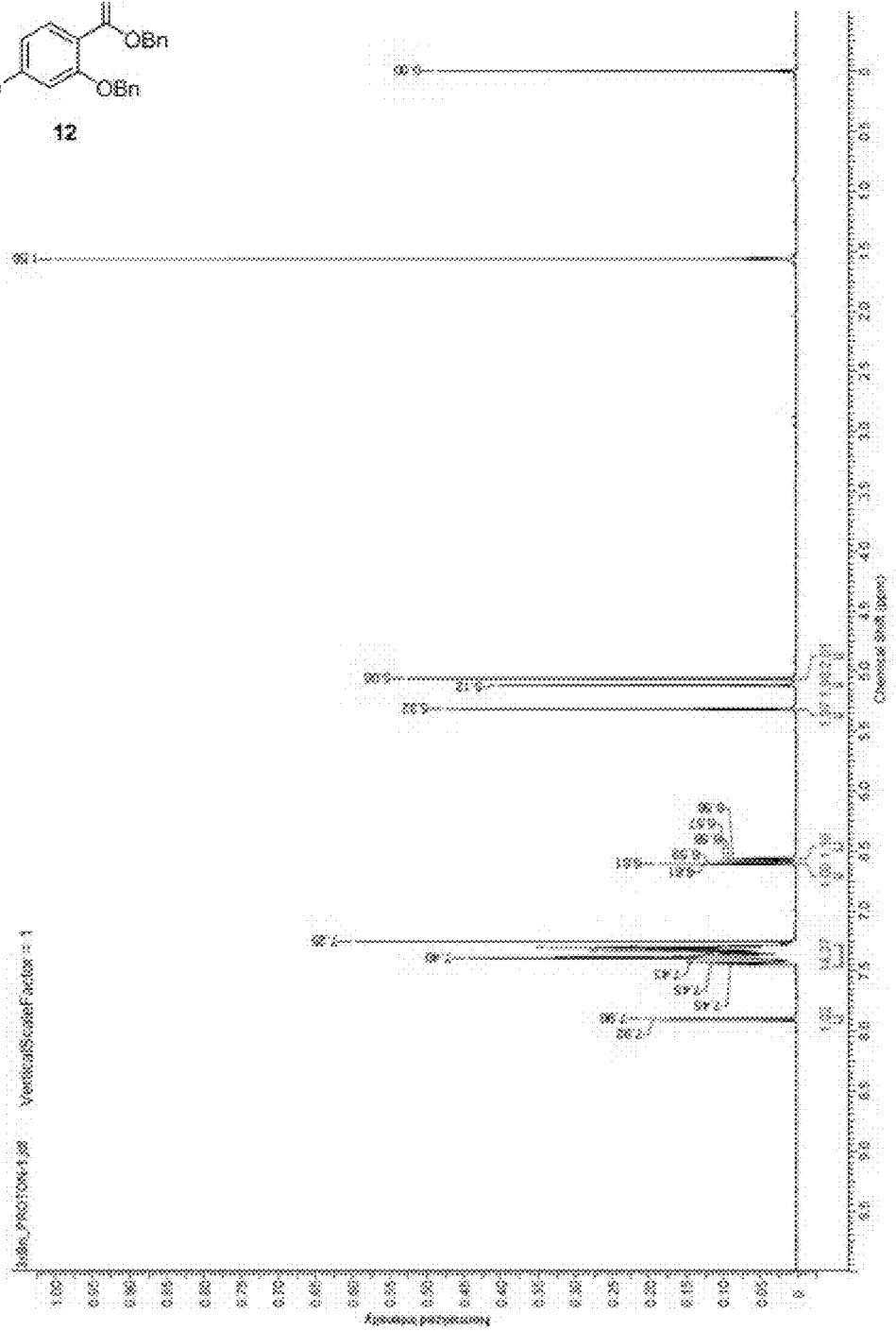
FIG. 8 is the 400 MHz $^1$H-NMR spectrum (in $CD_3OD$) of a compound of Formula 12 according to one example of the present invention.
Figure 9:
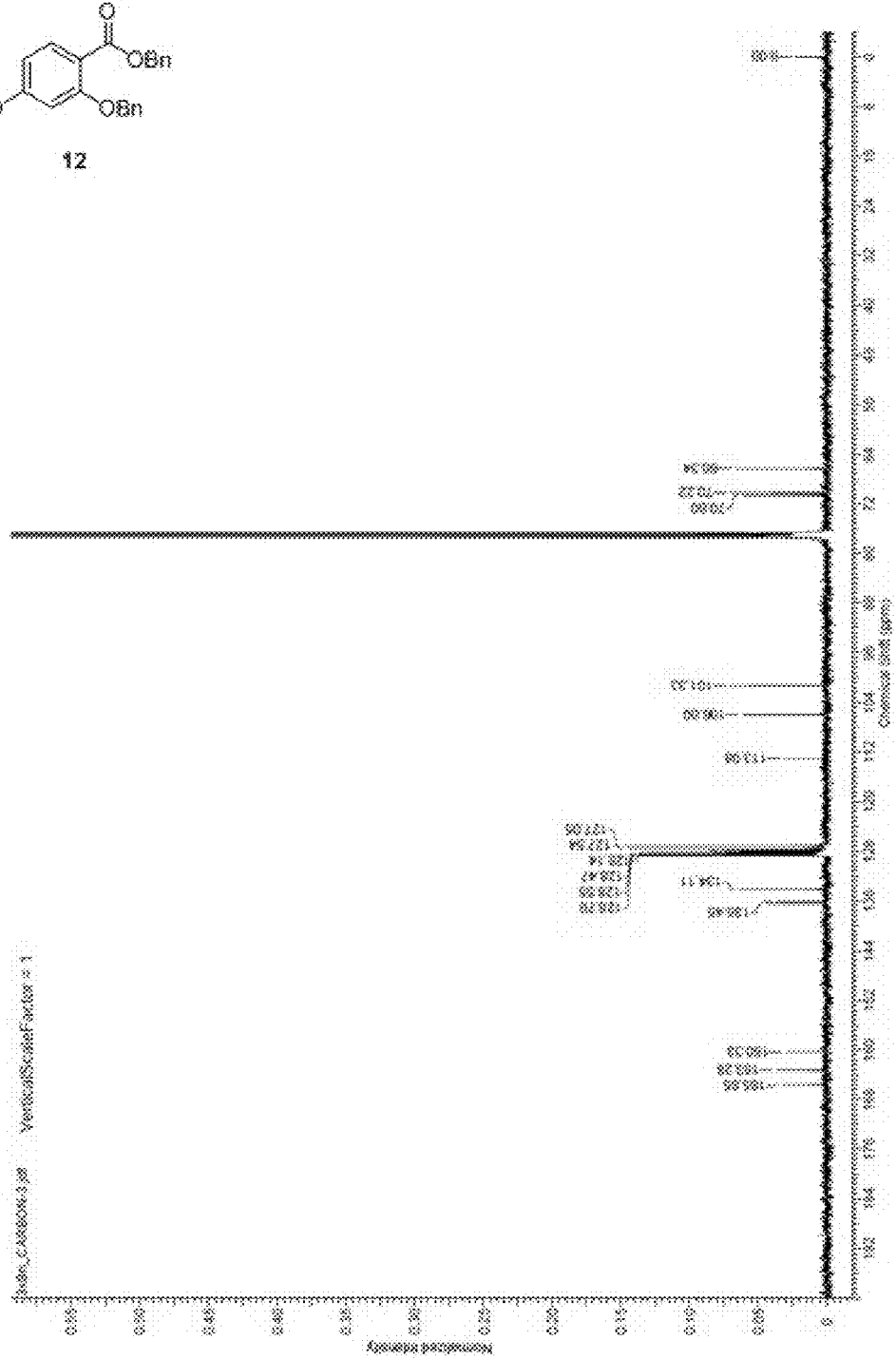
FIG. 9 is the 101 MHz $^{13}$C-NMR spectrum (in CD$_3$OD) of a compound of Formula 12 according to one example of the present invention.

FIG. 8 shows the 400 MHz $^1$H-NMR spectrum (in CD$_3$OD) of the compound of Formula 12, and FIG. 9 shows the 101 MHz $^{13}$C-NMR spectrum (in CD$_3$OD) of the compound of Formula 12.

$^1$H NMR (400 MHz, CDCl$_3$) δ=7.91 (d, J=8.6, 1H), 7.40-7.26 (m, 15H), 6.61 (d, J=2.4, 1H), 6.57 (dd, J=2.4, 8.6, 1H), 5.32 (s, 2H), 5.12 (s, 2H), 5.06 (s, 2H); $^{13}$C NMR (101 MHz, CDCl$_3$) δ=165.6, 163.3, 160.3, 136.4, 136.3, 134.1, 128.7, 128.5, 128.4, 128.2, 128.1, 127.8, 127.5, 127.0, 113.1, 106.0, 101.3, 70.6, 70.2, 66.3; HRMS (ESI-TOF) m/z calculated for C$_{28}$H$_{25}$O$_4$ [M+H]$^+$: 425.1753, found: 425.1740.

Example 1-6

Synthesis of Benzyl 2,4-Bis(Benzyloxy)-6-Iodobenzoate (13)

[Formula 13]

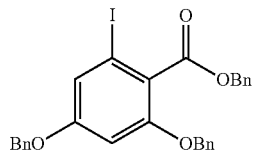

13

In a 1000-ml round-bottom flask, benzyl 2,4-bis(benzyloxy)benzoate (12) (5 g, 15 mmol), Pd(OAc)$_2$ (337 mg, 1.5 mmol), (diacetoxy)benzene (7.2 g, 22.5 mmol) and iodine (5.7 g, 22.5 mmol) were dissolved in DMF in air. The reaction flask was sealed with a cap, and the reaction mixture was stirred at 60° C. for 12 hours. The reaction mixture was cooled to room temperature, diluted with ethyl acetate, and then washed with 1N HCl. The organic phase was washed with brine, dried with Na$_2$SO$_4$, and then evaporated in a rotary evaporator. The residue was purified by silica column chromatography. The yield was 78%.

Figure 10:
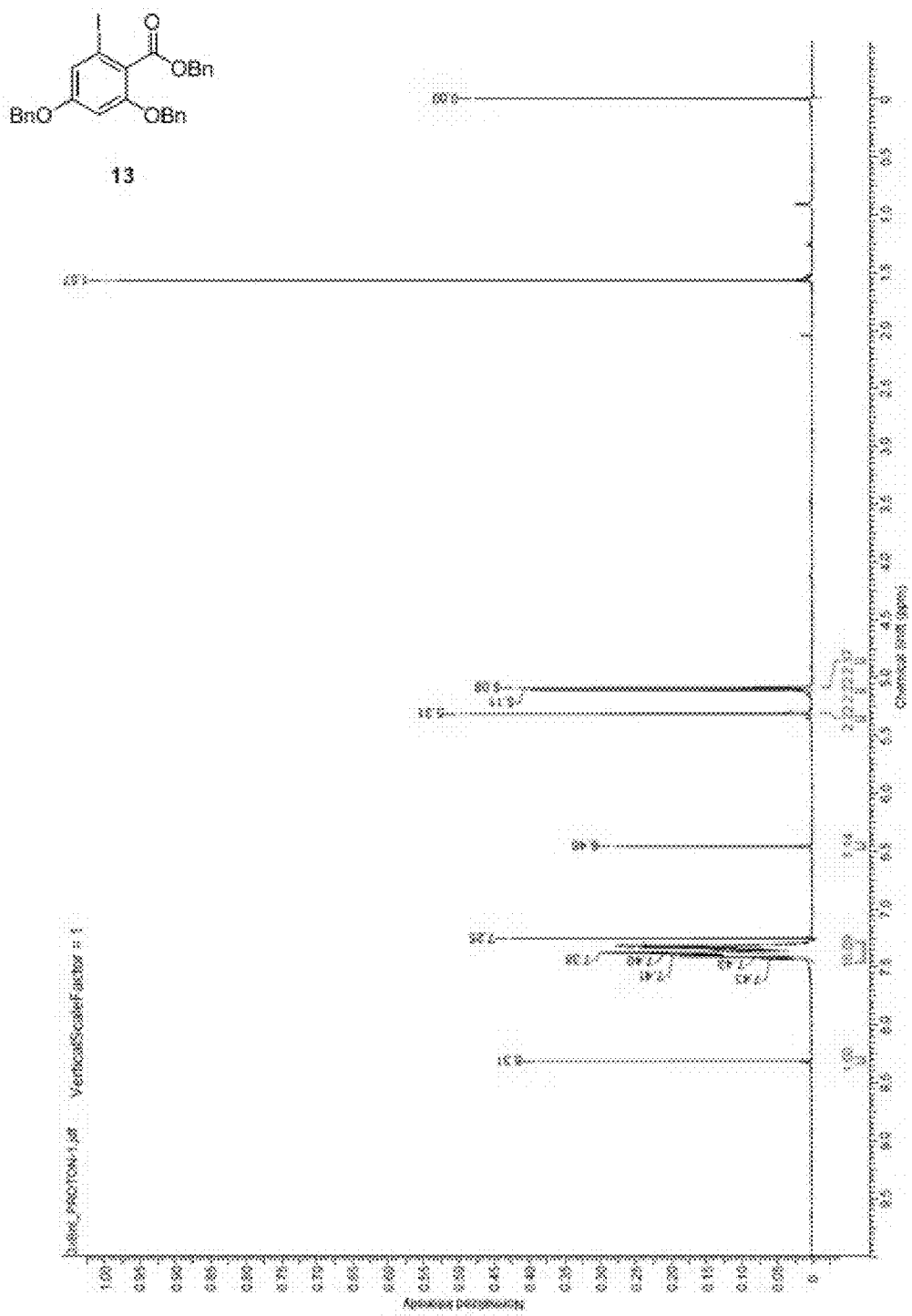
FIG. 10 is the 400 MHz $^1$H-NMR spectrum (in CD$_3$OD) of a compound of Formula 13 according to one example of the present invention.
Figure 11:
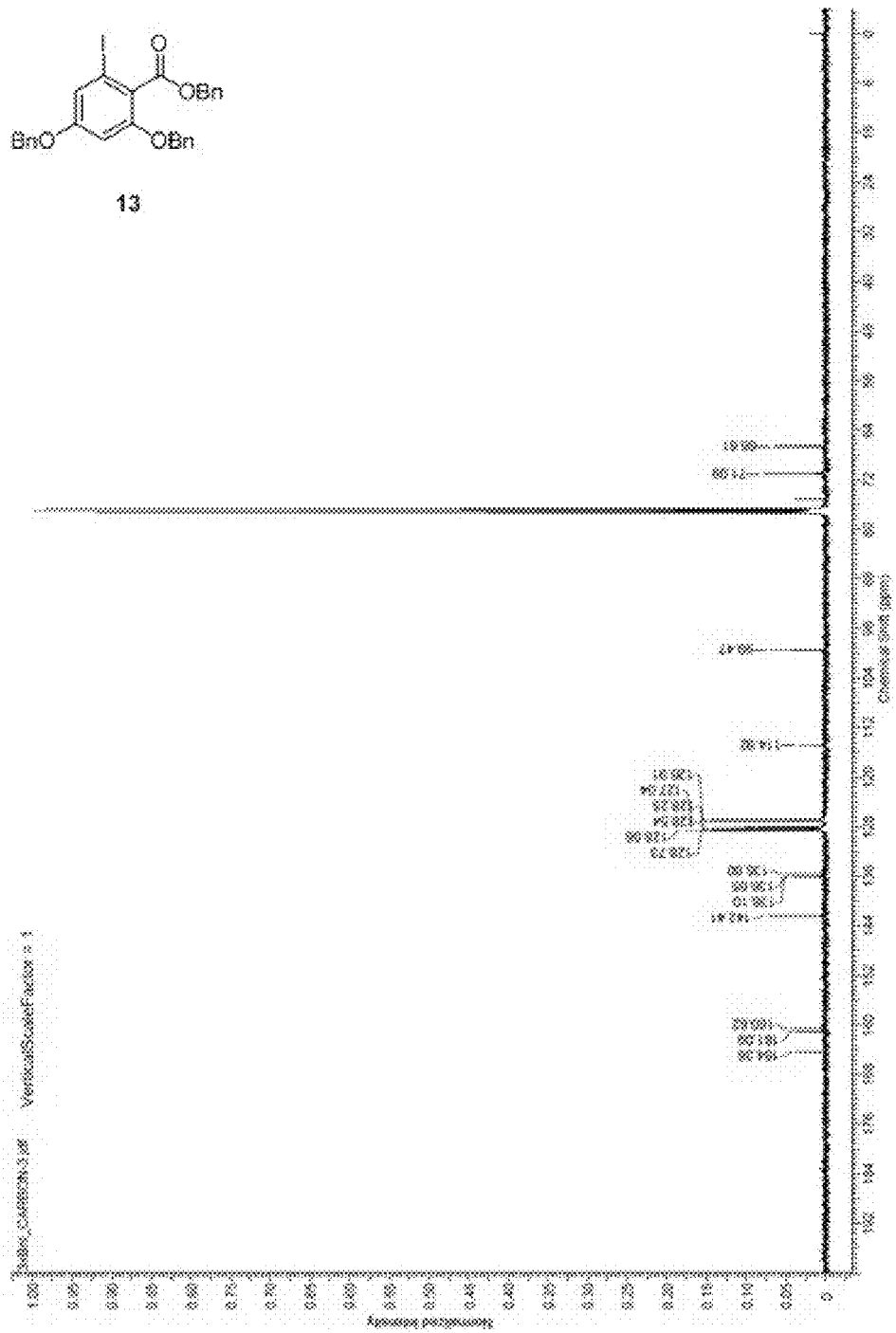
FIG. 11 is the 101 MHz $^{13}$C-NMR spectrum (in CD$_3$OD) of a compound of Formula 13 according to one example of the present invention.

FIG. 10 shows the 400 MHz $^1$H-NMR spectrum (in CD$_3$OD) of the compound of Formula 13, and FIG. 11 shows the 101 MHz $^{13}$C-NMR spectrum (in CD$_3$OD) of the compound of Formula 13.

$^1$H NMR (400 MHz, CDCl$_3$) δ=8.31 (s, 1H), 7.39-7.32 (m, 15H), 6.46 (s, 1H), 5.31 (s, 2H), 5.11 (s, 2H), 5.08 (s, 2H); $^{13}$C NMR (101 MHz, CDCl$_3$) δ=164.3, 161.1, 160.6, 142.4, 136.1, 136.0, 135.6, 128.7, 128.6, 128.2, 128.1, 128.0, 127.0, 126.9, 114.9, 99.5, 75.1, 71.0, 66.6; HRMS (ESI-TOF) m/z calculated for C$_{28}$H$_{24}$IO$_4$ [M+H]$^+$: 551.0719, found: 551.0709.

Example 1-7

Synthesis of Benzyl 2,4-Bis(Benzyloxy)-6-Pentylbenzoate (14)

[Formula 14]

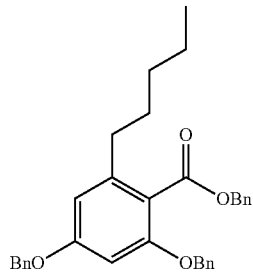

14

Starting material compound 13: benzyl 2,4-bis(benzyloxy)-6-iodobenzoate (13), palladium acetate, silver carbonate, potassium carbonate, pentylboronic acid, and DMF as a solvent were added to a dried round-bottom flask equipped with a magnetic bar, and the flask was filled with Ar gas. The flask was transferred into an oil bath at 110° C. and stirred for 12 hours, and the reaction was terminated by addition of 1N HCl. The reaction solution was extracted with Et₂O, dried in vacuo, and purified by silica gel chromatography. The yield was 28%.

Starting material compound 19: The starting material 2,4-dihydroxyl-6-pentylbenzoic acid (19) (5 g, 22.3 mmol) was dissolved in 50 ml of DMF in a round-bottom flask. Benzyl bromide (1.06 ml, 89.2 mmol) and potassium carbonate (1.23 g, 89.2 mmol) were added to the reaction flask at room temperature. The reaction mixture was stirred at room temperature for 18 hours, and ethyl acetate and 1N HCl were added to the reaction residue. The mixture was separated into two layers, and the aqueous phase was extracted three times with ethyl acetate. The obtained organic layer was dried with anhydrous Na₂SO₄, concentrated, and then purified by recrystallization from MeOH. The yield was 98%.

Figure 12:
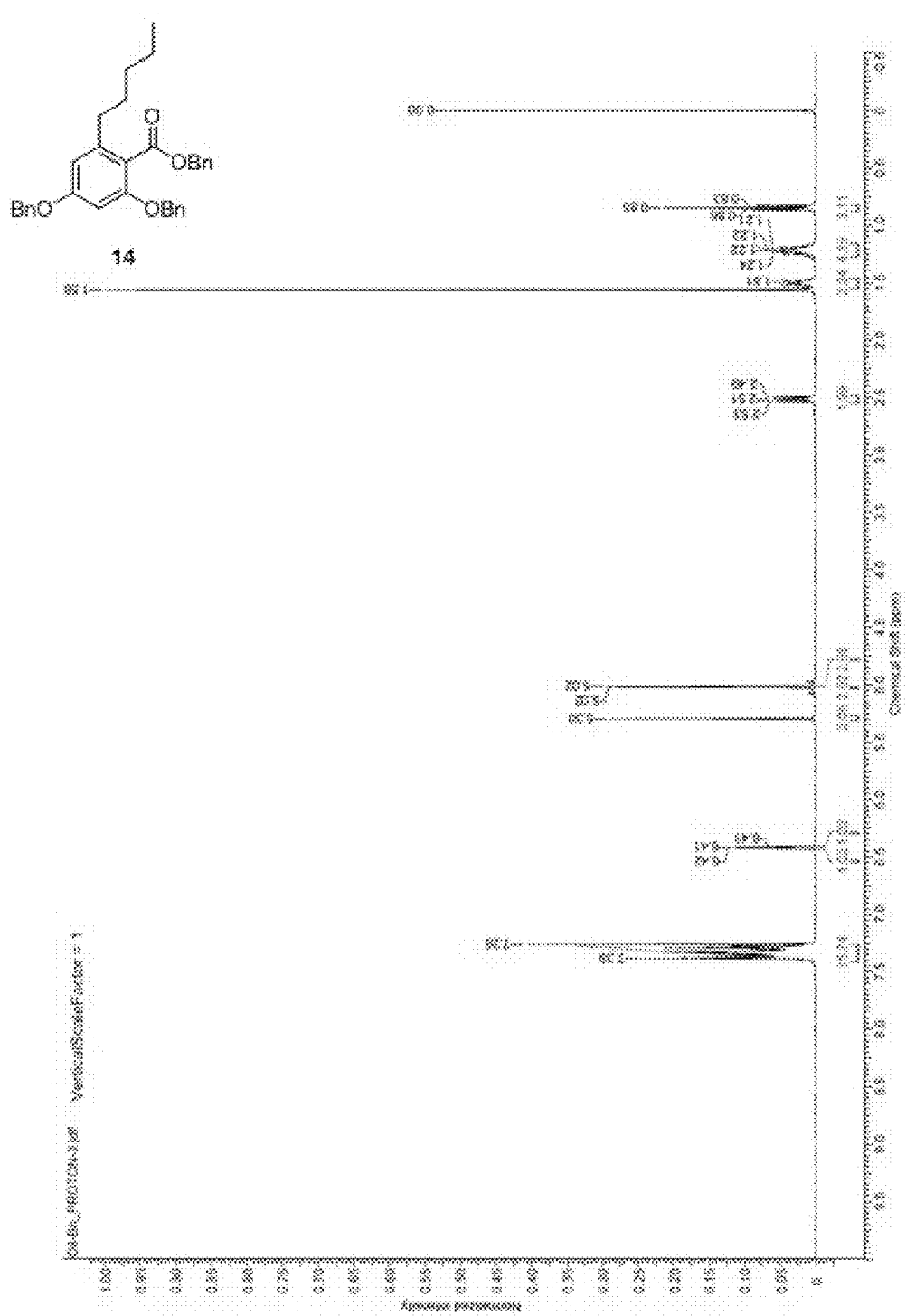
FIG. 12 is the 400 MHz $^1$H-NMR spectrum (in CD$_3$OD) of a compound of Formula 14 according to one example of the present invention.
Figure 13:
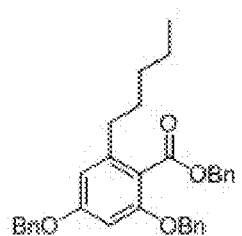
FIG. 13 is the 101 MHz $^{13}$C-NMR spectrum (in CD$_3$OD) of a compound of Formula 14 according to one example of the present invention.
Figure 13:
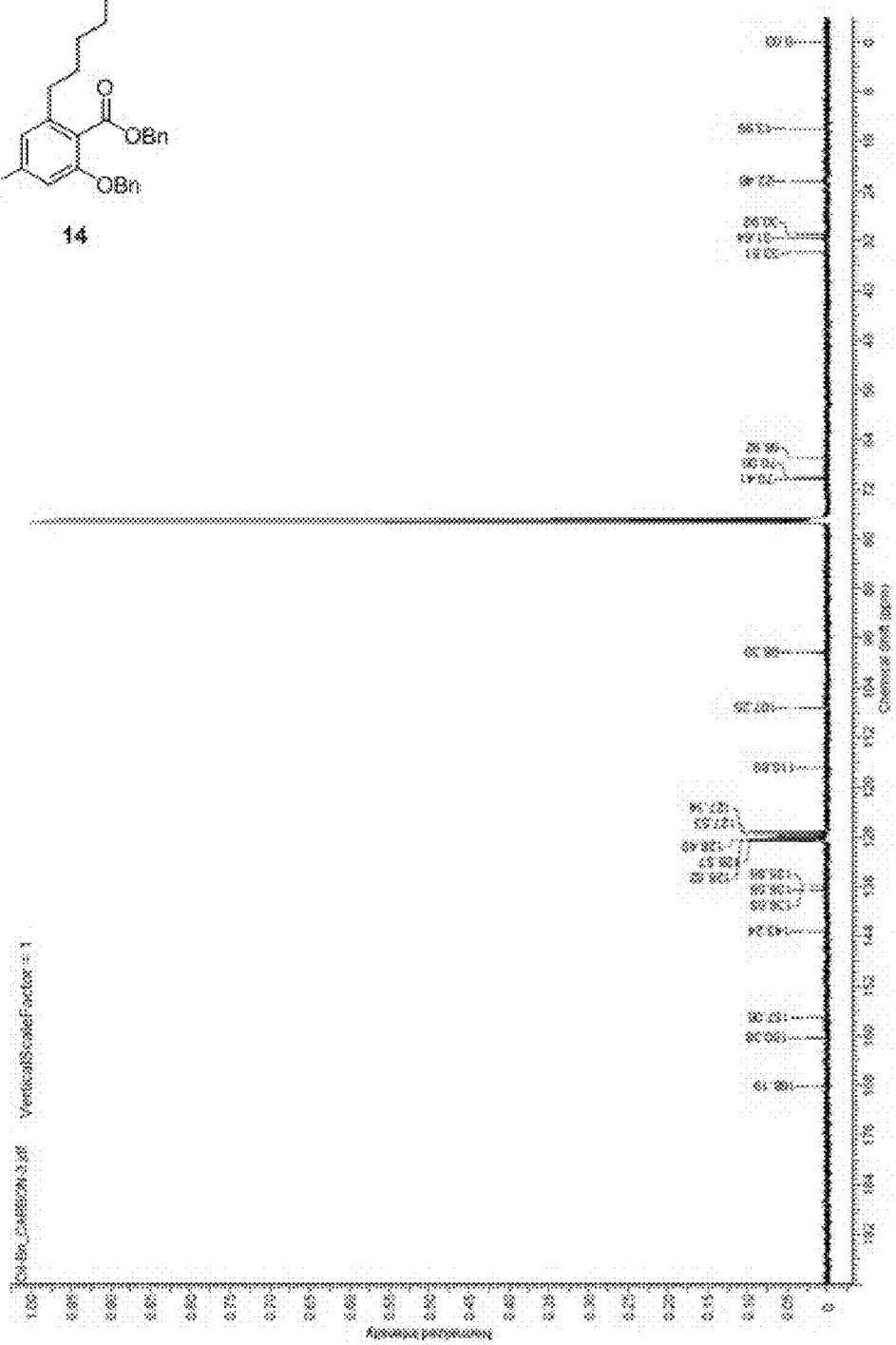

FIG. 12 shows the 400 MHz ¹H-NMR spectrum (in CD₃OD) of the compound of Formula 14, and FIG. 13 shows the 101 MHz ¹³C-NMR spectrum (in CD₃OD) of the compound of Formula 14.

¹H NMR (400 MHz, CDCl₃) δ=7.39-7.27 (m, 15H), 6.42 (d, J=2.4, 1H), 6.41 (d, J=2.4, 1H), 5.30 (s, 2H), 5.02 (s, 2H), 5.01 (s, 2H), 2.51 (t, J=7.9, 2H), 1.53 (m, 2H), 1.22 (m, 4H), 0.85 (t, J=6.7, 3H); ¹³C NMR (101 MHz, CDCl₃) δ=168.2, 160.4, 157.0, 143.2, 136.6, 136.5, 135.8, 128.60, 128.55, 128.5, 128.4, 128.1, 128.0, 127.8, 127.5, 127.1, 116.9, 107.2, 98.3, 70.4, 70.1, 66.9, 33.8, 31.6, 30.9, 22.4, 14.0; HRMS (ESI-TOF) m/z calculated for $C_{33}H_{35}O_4$ [M+H]⁺: 495.2535, found: 495.2544.

Example 1-8

Synthesis of Benzyl 4,6-Bis(Benzyloxy)-3-Formyl-2-Pentylbenzoate (15)

[Formula 15]

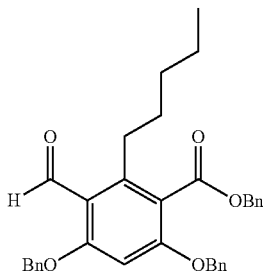

POCl₃ (1.24 ml, 13.4 mmol) was precipitated in 10 ml of DMF at a temperature lower than 10° C. with rapid stirring for 0.5 hours or more. While the temperature was maintained at lower than 10° C., benzyl 2,4-bis(benzyloxy)-6-pentylbenzoate (14) (4.4 g, 8.9 mmol) was added to 10 ml of DMF. The mixture was warmed to 70° C. and stirred for 8 hours. Ethyl acetate and 1N HCl were added to the residue. The mixture was separated into two layers, and the aqueous phase was extracted three times with ethyl acetate. The obtained organic layer was dried with anhydrous Na₂SO₄, concentrated, and then purified by silica gel chromatography. The yield was 92%.

Figure 14:
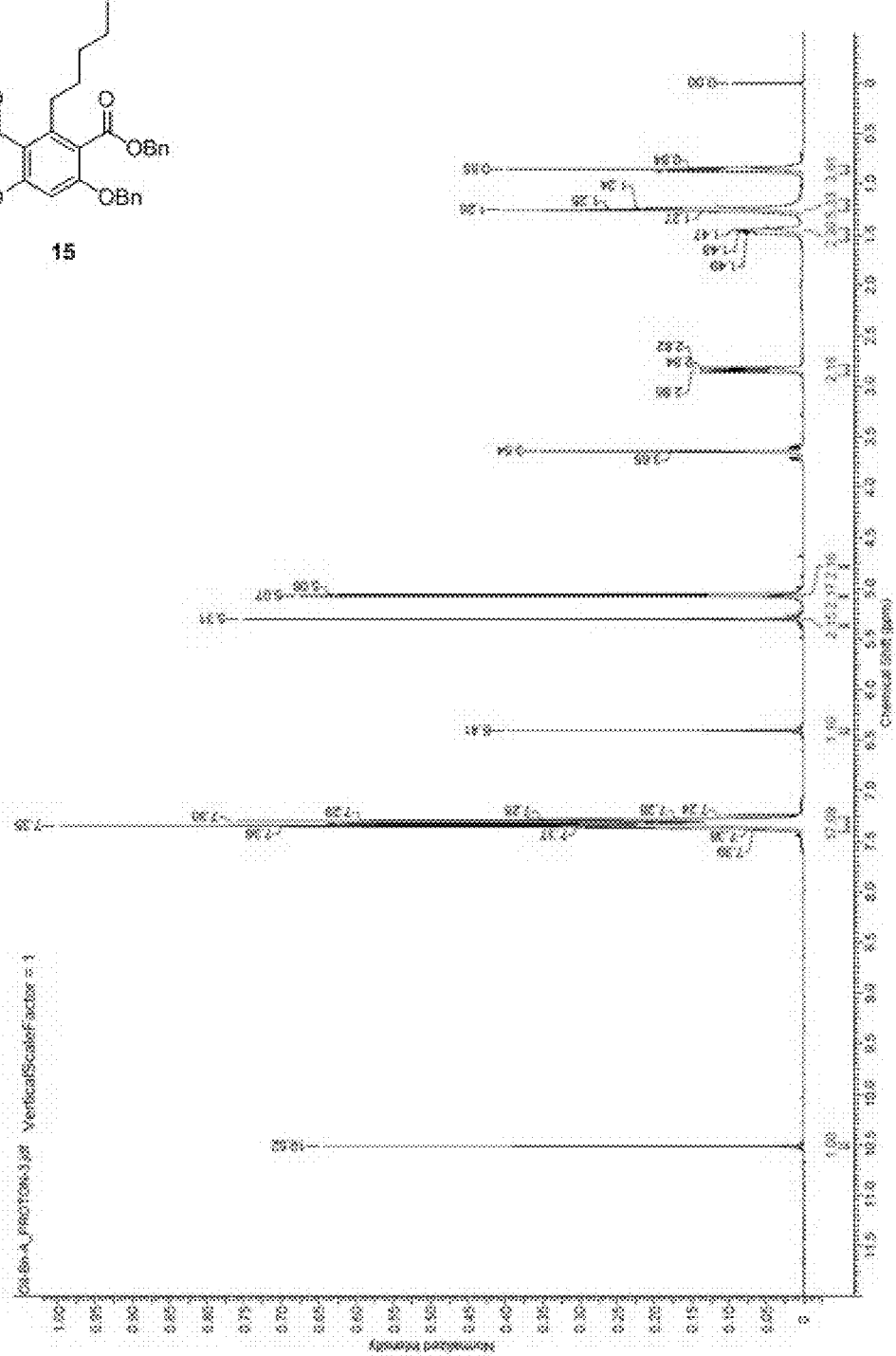
FIG. 14 is the 400 MHz $^1$H-NMR spectrum (in CDCl$_3$) of a compound of Formula 15 according to one example of the present invention.
Figure 15:
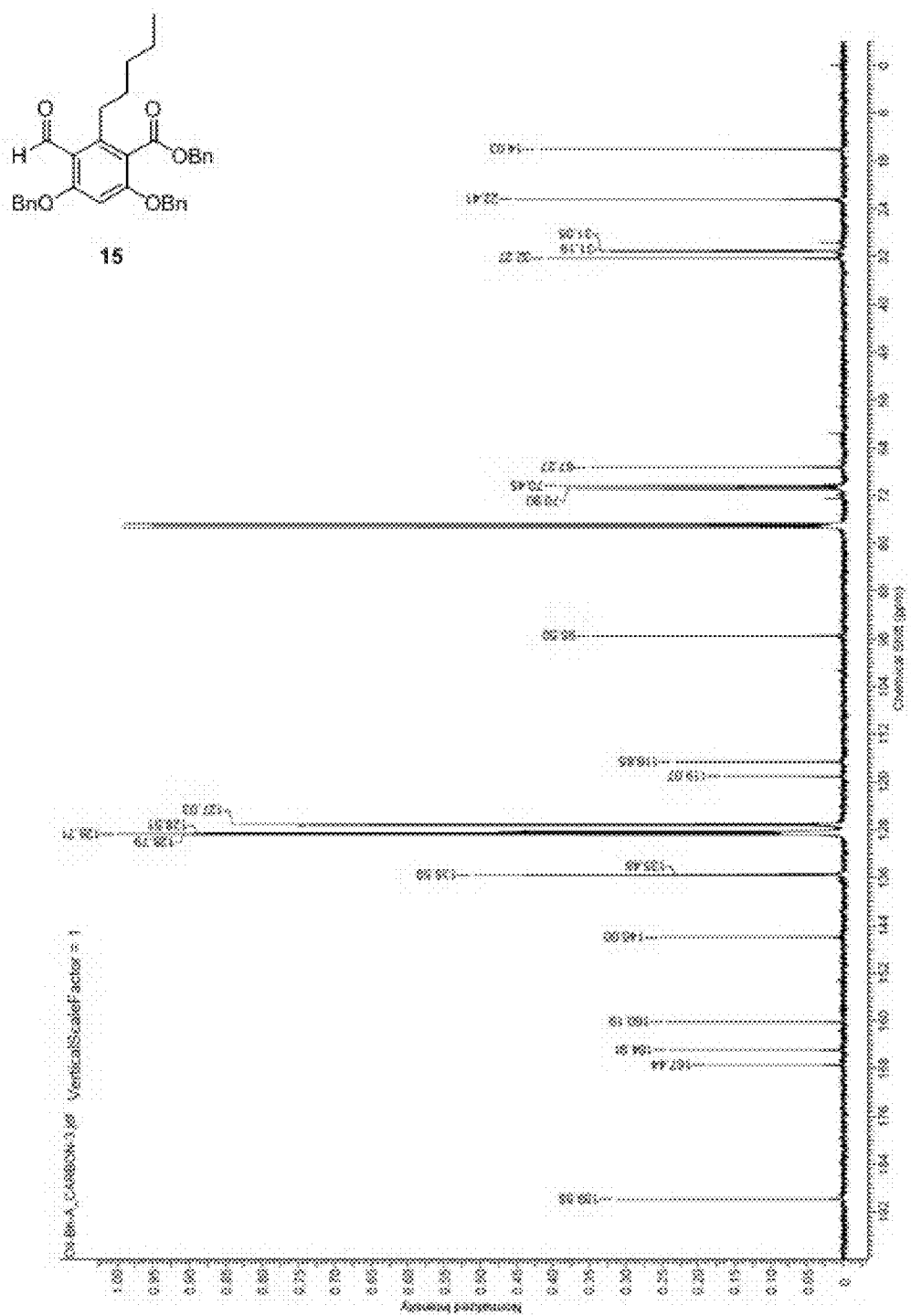
FIG. 15 is the 101 MHz $^{13}$C-NMR spectrum (in CD$_3$OD) of a compound of Formula 15 according to one example of the present invention.

FIG. 14 shows the 400 MHz ¹H-NMR spectrum (in CDCl₃) of the compound of Formula 15, and FIG. 15 shows the 101 MHz ¹³C-NMR spectrum (in CD₃OD) of the compound of Formula 15.

¹H NMR (400 MHz, CDCl₃) δ=10.52 (s, 1H), 7.39-7.28 (m, 15H), 6.41 (s, 1H), 5.31 (s, 2H), 5.07 (s, 2H), 5.06 (s, 2H), 2.84 (t, J=7.9, 2H), 1.47 (m, 2H), 1.25 (m, 4H), 0.86 (t, J=7.3, 3H); ¹³C NMR (101 MHz, CDCl₃) δ=189.8, 167.4, 164.9, 160.1, 146.0, 135.5, 134.4, 128.7, 128.65, 128.6, 128.45, 128.35, 128.3, 128.2, 127.2, 127.0, 119.1, 116.7, 95.5, 70.9, 70.4, 67.3, 32.3, 31.2, 31.1, 22.4, 14.0; HRMS (ESI-TOF) m/z calculated for $C_{34}H_{35}O_5$ [M+H]⁺: 523.2484, found: 523.2480.

Example 1-9

Synthesis of Benzyl 4,6-Bis(Benzyloxy)-3-Hydroxy-2-Pentylbenzoate (16)

[Formula 16]

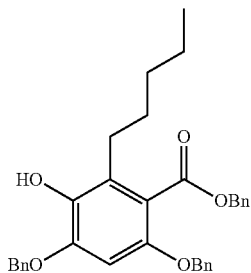

Benzyl 4,6-bis(benzyloxy)-3-formyl-2-pentylbenzoate (15) (10 g, 19.6 mmol) and 100 ml of MC were added to a dry round-bottom flask. mCPBA (8.5 g, 49 mmol) was precipitated in the reaction mixture at a temperature lower than 10° C. with rapid stirring. The reaction mixture was stirred at room temperature for 4 hours. TLC monitoring was performed. The reaction mixture was extracted with water, and then extracted three times with NaHCO₃. The organic layer was dried in vacuo, and the crude oil was dissolved again in 100 ml of MeOH. The MeOH mixture was precipitated in 125 ml of 10% KOH at 0° C. The reaction was terminated by addition of 6N HCl, and the MeOH was removed in a rotary evaporator. The residue was diluted with ethyl acetate. The mixture was separated into two layers, and the aqueous phase was extracted three times with ethyl acetate. The yield was 85%.

Figure 16:
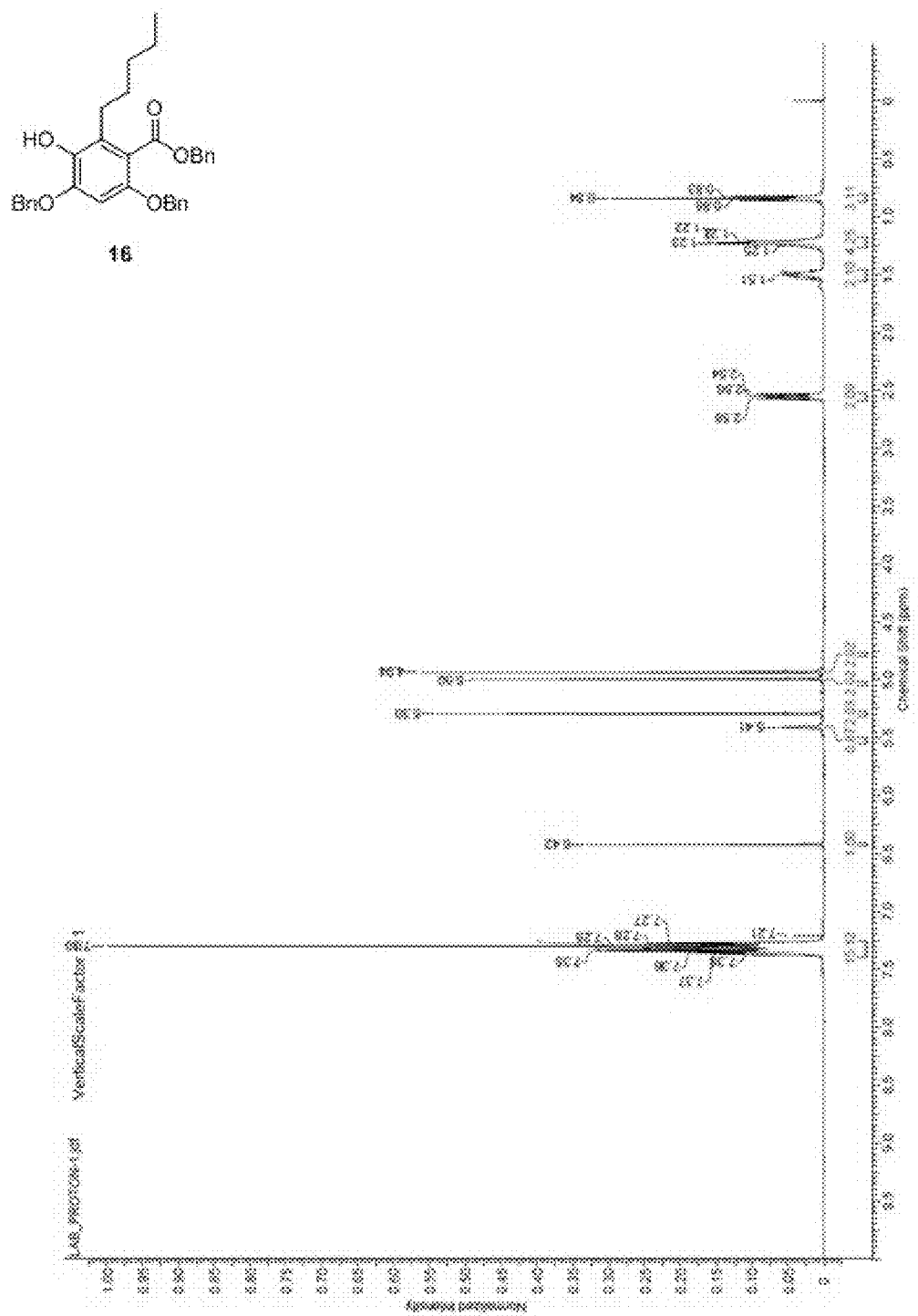
FIG. 16 is the 400 MHz $^1$H-NMR spectrum (in CD$_3$OD) of a compound of Formula 16 according to one example of the present invention.
Figure 17:
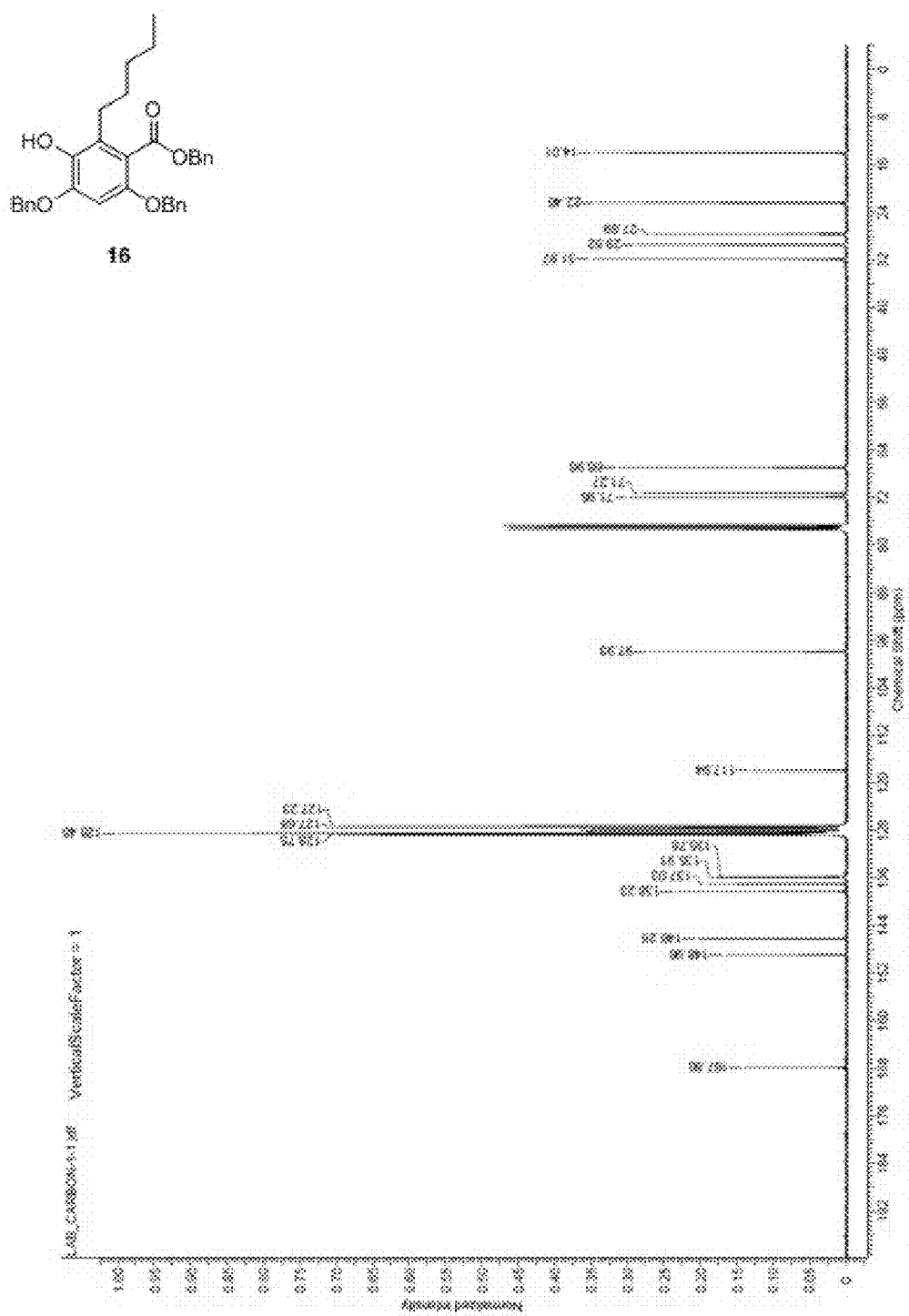
FIG. 17 is the 101 MHz $^{13}$C-NMR spectrum (in CD$_3$OD) of a compound of Formula 16 according to one example of the present invention.
Figure 18:
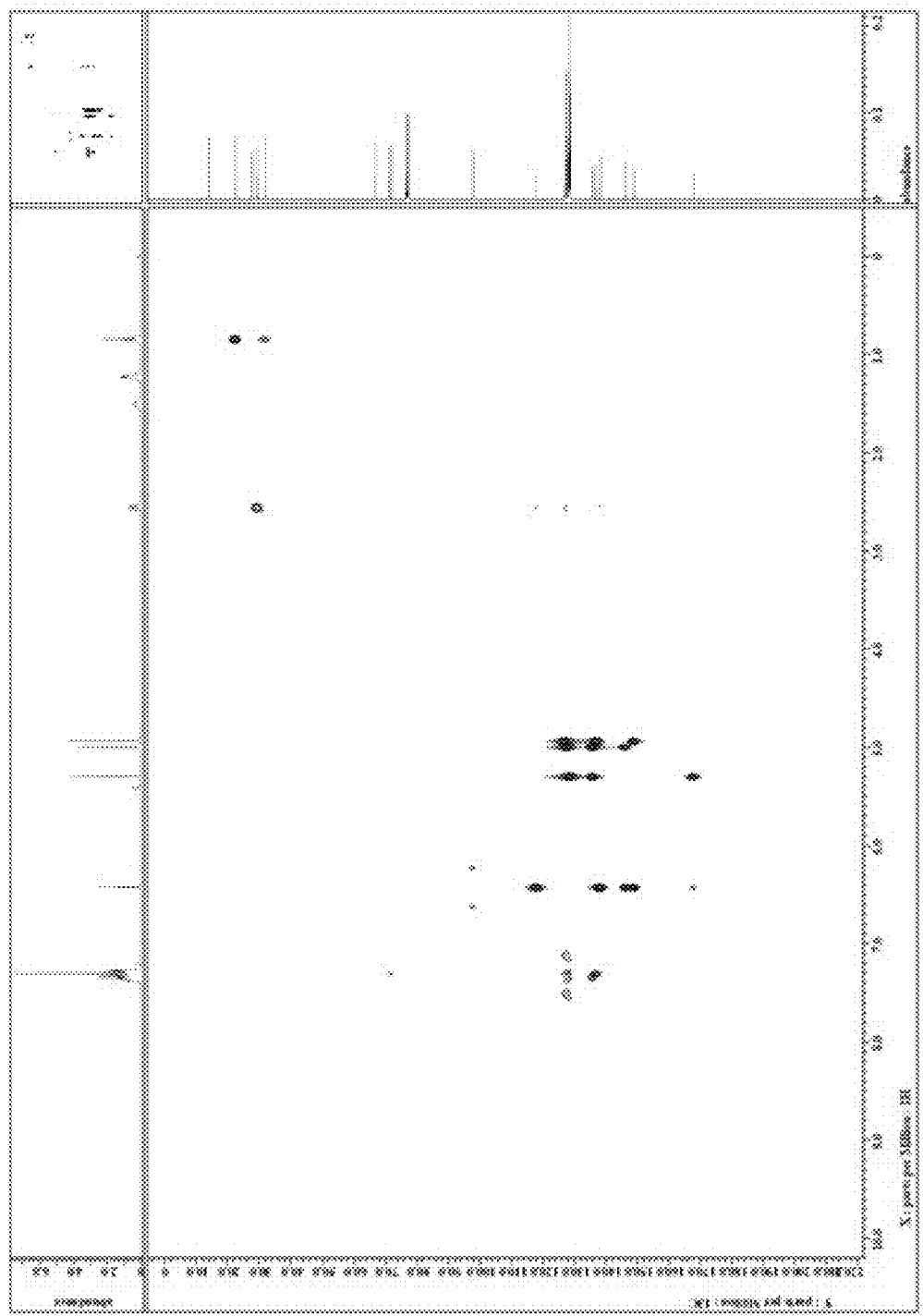
FIG. 18 is the HMBC spectrum (in CD$_3$OD) of a compound of Formula 16 according to one example of the present invention.

FIGS. 16, 17 and 18 show the 400 MHz ¹H-NMR spectrum (in CD₃OD), 101 MHz ¹³C-NMR spectrum (in CDCl₃) and HMBC spectrum (in CDCl₃) of the compound of Formula 16, respectively.

¹H NMR (400 MHz, CDCl₃) δ=7.38-7.27 (m, 15H), 6.42 (s, 1H), 5.30 (s, 2H), 5.00 (s, 2H), 4.94 (s, 2H) 2.56 (t, J=8.0, 2H), 1.51 (m, 2H), 1.22 (m, 4H), 0.84 (t, J=6.7, 3H); ¹³C NMR (101 MHz, CDCl₃) δ=167.8, 148.9, 146.2, 138.2, 137.0, 135.9, 135.8, 128.7, 128.6, 128.4, 128.1, 127.7, 127.6, 127.5, 127.2, 117.9, 98.9, 71.9, 71.3, 67.0, 31.9, 29.5, 27.6, 22.4, 14.0; HRMS (ESI-TOF) m/z calculated for $C_{34}H_{35}O_5$ [M+H]⁺: 511.2484, found: 511.2486.

Example 1-10

Synthesis of 2,4-Dihydroxyl-6-Pentylbenzaldehyde (18)

[Formula 18]

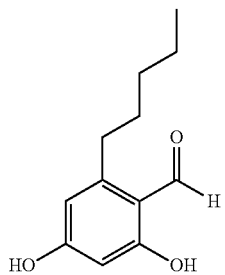

The starting material olivetol (19) (5 g, 27.7 mmol) was dissolved in 150 ml of DMF in a round-bottom flask. The solution was cooled to 0° C., and POCl$_3$ (3.9 ml, 41.6 mmol) was added slowly thereto over about 5 minutes. After stirring at 0° C. for 30 minutes, the mixture was warmed to room temperature and stirred for 8 hours. The reaction was terminated by addition of water, and the reaction mixture was extracted about 4 times with MC. The obtained organic layer was dried with Na$_2$SO$_4$, concentrated, and then purified by silica gel chromatography. The yield was 90%.

Figure 19:
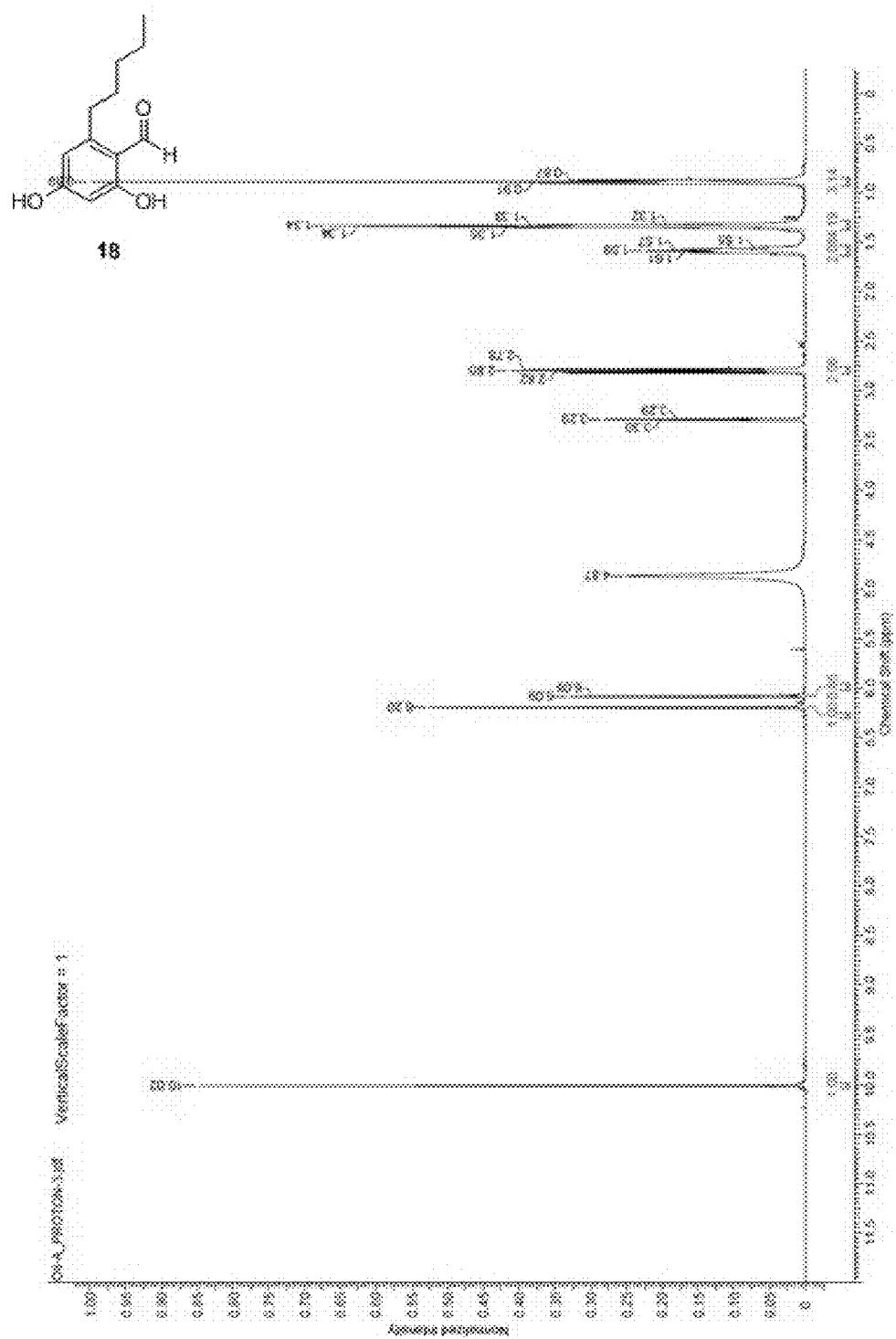
FIG. 19 is the 400 MHz $^1$H-NMR spectrum (in CD$_3$OD) of a compound of Formula 18 according to one example of the present invention.
Figure 20:
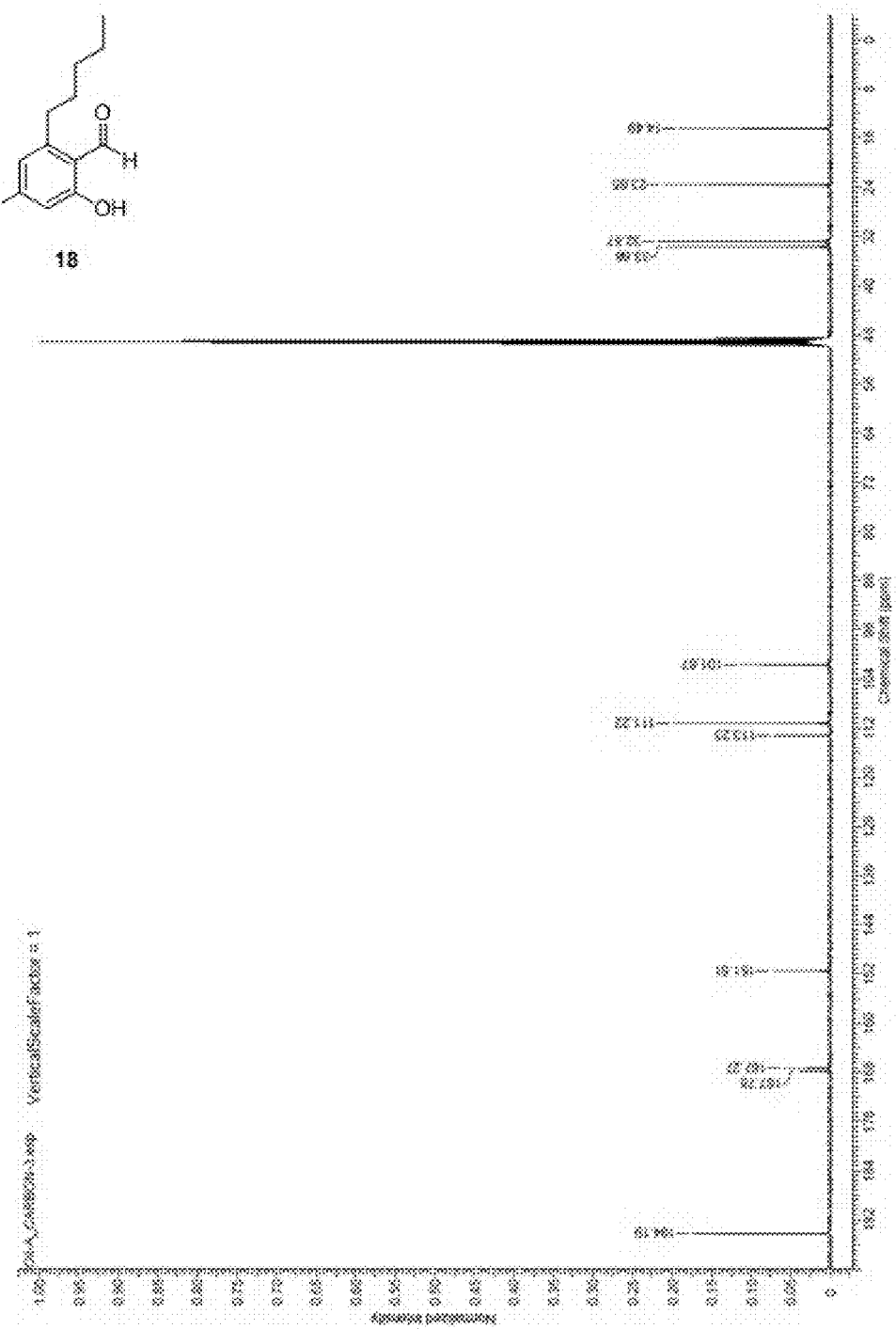
FIG. 20 is the 101 MHz $^{13}$C-NMR spectrum (in CD$_3$OD) of a compound of Formula 18 according to one example of the present invention.

FIG. 19 shows the 400 MHz $^1$H-NMR spectrum (in CD$_3$OD) of the compound of Formula 18, and FIG. 20 shows the 101 MHz $^{13}$C-NMR spectrum (in CD$_3$OD) of the compound of Formula 18.

$^1$H NMR (400 MHz, CD$_3$OD) δ=10.02 (s, 1H), 6.21 (s, 1H), 6.10 (d, J=2.4, 1H), 2.81 (t, J=7.3, 2H), 1.60 (m, 2H), 1.35 (m, 4H), 0.90 (t, J=6.7, 3H); $^{13}$C NMR (101 MHz, CD$_3$OD) δ=194.2, 167.8, 167.2, 151.5, 113.2, 111.2, 101.7, 33.7, 32.9, 32.8, 23.7, 14.5; HRMS (ESI-TOF) m/z calculated for C$_{12}$H$_{17}$O$_3$ [M+H]$^+$: 209.1178, found: 209.1175.

Example 1-11

Synthesis of 2,4-Dihydroxyl-6-Pentylbenzoic acid (19)

[Formula 19]

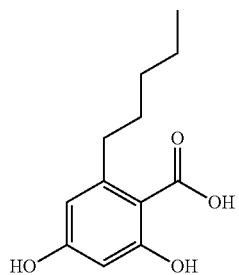

In a round-bottom flask equipped with a magnetic bar, compound (18) (5.3 g, 25.2 mmol) and NaH$_2$PO$_4$—H$_2$O (8.7 g, 63 mmol) were dissolved in a mixed solvent of DMSO (120 ml) and water (15 ml). The mixture was stirred at room temperature for about 12 hours. Saturated Na$_2$CO$_3$ was added to the mixture, followed by layer separation with ethyl acetate. The aqueous layer was adjusted to a pH of 1 by addition of HCl. Extraction was performed three times with ethyl acetate. The obtained organic layer was dried with anhydrous Na$_2$SO$_4$, concentrated, and then purified by C18 chromatography. The yield was 78%.

Figure 21:
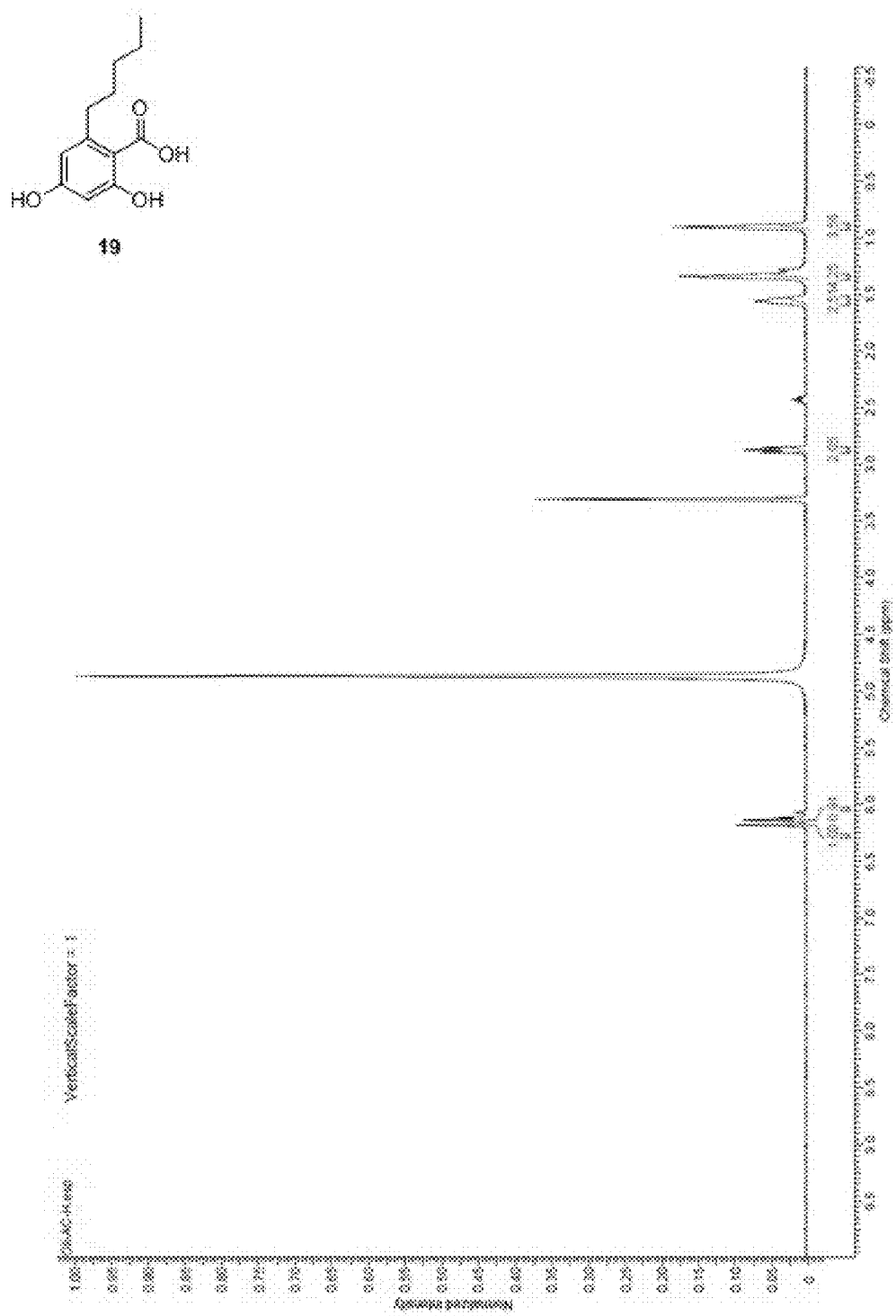
FIG. 21 is the 400 MHz $^1$H-NMR spectrum (in CD$_3$OD) of a compound of Formula 19 according to one example of the present invention.
Figure 22:
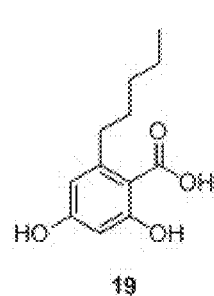
FIG. 22 is the 101 MHz $^{13}$C-NMR spectrum (in CD$_3$OD) of a compound of Formula 19 according to one example of the present invention.
Figure 22:
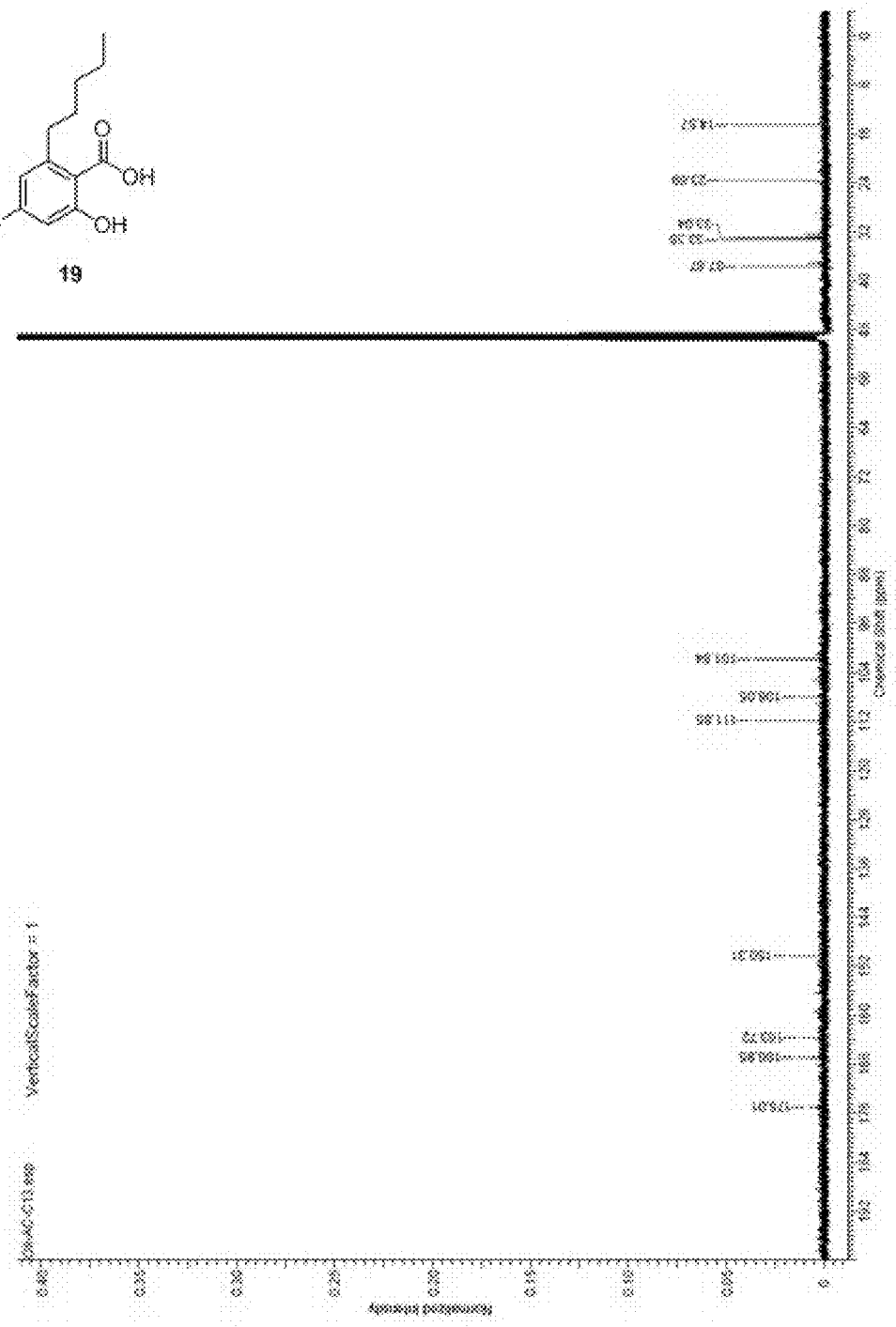

FIG. 21 shows the 400 MHz $^1$H-NMR spectrum (in CD$_3$OD) of the compound of Formula 19, and FIG. 22 shows the 101 MHz $^{13}$C-NMR spectrum (in CD$_3$OD) of the compound of Formula 19.

$^1$H NMR (400 MHz, CD$_3$OD) δ=6.15 (s, 1H), 6.11 (s, 1H), 2.84 (t, J=7.6, 2H), 1.53 (m, 2H), 1.31 (m, 4H), 0.87 (m, 3H) $^{13}$C NMR (101 MHz, CD$_3$OD) δ=173.4, 165.3, 162.1, 148.7, 110.2, 106.4, 100.2, 36.1, 31.7, 31.4, 22.1, 13.0; HRMS (ESI-TOF) m/z calculated for C$_{12}$H$_{17}$O$_4$ [M+H]$^+$: 225.1127, found: 225.1117.

Example 1-12

Synthesis of Benzyl 4,6-Bis(Benzyloxy)-3-((1-Butyl-1-Hydroxy-6-Methoxy-3-Oxo-1,3-Dihydroisobenzofuran-4-Yl)Oxy)-2-Pentylbenzoate (22)

[Formula 22]

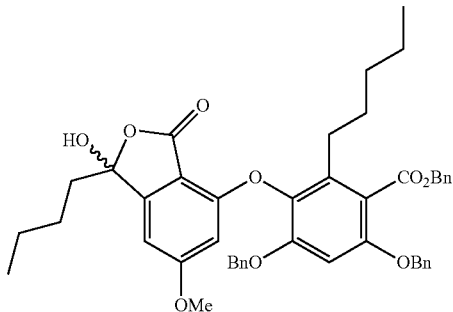

CuI (53 mg, 0.28 mmol), picolinic acid (53 mg, 0.55 mmol), 2-iodo-4-methoxy-6-pentanoylbenzoic acid (10) (500 mg, 1.38 mmol), benzyl 4,6-bis(benzyloxy)-3-hydroxy-2-pentylbenzoate (16) (704 mg, 1.38 mmol) and K$_3$PO$_4$ (880 mg, 4.14 mmol) were added to a dried sealed tube while stirring with a magnetic bar. The tube was evacuated and filled again with argon. Evacuation and filling was repeated two more times. Under a counter flow of argon, 20 ml of DMSO was introduced by a syringe. The tube was left to stand in an oil bath preheated to 110° C. and the reaction mixture was stirred vigorously for 12 hours. The reaction mixture was cooled to room temperature. After addition of ethyl acetate and H$_2$O, the mixture was stirred. The organic layer was separated and the aqueous layer was extracted twice with ethyl acetate. The organic layer was dried with Na$_2$SO$_4$ and filtered through a silica gel pad. The filtrate was concentrated, and the resulting residue was purified by silica gel chromatography. The yield was 58%.

Figure 27:
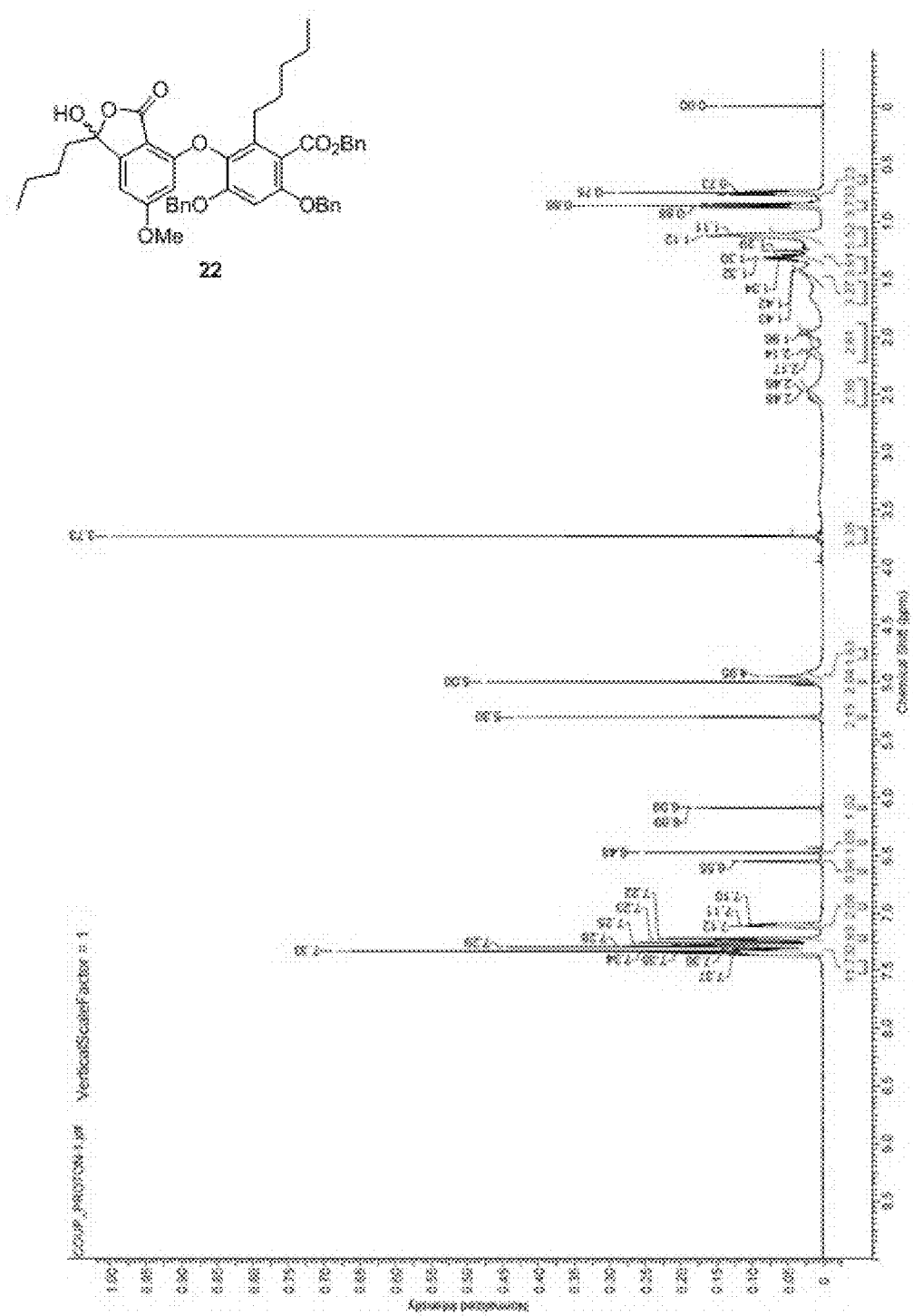
FIG. 27 is the 400 MHz $^1$H-NMR spectrum (in CD$_3$OD) of a compound of Formula 22 according to one example of the present invention.
Figure 28:
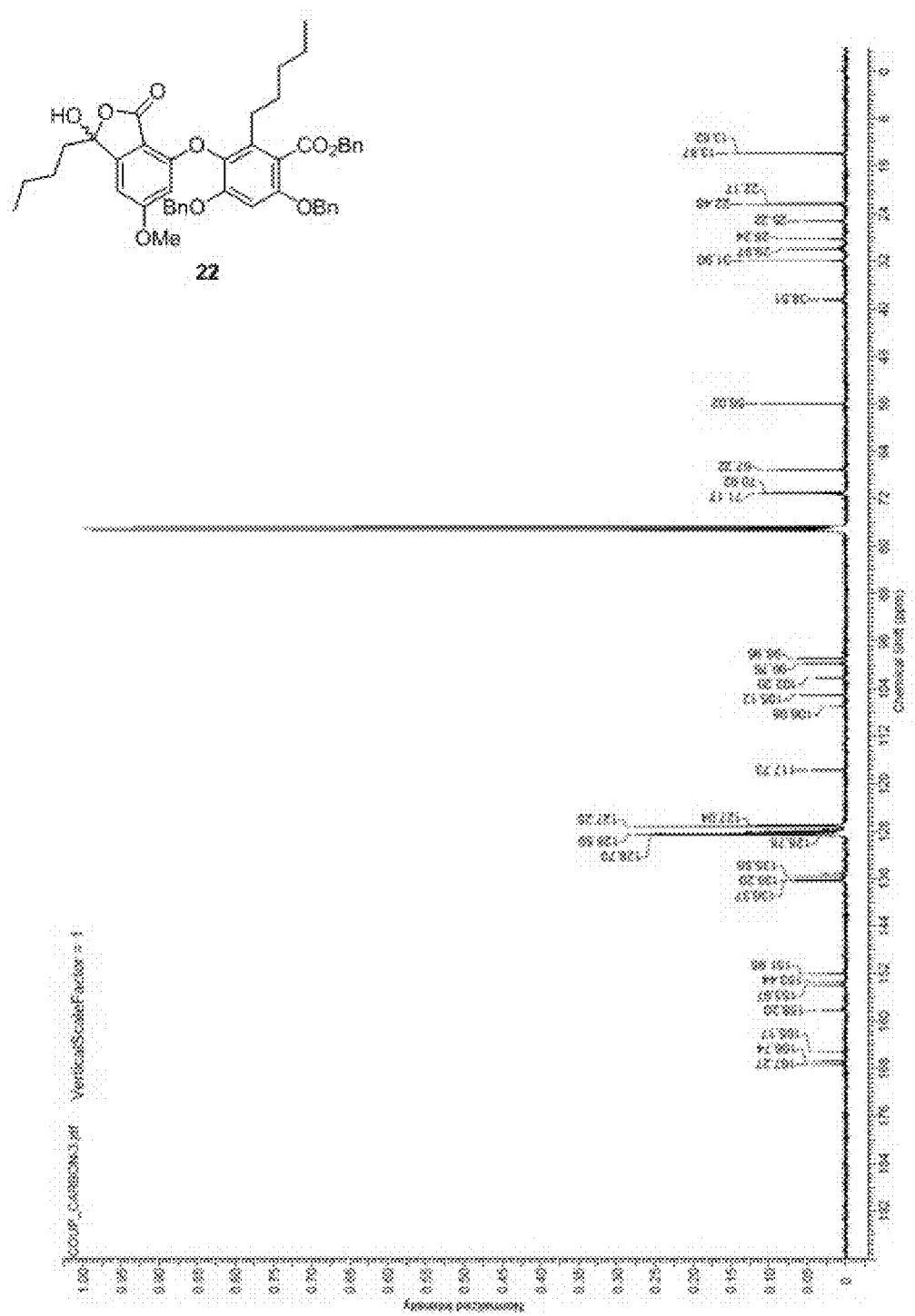
FIG. 28 is the 101 MHz $^{13}$C-NMR (in CD$_3$OD) of a compound of Formula 22 according to one example of the present invention.

FIG. 27 shows the 400 MHz $^1$H-NMR spectrum (in CD$_3$OD) of the compound of Formula 22, and FIG. 28 shows the 101 MHz $^{13}$C-NMR (in CD$_3$OD) of the compound of Formula 22.

$^1$H NMR (400 MHz, CDCl$_3$) δ=7.29 (m, 8H), 7.11 (m, 2H), 6.55 (d, J=1.8, 1H), 6.48 (s, 1H), 6.09 (d J=1.8, 1H), 5.30 (s, 2H), 5.00 (s, 2H), 4.95 (s, 2H), 3.73 (s, 3H), 2.48 (m,

2H), 2.06 (m, 2H), 1.31 (m, 6H), 1.13 (m, 4H), 0.86 (t, J=7.3, 3H), 0.75 (t, J=6.7, 3H); $^{13}$C NMR (101 MHz, CDCl$_3$) δ=167.2, 166.7, 165.1, 158.2, 153.9, 153.4, 151.9, 136.3, 136.1, 135.5, 135.0, 128.7, 128.6, 128.5, 128.4, 128.2, 128.1, 128.0, 127.2, 127.0, 117.7, 106.9, 105.0, 102.1, 99.7, 98.9, 71.1, 71.0, 67.2, 56.0, 38.5, 31.9, 29.9, 28.2, 25.2, 22.4, 22.1, 13.8, 13.7; HRMS (ESI-TOF) m/z calculated for C$_{46}$H$_{49}$O$_9$ [M+H]$^+$: 745.3377, found: 745.3374.

Example 1-13

Synthesis of Lobarin (3)

[Formula 3]

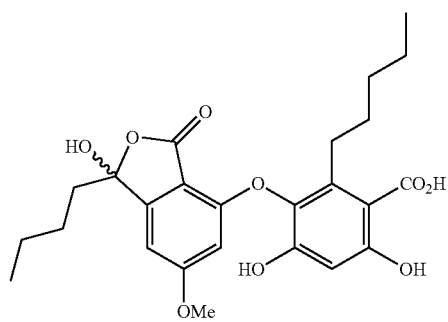

To a round-bottom flask filled with benzyl 4,6-bis (benzyloxy)-3-((1-butyl-1-hydroxy-6-methoxy-3-oxo-1,3-dihydroisobenzofuran-4-yl)oxy)-2-pentylbenzoate (22) (100 mg, 0.211 mmol) in 20 ml of MeOH, palladium (10%, 10 ml) on carbon was added. Under a hydrogen atmosphere, the mixture was stirred for 12 hours. The reaction mixture was filtered through a silica gel pad. The solvent was removed by concentration under reduced pressure, and the crude mixture was purified by C18 chromatography. The yield was 95%.

Figure 29:
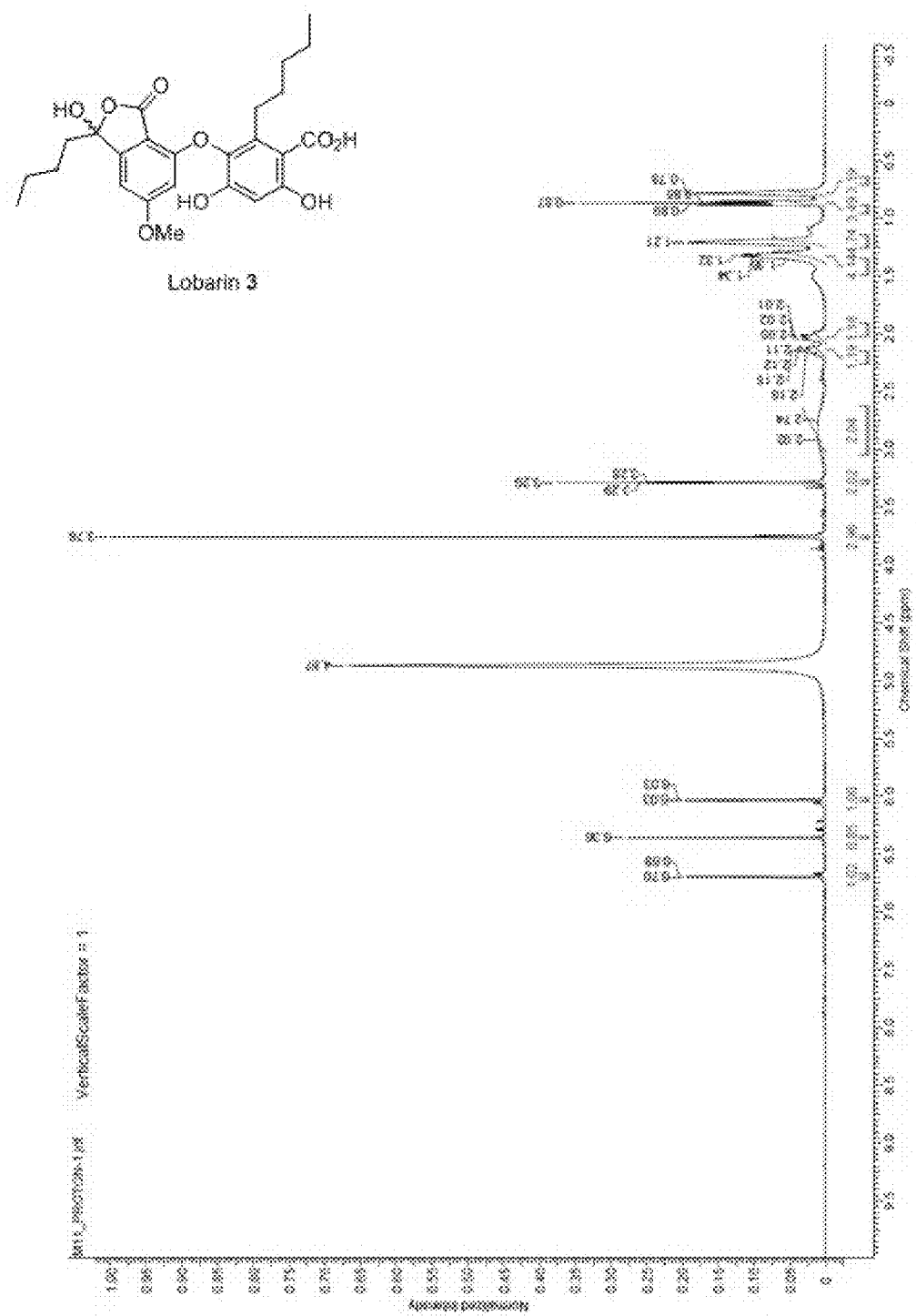
FIG. 29 is the 400 MHz $^1$H-NMR spectrum (in CD$_3$OD) of lobarin (Formula 3) according to one example of the present invention.
Figure 30:
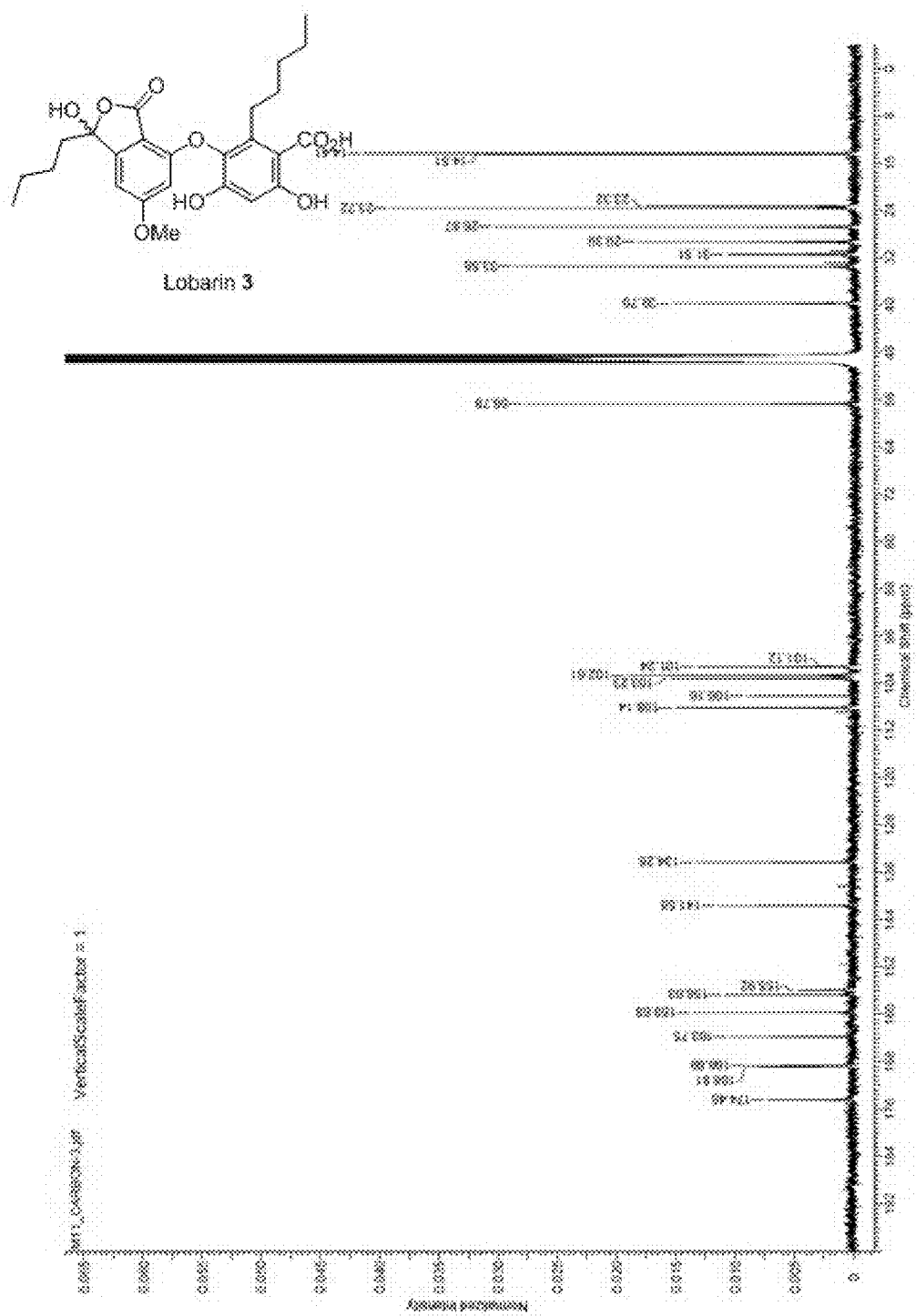
FIG. 30 is the 101 MHz $^{13}$C-NMR spectrum (in CD$_3$OD) of lobarin (Formula 3) according to one example of the present invention.

FIG. 29 shows the 400 MHz $^1$H-NMR spectrum (in CD$_3$OD) of lobarin (Formula 3), and FIG. 30 shows the 101 MHz $^{13}$C-NMR spectrum (in CD$_3$OD) of lobarin (Formula 3).

$^1$H NMR (400 MHz, CD$_3$OD) δ=6.71 (d, J=1.8, 1H), 6.37 (s, 1H), 6.04 (d, J=1.8, 1H), 3.77 (s, 3H), 2.10 (m, 2H), 1.54 (m, 2H), 1.34 (m, 4H), 1.22 (m, 4H), 1.11 (m, 2H), 0.88 (t, J=6.7, 3H), 0.80 (m, 3H); $^{13}$C NMR (101 MHz, CD$_3$OD) δ=174.5, 168.8, 168.7, 163.7, 156.7, 156.6, 155.9, 141.6, 134.3, 108.1, 106.2, 103.2, 102.6, 101.2, 101.1, 56.8, 39.8, 33.6, 31.5, 29.4, 26.9, 23.7, 23.3, 14.5, 14.4; HRMS (ESI-TOF) m/z calculated for C$_{25}$H$_{31}$O$_9$ [M+H]$^+$: 475.1968, found: 475.1960.

Example 2-1

Synthesis of Benzyl 3-((1-Butyl-1-Hydroxy-6-Methoxy-3-Oxo-1,3-Dihydroisobenzofuran-4-Yl)Oxy)-4,6-Dihydroxy-2-Pentylbenzoate (23)

[Formula 23]

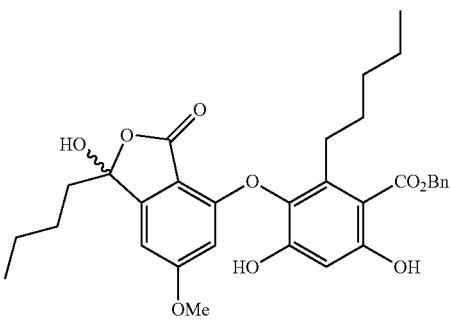

Lobarin (3) (50 mg, 0.11 mmol) was added to a round-bottom flask and dissolved in 10 ml of methanol, and then cesium carbonate (17 mg, 0.053 mmol) was added thereto, followed by stirring for 10 minutes. Next, water was completely removed by concentration under reduced pressure. The reaction mixture was dissolved in 3 ml of DMF, and then benzyl bromide (14 μl, 0.121 mmol) was added thereto, followed by stirring for 18 hours. After completion of the reaction, the white solid was filtered out, and the crude mixture was purified by C18 chromatography. The yield was 83%.

Figure 31:
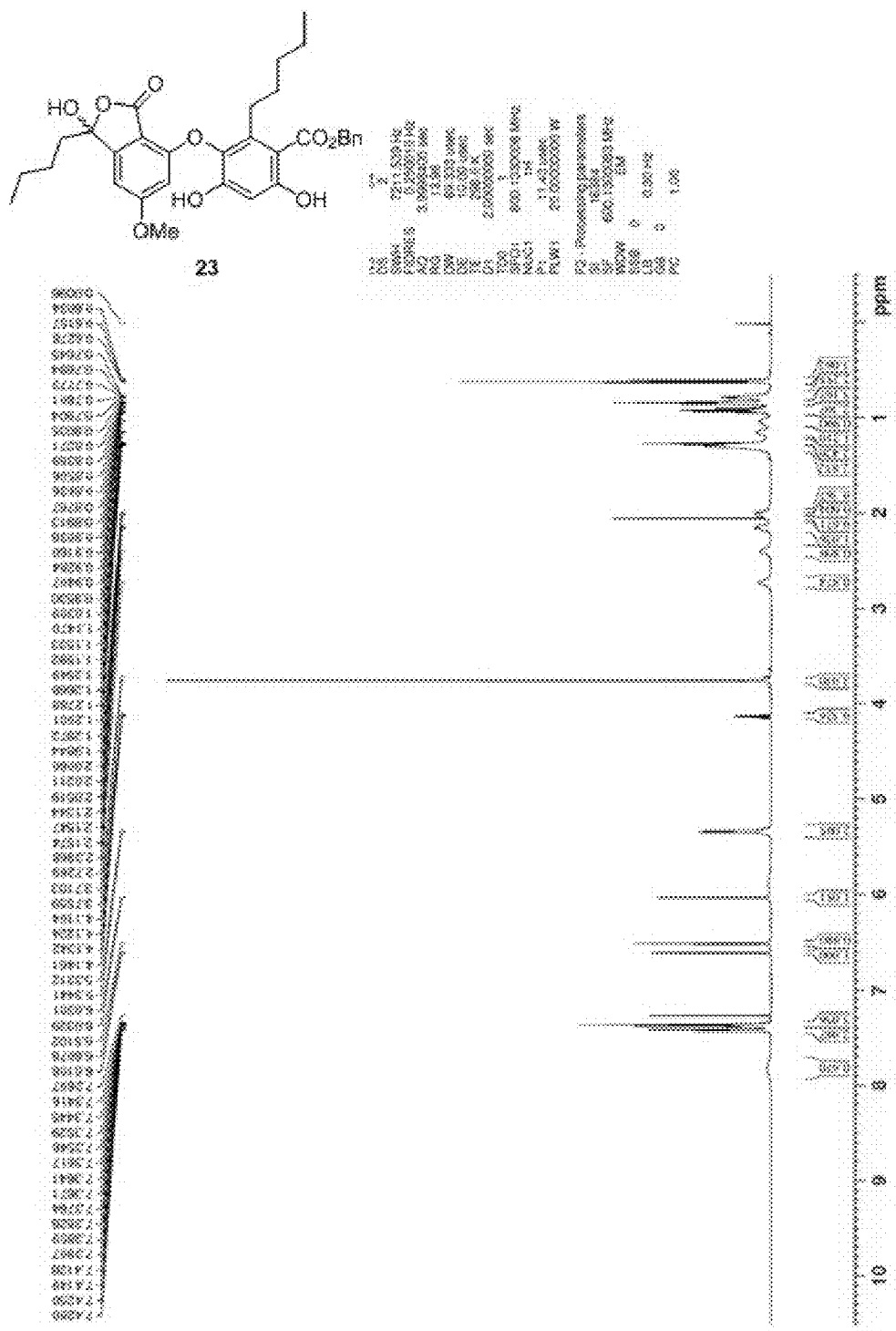
FIG. 31 is the 400 MHz $^1$H-NMR spectrum (in CD$_3$OD) of a compound of Formula 23 according to one example of the present invention.
Figure 32:
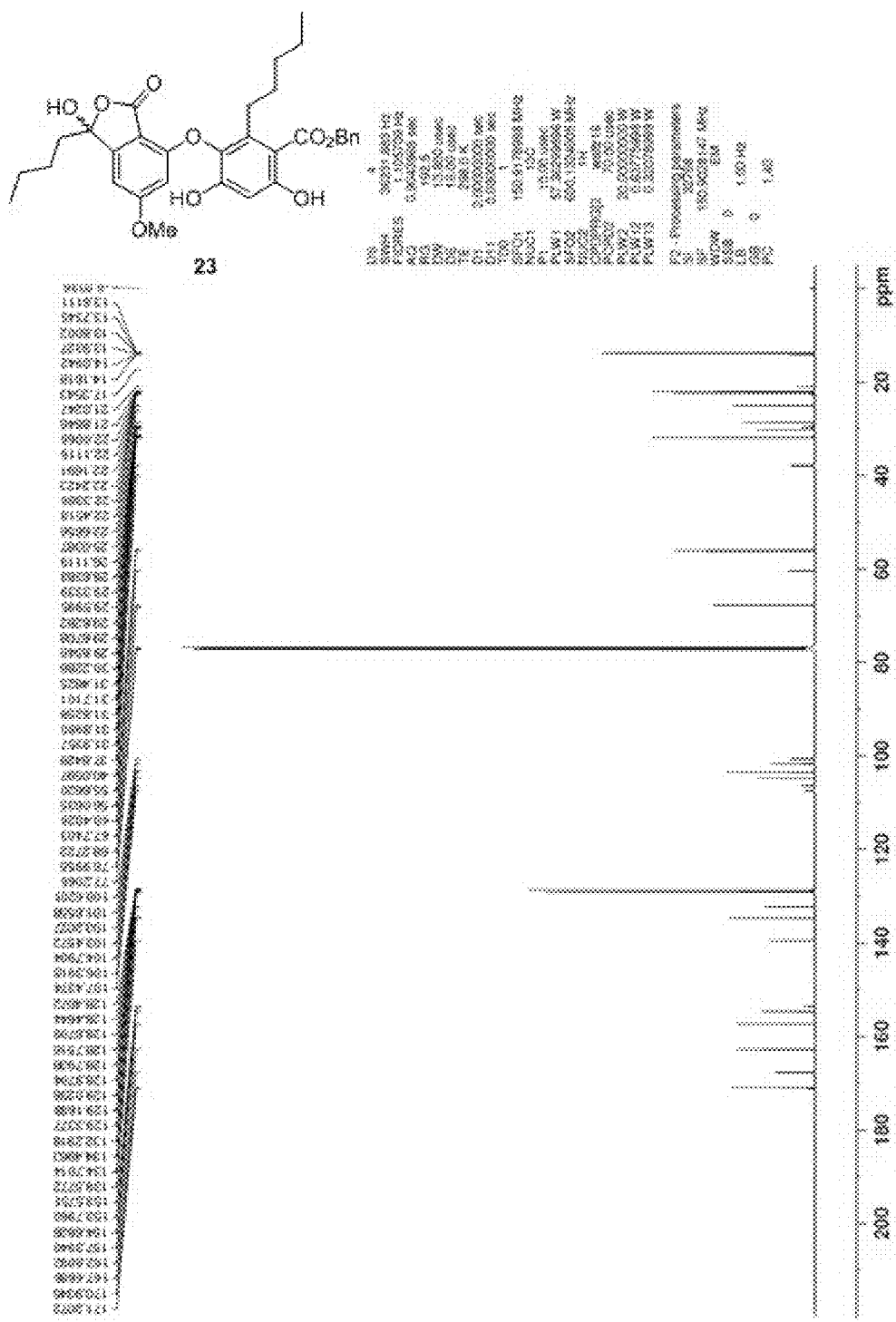
FIG. 32 is the 101 MHz $^{13}$C-NMR spectrum (in CD$_3$OD) of a compound of Formula 24 according to one example of the present invention.

FIG. 31 shows the 600 MHz $^1$H-NMR spectrum (in CD$_3$OD) of the compound of Formula 23, and FIG. 32 shows the 150 MHz $^{13}$C-NMR spectrum (in CD$_3$OD) of the compound of Formula 23.

Example 2-2

Synthesis of Lobaric Acid (1)

[Formula 1]

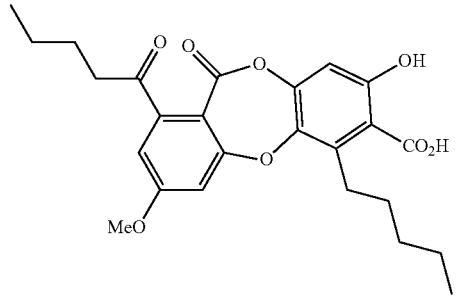

In a dried round-bottom flask, DMAP (15 mg, 0.133 mmol) and compound 23 were dissolved in 10 ml of MC. To the reaction solution, a solution of DCC (24 mg, 0.117 mmol) in 10 ml of MC was added slowly over about 30 minutes. After completion of the addition, stirring was performed for 12 hours. The mixture was concentrated under reduced pressure, and then purified by C18 chromatography. The yield was 78%. The obtained lactone compound (45 mg, 0.082 mmol) was dissolved in 10 ml of methanol, and then palladium (10%, 4.5 mg) on carbon was added thereto. Under a hydrogen atmosphere, the mixture was stirred for 12 hours. The reaction mixture was filtered through a silica gel pad. The solvent was removed by concentration under reduced pressure, and the crude mixture was purified by C18 chromatography. The yield was 90%.

Figure 33:
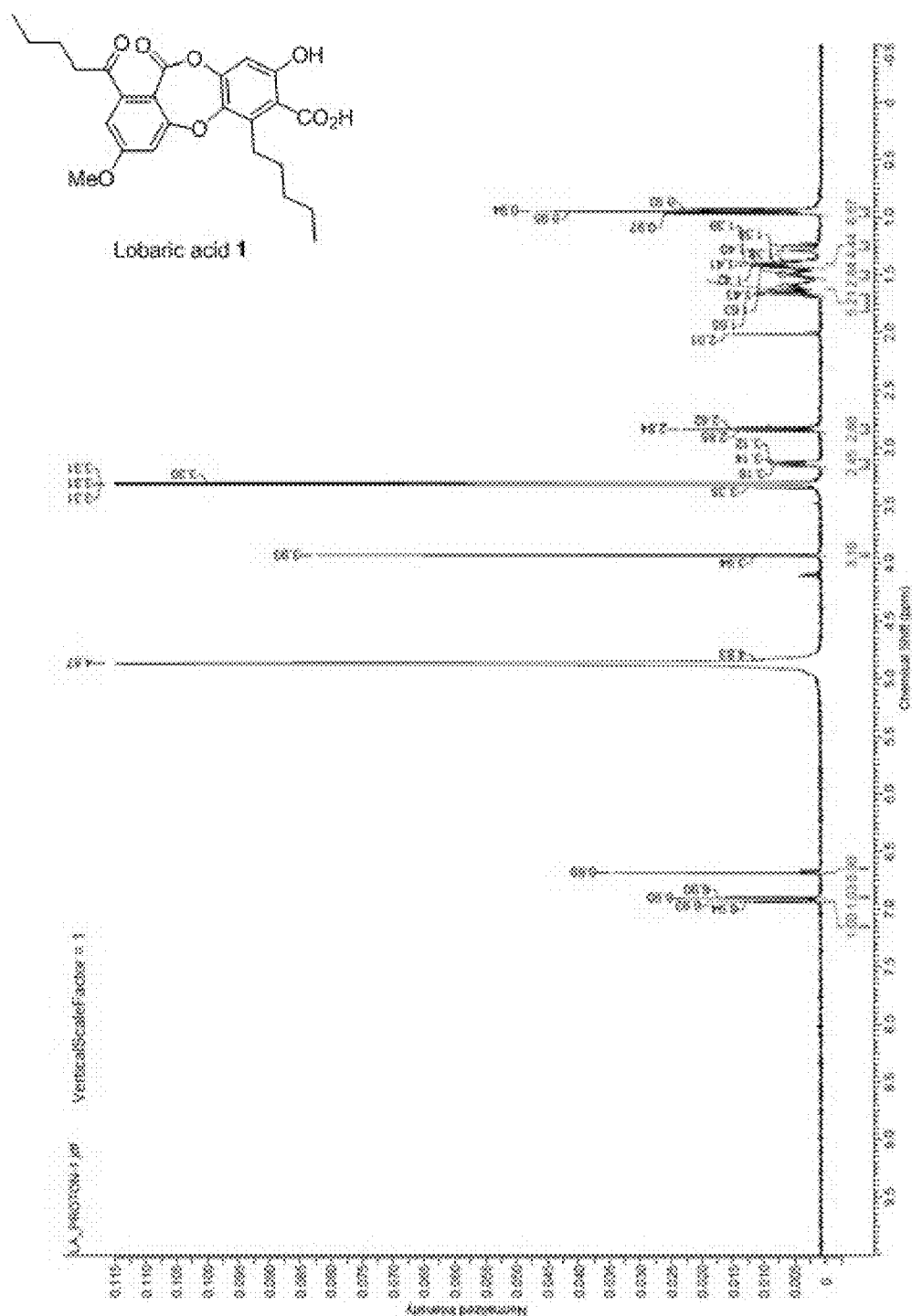
FIG. 33 is the 400 MHz $^1$H-NMR spectrum (in CD$_3$OD) of lobaric acid (Formula 1) according to one example of the present invention.
Figure 34:
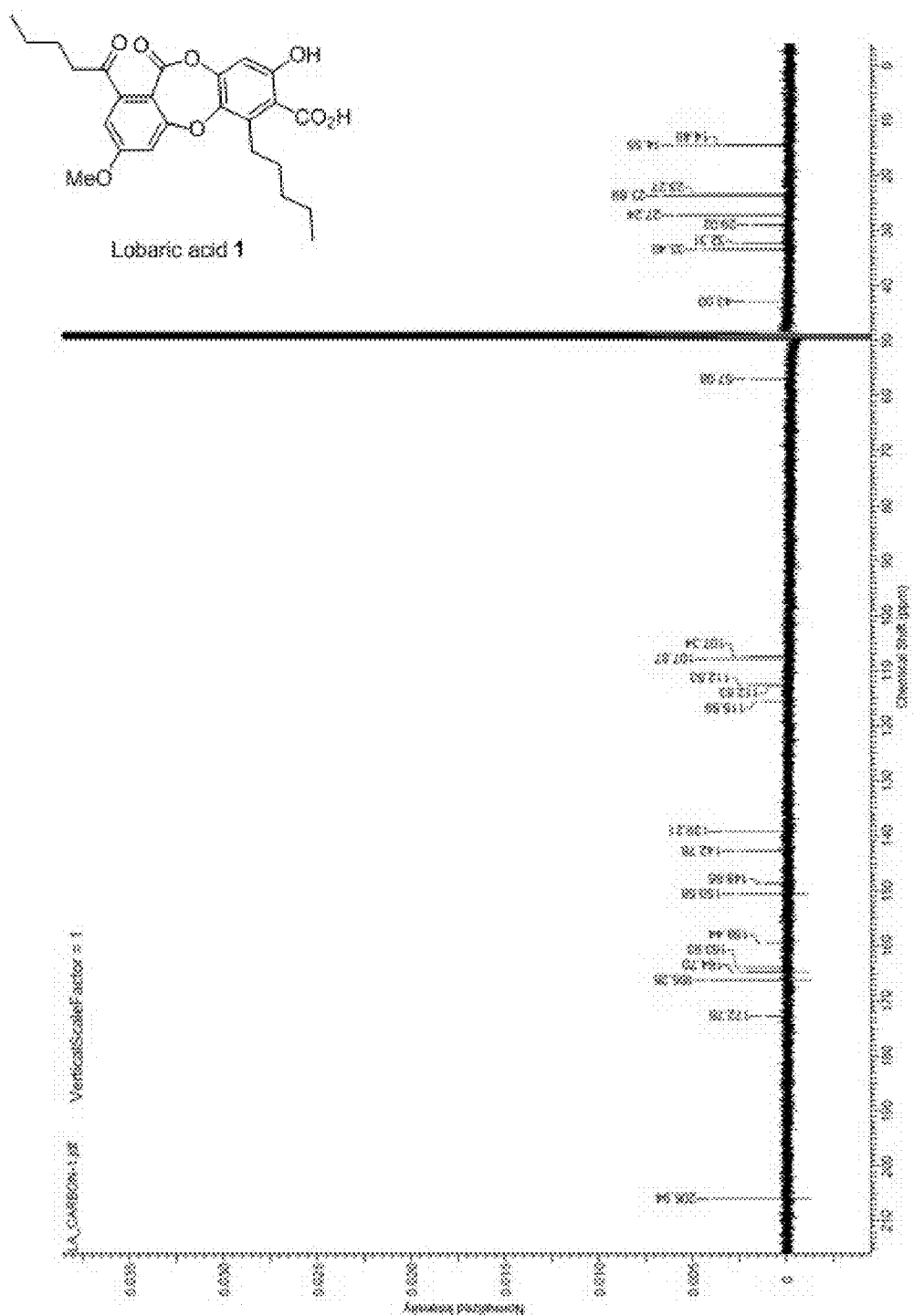
FIG. 34 is the 101 MHz $^{13}$C-NMR spectrum (in CD$_3$OD) of lobaric acid (Formula 1) according to one example of the present invention.

FIG. 33 shows the 400 MHz $^1$H-NMR spectrum (in $CD_3OD$) of lobaric acid (Formula 1), and FIG. 34 shows the 101 MHz $^{13}$C-NMR spectrum (in $CD_3OD$) of lobaric acid (Formula 1).

$^1$H NMR (400 MHz, $CD_3OD$) δ=6.92 (d, J=2.4, 1H), 6.89 (d, J=2.4, 1H), 6.68 (s, 1H), 3.92 (s, 3H), 3.13 (m, 2H), 2.82 (t, J=7.3, 2H), 1.57 (m, 3H), 1.48 (m, 2H), 1.41 (m, 5H), 0.94 (m, 6H); $^{13}$C NMR (101 MHz, $CD_3OD$) δ=205.9, 172.8, 166.3, 164.5, 163.9, 159.4, 150.6, 148.6, 142.8, 139.2, 115.6, 112.8, 112.5, 107.9, 107.3, 57.1, 43.0, 33.5, 32.3, 29.0, 27.2, 23.7, 23.3, 14.5, 14.4; HRMS (ESI-TOF) m/z calculated for $C_{25}H_{29}O_8$ $[M+H]^+$: 457.1862, found: 457.1846.

Example 3

Synthesis of Compound of Formula 2

Example 3-1

Synthesis of Methyllobarin (3) from Lobaric Acid

[Formula 2]

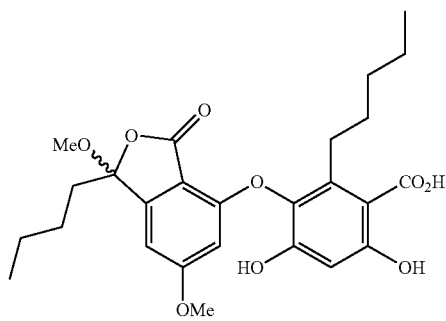

2

Lobaric acid (1) (100 mg, 0.22 mmol) was dried sufficiently, and then added to a dried round-bottom flask and dissolved in 100 ml of anhydrous methanol. Sodium methoxide (14 mg, 0.26 mmol) was added slowly thereto, followed by stirring at room temperature for 2 hours. The reaction was terminated by addition of 1N HCl, followed by layer separation with ethyl acetate. The organic layer was concentrated under reduced pressure, and the crude mixture was purified by C18 chromatography. The yield was 91%.

Figure 35:
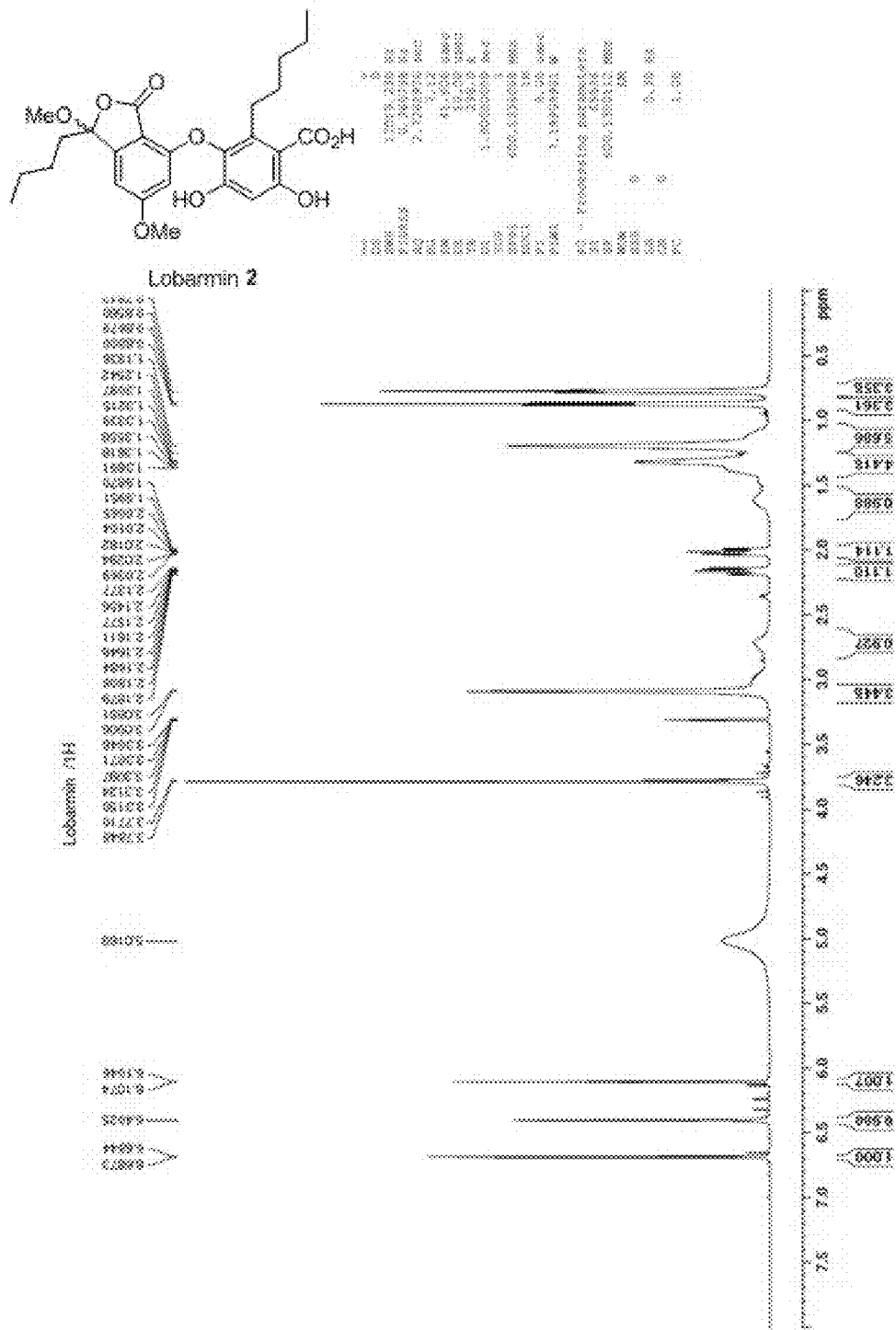
FIG. 35 is the 600 MHz $^1$H-NMR spectrum (in CD$_3$OD) of methyllobarin (Formula 2) according to one example of the present invention.
Figure 36:
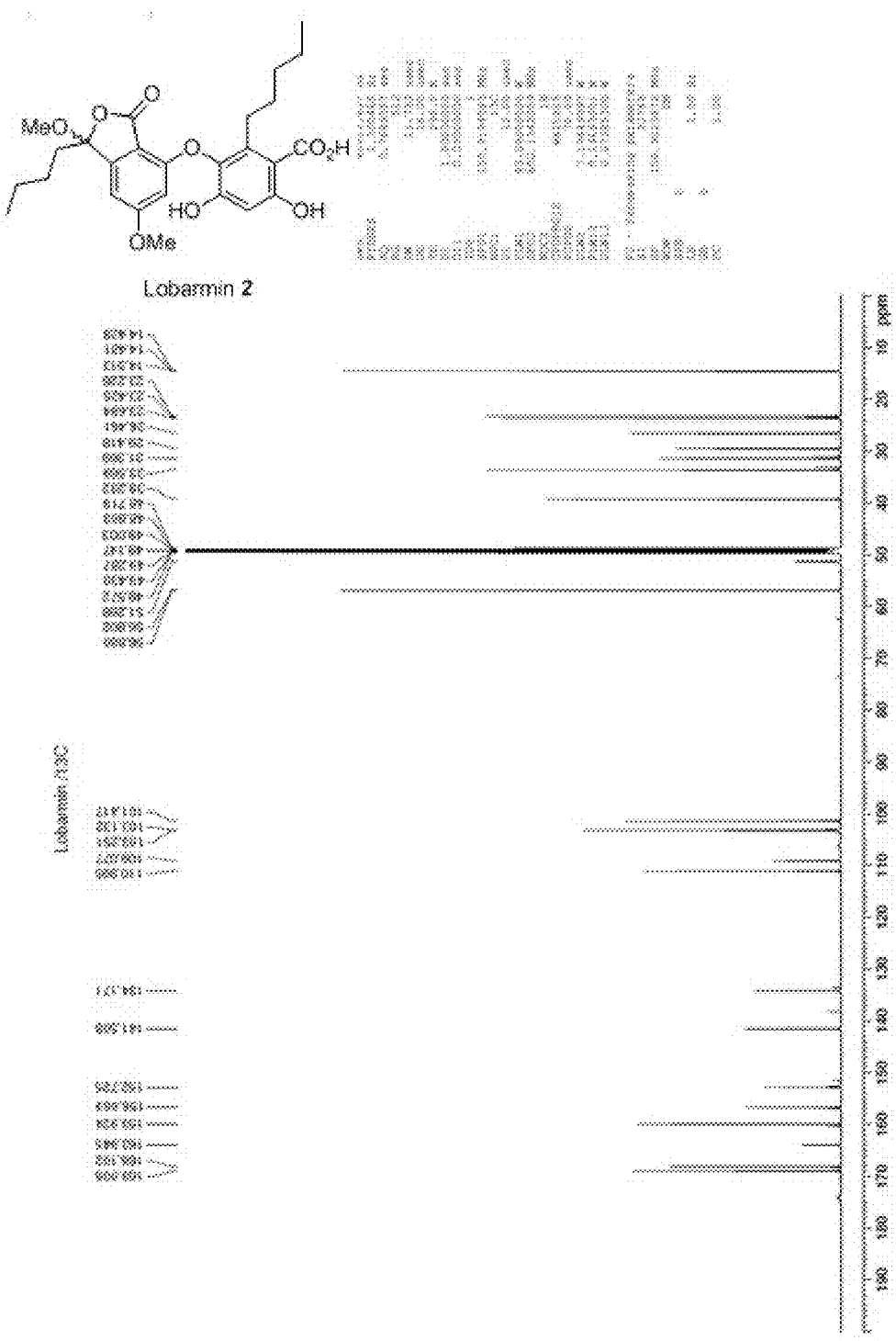
FIG. 36 is the 150 MHz $^{13}$C-NMR spectrum (in CD$_3$OD) of methyllobarin (Formula 2) according to one example of the present invention.

FIG. 35 shows the 400 MHz $^1$H-NMR spectrum (in $CD_3OD$) of methyllobarin (Formula 2), and FIG. 36 shows the 150 MHz $^{13}$C-NMR spectrum (in $CD_3OD$) of methyllobarin (Formula 2).

$^1$H NMR (600 MHz, $CD_3OD$) δ=6.68 (d, 1H), 6.40 (s, 1H), 6.10 (d, J=1.7, 1H), 3.78 (s, 3H), 2.16 (m, 1H), 2.01 (m, 1H), 1.62 (m, 1H), 1.37 (m, 5H), 1.19 (m, 6H), 0.87 (t, J=7.3, 3H), 0.77 (t, J=7.0, 3H); $^{13}$C NMR (151 MHz, $CD_3OD$) δ=169.0, 168.1, 163.9, 159.9, 156.7, 141.5, 134.1, 111.0, 109.1, 106.1, 103.3, 103.1, 101.4, 56.9, 56.8, 39.2, 33.6, 31.4, 29.4, 26.5, 23.7, 23.2, 14.5, 14.4; HRMS (ESI-TOF) m/z calculated for $C_{26}H_{33}O_9$ $[M+H]^+$: 489.2124, found: 489.2119.

Example 3-2

Synthesis of Lobarin (3) from Lobaric Acid

[Formula 3]

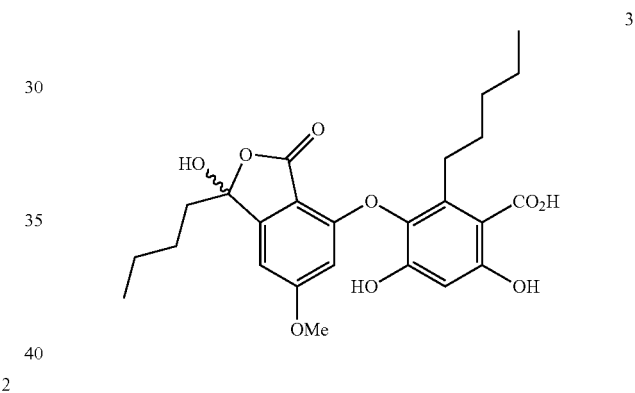

3

The extract lobaric acid (1) (100 mg, 0.22 mmol) was placed in a round-bottom flask and dissolved in 100 ml of MeOH. 10 ml of 1N NaOH was added thereto, followed by stirring at room temperature for 2 hours. MeOH was removed by concentration under reduced pressure, and the residue was adjusted to a pH of 2 to 3 by addition of 1N HCl. After layer separation with ethyl acetate, the organic layer was concentrated under reduced pressure. The crude mixture was purified by C18 chromatography. The yield was 93%.

FIG. 29 shows the 400 MHz $^1$H-NMR spectrum (in $CD_3OD$) of lobarin (Formula 3), and FIG. 30 shows the 101 MHz $^{13}$C-NMR spectrum (in $CD_3OD$) of lobarin (Formula 3).

$^1$H NMR (400 MHz, $CD_3OD$) δ=6.71 (d, 1H), 6.37 (s, 1H), 6.04 (d, J=1.8, 1H), 3.77 (s, 3H), 2.10 (m, 2H), 1.54 (m, 2H), 1.34 (m, 4H), 1.22 (m, 4H), 1.11 (m, 2H), 0.88 (t, J=6.7, 3H), 0.80 (m, 3H); $^{13}$C NMR (101 MHz, $CD_3OD$) δ=174.5, 168.8, 168.7, 163.7, 156.7, 156.6, 155.9, 141.6, 134.3, 108.1, 106.2, 103.2, 102.6, 101.2, 101.1, 56.8, 39.8, 33.6, 31.5, 29.4, 26.9, 23.7, 23.3, 14.5, 14.4; HRMS (ESI-TOF) m/z calculated for $C_{25}H_{31}O_9$ $[M+H]^+$: 475.1968, found: 475.1960.

Example 3-3

Synthesis of Lobastin (4) from Lobaric Acid

[Formula 4]

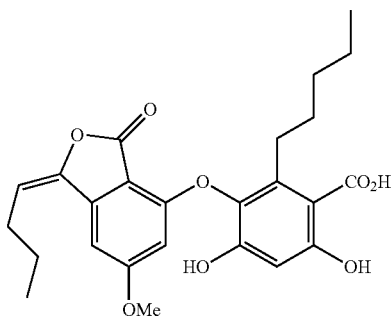

4

The extract lobaric acid (1) (100 mg, 0.22 mmol) was dried completely, and then added to a dried round-bottom flask and dissolved in 25 ml of anhydrous DMF. NaHMDS (48 mg, 0.26 mmol) was added slowly thereto, followed by stirring at room temperature for 2 hours. The reaction was terminated by addition of 1N HCl, followed by layer separation with ethyl acetate. The organic layer was concentrated under reduced pressure, and the crude mixture was purified by C18 chromatography. The yield was 85%.

Figure 37:
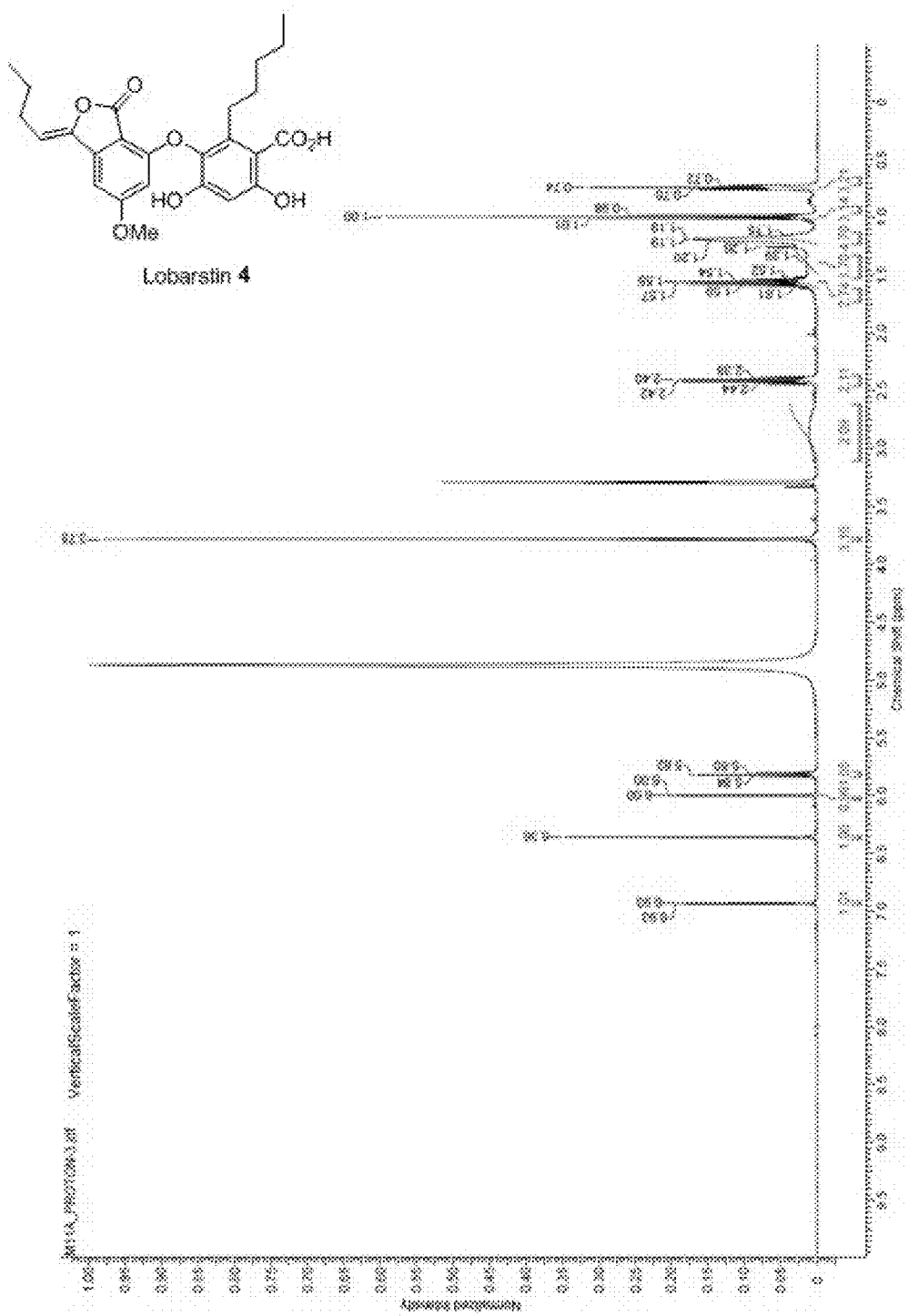
FIG. 37 is the 400 MHz $^1$H-NMR spectrum (in CD$_3$OD) of lobastin (Formula 4) according to one example of the present invention.
Figure 38:
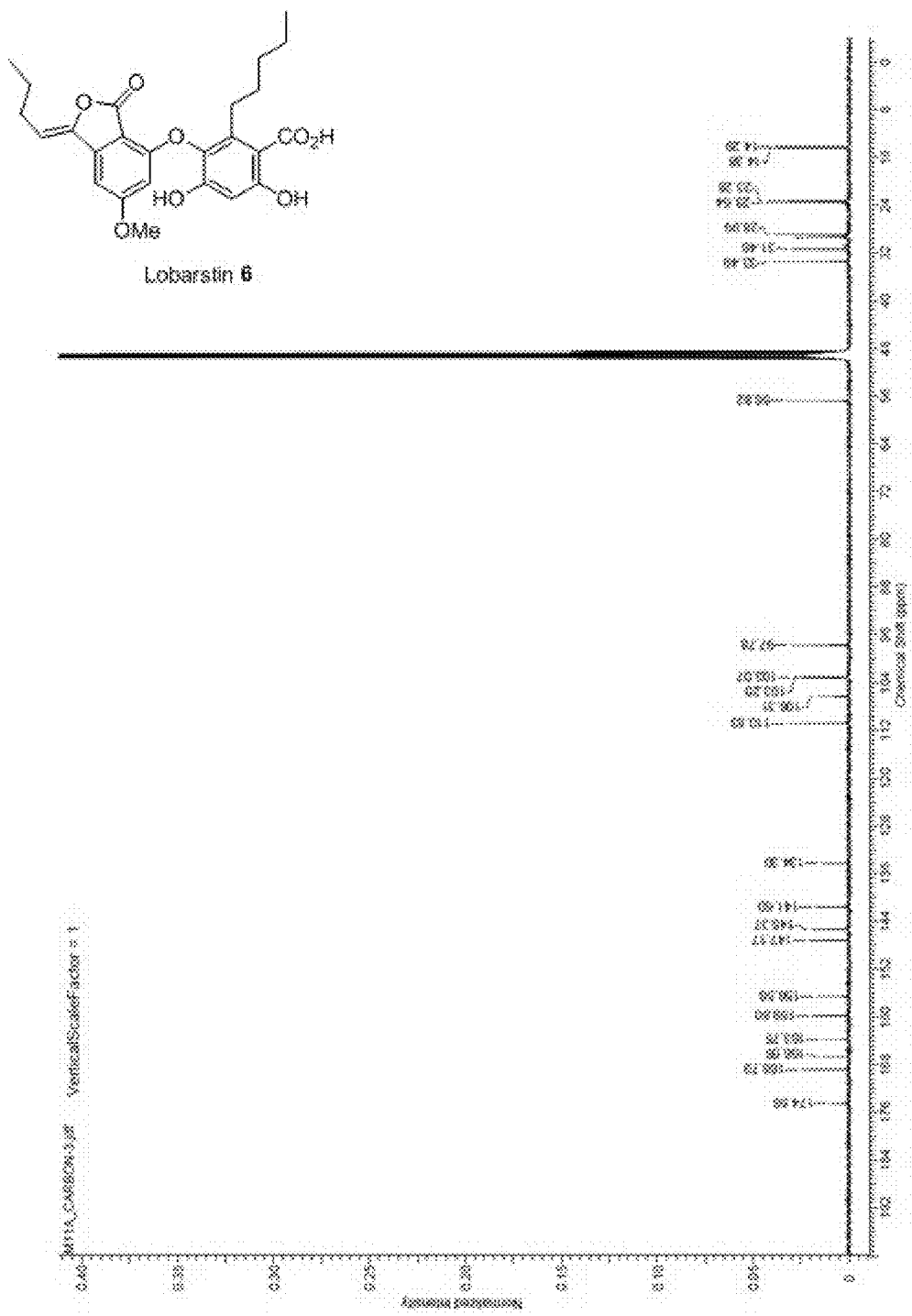
FIG. 38 is the 101 MHz $^{13}$C-NMR spectrum (in CD$_3$OD) of lobastin (Formula 4) according to one example of the present invention.
Figure 39:
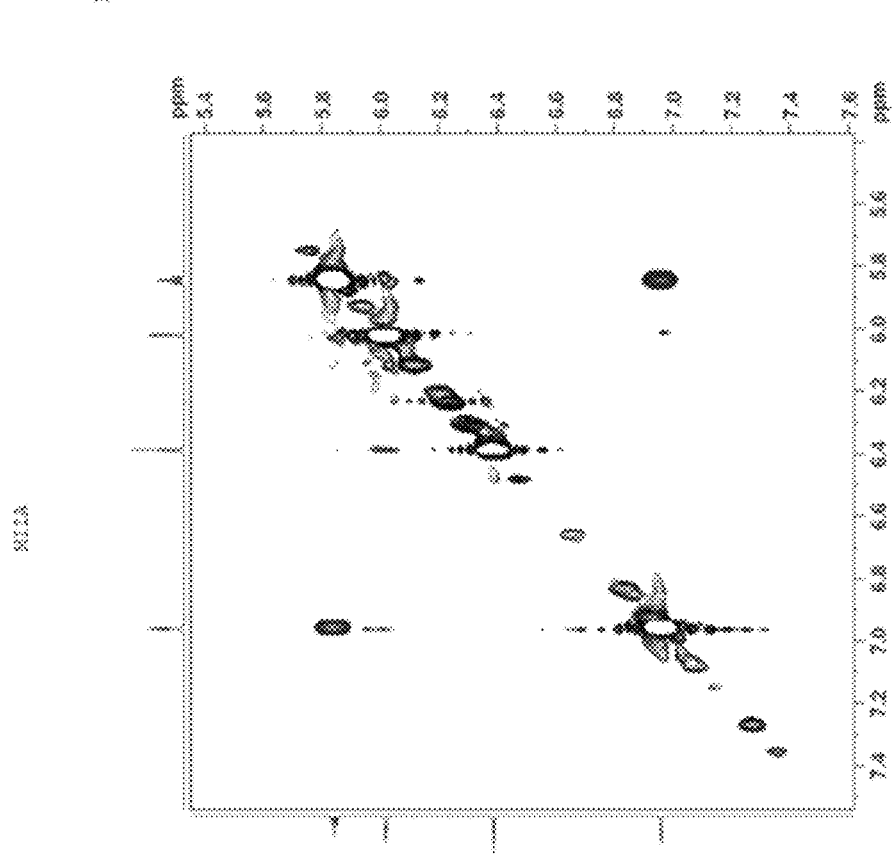
FIG. 39 is the NOESY spectrum (in CD$_3$OD) of lobastin (Formula 4) according to one example of the present invention.

FIGS. 37, 38 and 39 show the 400 MHz $^1$H-NMR spectrum (in CD$_3$OD), 101 MHz $^{13}$C-NMR spectrum (in CD$_3$OD) and NOESY spectrum (in CD$_3$OD) of lobastin (Formula 4), respectively.

$^1$H NMR (400 MHz, CD$_3$OD) δ=6.94 (d, 1H), 6.37 (s, 1H), 6.01 (d, J=1.2, 1H), 5.81 (t, J=7.9, 1H), 3.79 (s, 3H), 2.92 (m, 2H), 2.41 (dd, J=7.9, 7.3, 2H), 1.57 (dq, J=14.6, 7.3, 2H), 1.96 (m, 4H), 1.01 (t, J=7.3, 3H), 0.75 (t, J=7.3, 3H); $^{13}$C NMR (101 MHz, CD$_3$OD) δ=174.6, 168.8, 166.7, 163.7, 159.8, 156.6, 147.2, 145.4, 141.6, 134.3, 110.8, 106.3, 103.2, 103.0, 97.8, 56.8, 33.5, 34.5, 29.4, 29.0, 23.6, 23.3, 14.4, 14.3; HRMS (ESI-TOF) m/z calculated for C$_{25}$H$_{29}$O$_8$ [M+H]$^+$: 457.1862, found: 457.1853.

Example 4

Synthesis of Compound of Formula 5

Example 4-1

Synthesis of 2,4-Dihydroxyl-6-Pentylbenzaldehyde (18)

[Formula 18]

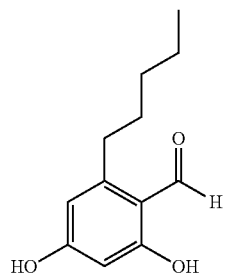

18

The starting material olivetol (19) (5 g, 27.7 mmol) was dissolved in 150 ml of DMF in a round-bottom flask. The solution was cooled to 0° C., and POCl$_3$ (3.9 ml, 41.6 mmol) was added slowly thereto over about 5 minutes. After stirring at 0° C. for 30 minutes, the mixture was warmed to room temperature and stirred for 8 hours. The reaction was terminated by addition of water, and the reaction mixture was extracted about 4 times with MC. The obtained organic layer was dried with Na$_2$SO$_4$, concentrated, and then purified by silica gel chromatography. The yield was 90%.

FIG. 19 shows the 400 MHz $^1$H-NMR spectrum (in CD$_3$OD) of the compound of Formula 18, and FIG. 20 shows the 101 MHz $^{13}$C-NMR spectrum (in CD$_3$OD) of the compound of Formula 18.

$^1$H NMR (400 MHz, CD$_3$OD) δ=10.02 (s, 1H), 6.21 (s, 1H), 6.10 (d, J=2.4, 1H), 2.81 (t, J=7.3, 2H), 1.60 (m, 2H), 1.35 (m, 4H), 0.90 (t, J=6.7, 3H); $^{13}$C NMR (101 MHz, CD$_3$OD) δ=194.2, 167.8, 167.2, 151.5, 113.2, 111.2, 101.7, 33.7, 32.9, 32.8, 23.7, 14.5; HRMS (ESI-TOF) m/z calculated for C$_{12}$H$_{17}$O$_3$ [M+H]$^+$: 209.1178, found: 209.1175.

Example 4-2

Synthesis of 2,4-Bis(Benzyloxy)-6-Pentylbenzaldehyde (20)

[Formula 20]

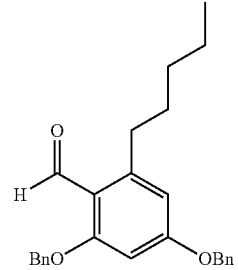

20

In a round-bottom flask, 2,4-dihydroxyl-6-pentylbenzaldehyde (18) (10 g, 48.0 mmol) was dissolved in DMF (50 ml). Benzyl bromide (7.6 ml, 64.3 mmol) and potassium carbonate (8.9 g, 64.3 mmol) were added to the solution, followed by stirring at room temperature for about 12 hours. The reaction solution was separated into layers by addition of ethyl acetate and 1N HCl, and the aqueous layer was additionally extracted three times with ethyl acetate. The obtained organic layer was dried with Na$_2$SO$_4$, concentrated, and then purified by silica gel chromatography. The yield was 98%.

Figure 23:
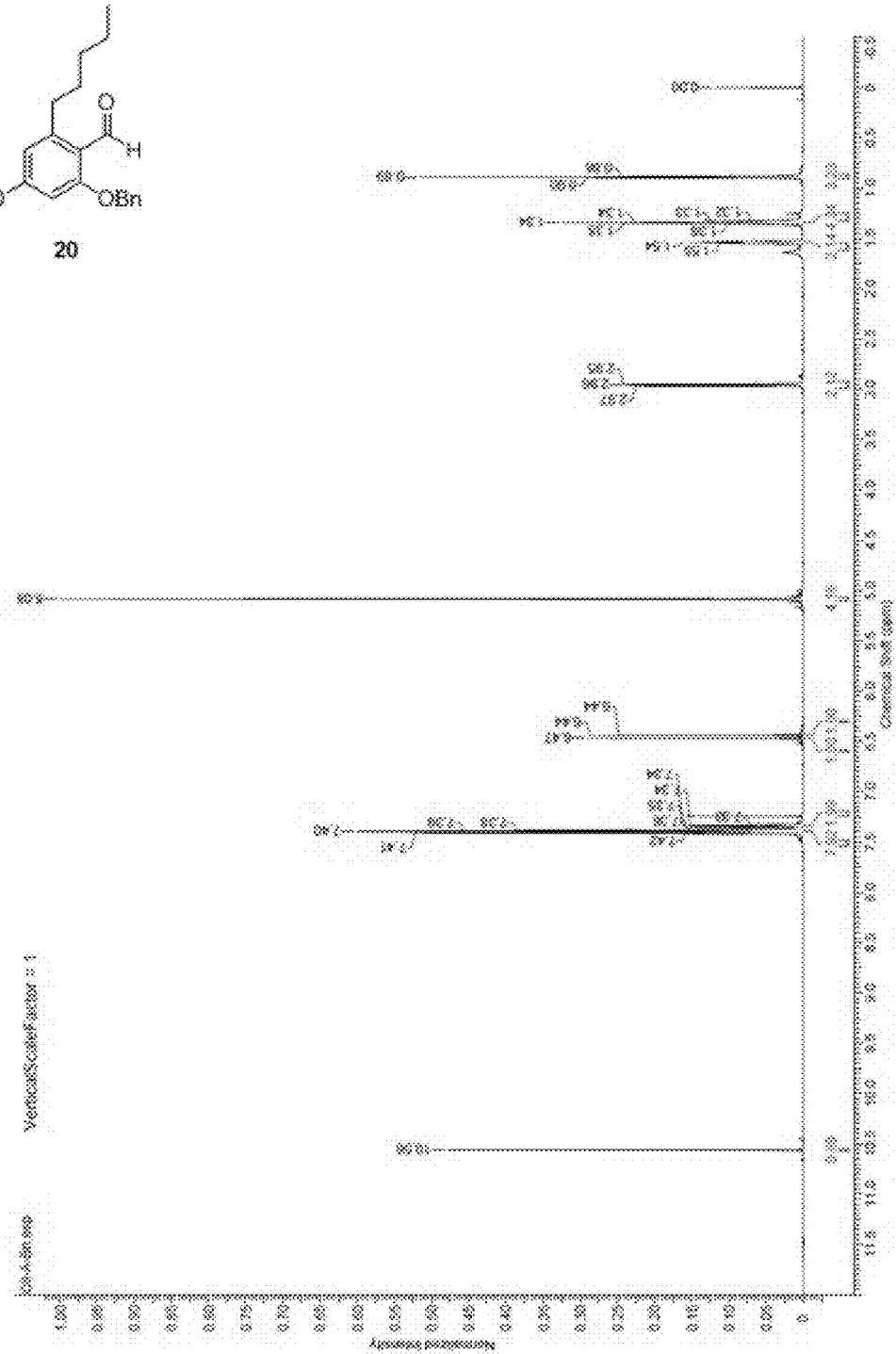
FIG. 23 is the 400 MHz $^1$H-NMR spectrum (in CD$_3$OD) of a compound of Formula 20 according to one example of the present invention.
Figure 24:
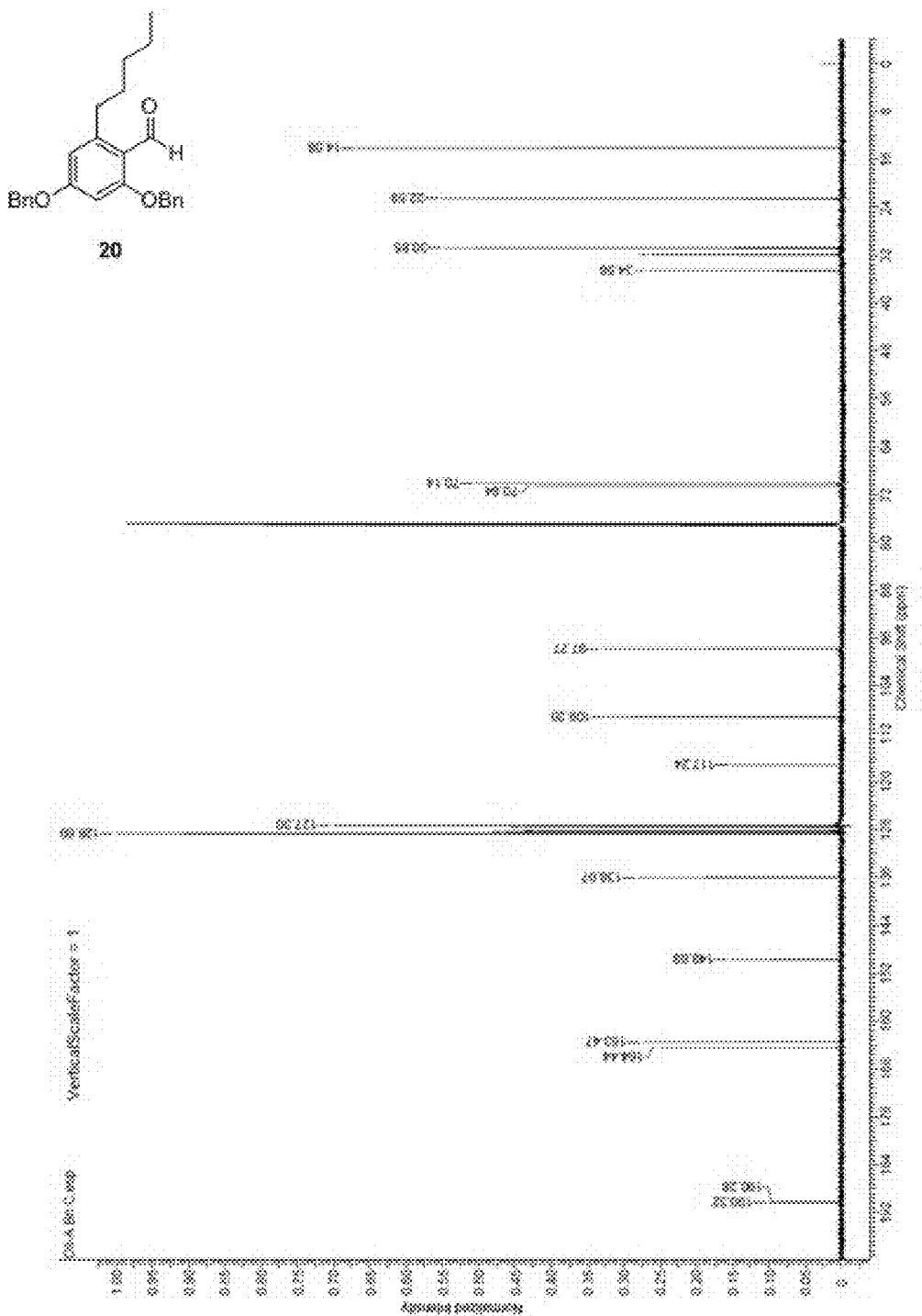
FIG. 24 is the 101 MHz $^{13}$C-NMR spectrum (in CD$_3$OD) of a compound of Formula 20 according to one example of the present invention.

FIG. 23 shows the 400 MHz $^1$H-NMR spectrum (in CD$_3$OD) of the compound of Formula 20, and FIG. 24 shows the 101 MHz $^{13}$C-NMR spectrum (in CD$_3$OD) of the compound of Formula 20.

$^1$H NMR (850 MHz, CDCl$_3$) δ=10.56 (s, 1H), 7.35 (m, 10H), 6.47 (d, J=2.2, 1H), 6.43 (d, J=2.2, 1H), 5.08 (s, 2H), 5.07 (s, 2H) 2.96, (t, J=8.5, 2H), 1.54 (m, 2H), 1.34 (m, 4H), 0.88 (t, J=7.0, 3H); $^{13}$C NMR (214 MHz, CDCl$_3$) δ=190.3, 164.4, 163.5, 149.7, 136.6, 128.7, 128.6, 128.3, 128.2, 127.5, 127.3, 117.2, 109.2, 97.8, 70.6, 70.1, 34.5, 31.9, 30.8, 22.6, 14.1; HRMS (ESI-TOF) m/z calculated for C$_{26}$H$_{29}$O$_3$ [M+H]$^+$: 389.2116, found: 389.2130.

Example 4-3

Synthesis of 2,4-Bis(Benzyloxy)-6-Pentylphenol (21)

[Formula 21]

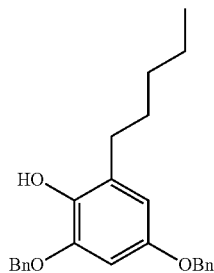

To a dried round-bottom flask, 2,4-bis(benzyloxy)-6-pentylbenzaldehyde (20) (7.4 g, 19.6 mmol) and 100 ml of MC were added. 8.5 g (49 mmol) of mCPBA was precipitated in the mixture at a temperature lower than 10° C. with rapid stirring. The mixture was stirred at room temperature for 4 hours. TLC monitoring was performed. The mixture was extracted and washed three times with concentrated NaHCO$_3$. The organic layer was dried in vacuo, and the crude oil was dissolved again in 100 ml of MeOH. At 0° C., the MeOH mixture was precipitated in 125 ml of 10% KOH solution. The mixture was stirred at 0° C. for 2 hours. MeOH was removed using HCl in a rotary evaporator. The residue was diluted with ethyl acetate. The mixture was separated into two layers, and the aqueous phase was extracted three times with ethyl acetate. The obtained organic layer was dried with anhydrous Na$_2$SO$_4$, concentrated, and then purified by silica gel column chromatography.

Figure 25:
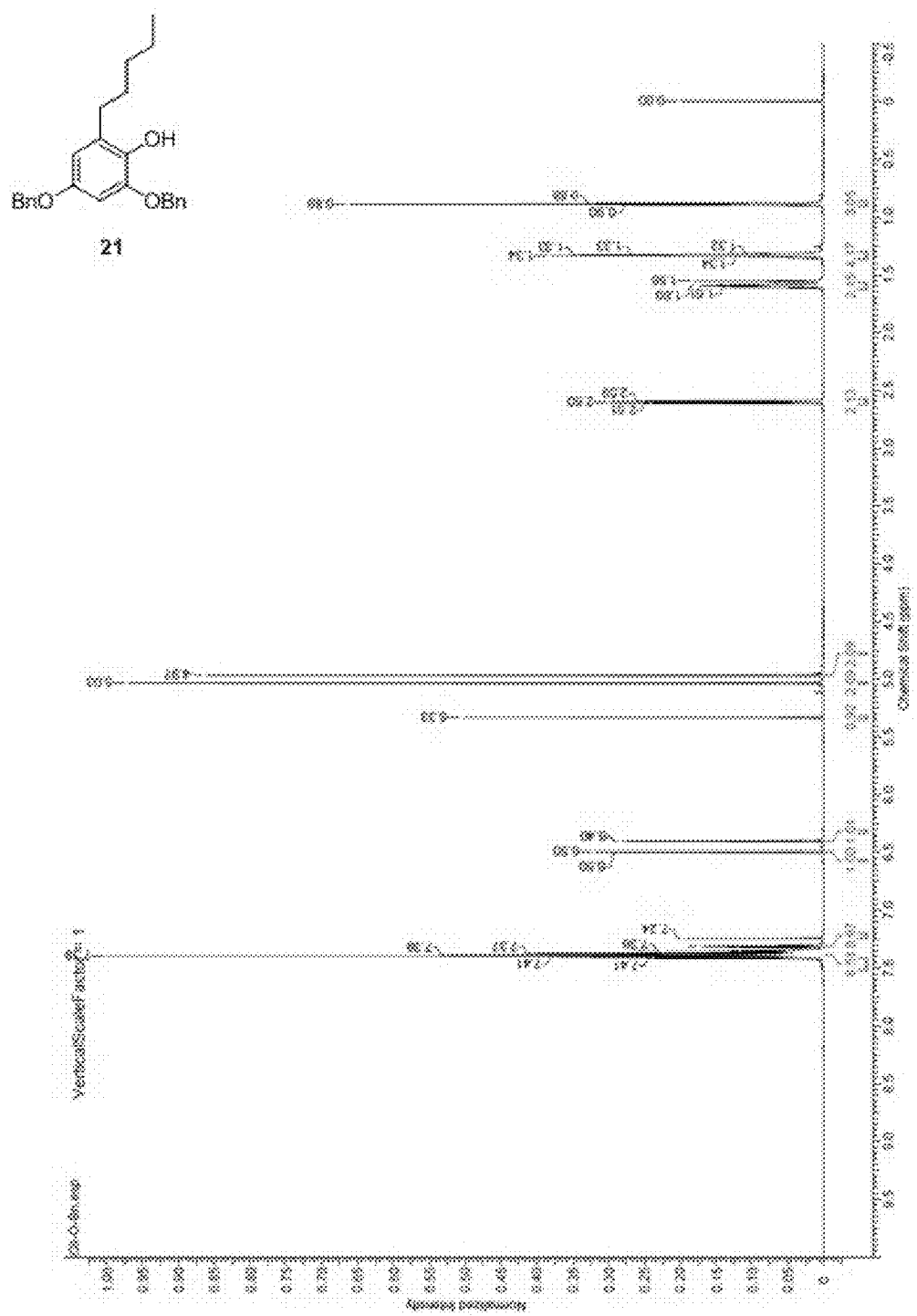
FIG. 25 is the 400 MHz $^1$H-NMR spectrum (in CD$_3$OD) of a compound of Formula 21 according to one example of the present invention.
Figure 26:
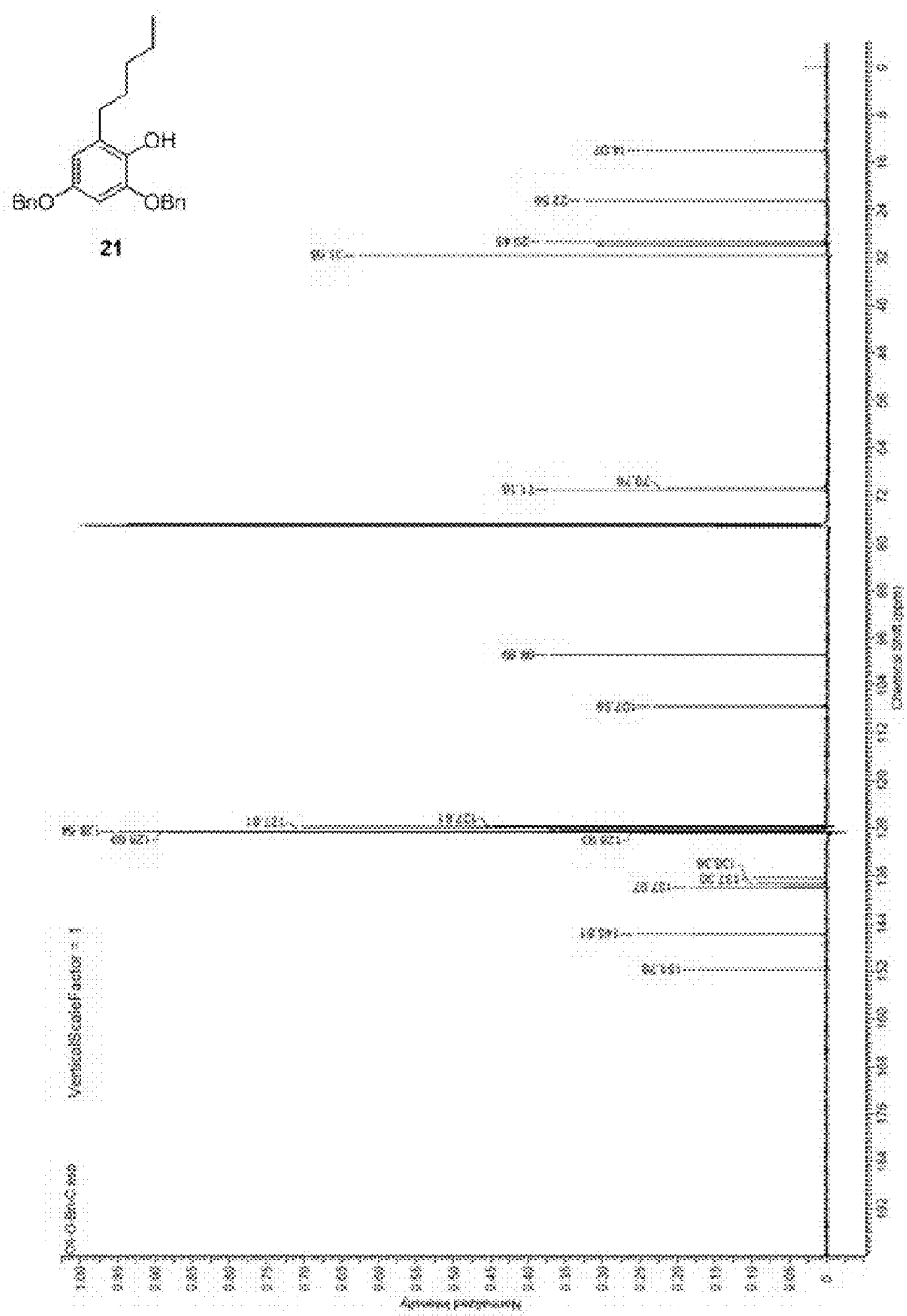
FIG. 26 is the 101 MHz $^{13}$C-NMR spectrum (in CD$_3$OD) of a compound of Formula 21 according to one example of the present invention.

FIG. 25 shows the 400 MHz $^1$H-NMR spectrum (in CD$_3$OD) of the compound of Formula 21, and FIG. 26 shows the 101 MHz $^{13}$C-NMR spectrum (in CD$_3$OD) of the compound of Formula 21.

$^1$H NMR (850 MHz, CDCl$_3$) δ=7.34 (m, 10H), 6.49 (d, J=2.7, 1H), 6.40 (d, J=2.7, 1H) 5.33 (s, 1H), 5.03 (s, 2H), 4.97 (s, 2H), 2.60 (t, J=7.7, 2H), 1.60 (m, 2H), 1.33 (m, 4H), 0.89 (t, J=6.9, 3H); $^{13}$C NMR (214 MHz, CDCl$_3$) δ=151.8, 145.8, 137.9, 137.3, 136.3, 128.9, 128.6, 128.5, 128.3, 127.9, 127.8, 127.6, 107.6, 89.9, 71.2, 70.8, 31.7, 30.0, 29.4, 22.6, 14.1; HRMS (ESI-TOF) m/z calculated for C$_{25}$H$_{29}$O$_3$ [M+H]$^+$: 377.2116, found: 377.2131.

Example 4-4

Synthesis of 7-(2,4-Bis(Benzyloxy)-6-Pentylphenoxy)-3-Butyl-3-Hydroxy-5-Methoxyisobenzofuran-1(3H)-One (24)

[Formula 24]

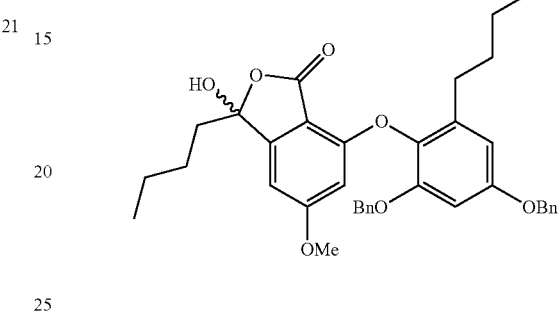

CuI (53 mg, 0.28 mmol), picolinic acid (53 mg, 0.55 mmol), 2-iodo-4-methoxy-6-pentanoylbenzoic acid (10) (500 mg, 1.38 mmol), 2,4-bis(benzyloxy)-6-pentylbenzaldehyde (19) (520 mg, 1.38 mmol) and K$_3$PO$_4$ (880 mg, 4.14 mmol) were added to a dried sealed tube while stirring with a magnetic bar. The tube was evacuated and filled again with argon. Evacuation and filling was repeated two more times. Under a counter flow of argon, 20 ml of DMSO was introduced by a syringe. The tube was left to stand in an oil bath preheated to 110° C. and the reaction mixture was stirred vigorously for 12 hours. The reaction mixture was cooled to room temperature. After addition of ethyl acetate and H$_2$O, the mixture was stirred. The organic layer was separated and the aqueous layer was extracted twice with ethyl acetate. The organic layer was dried with Na$_2$SO$_4$ and filtered through a silica gel pad. The filtrate was concentrated, and the resulting residue was purified by silica gel chromatography. The yield was 63%.

Figure 40:
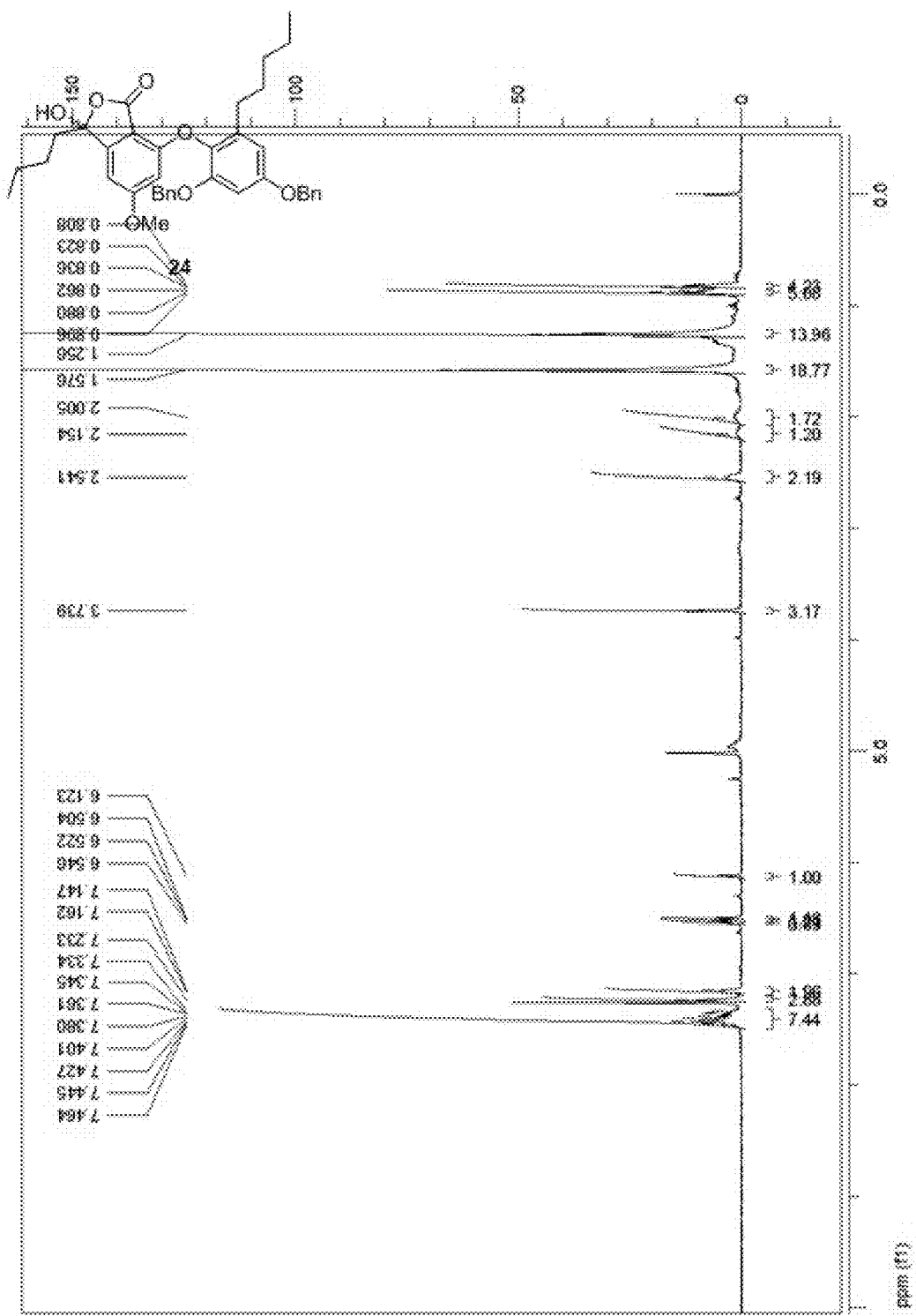
FIG. 40 is the 400 MHz $^1$H-NMR spectrum (in CD$_3$OD) of a compound of Formula 24 according to one example of the present invention.
Figure 41:
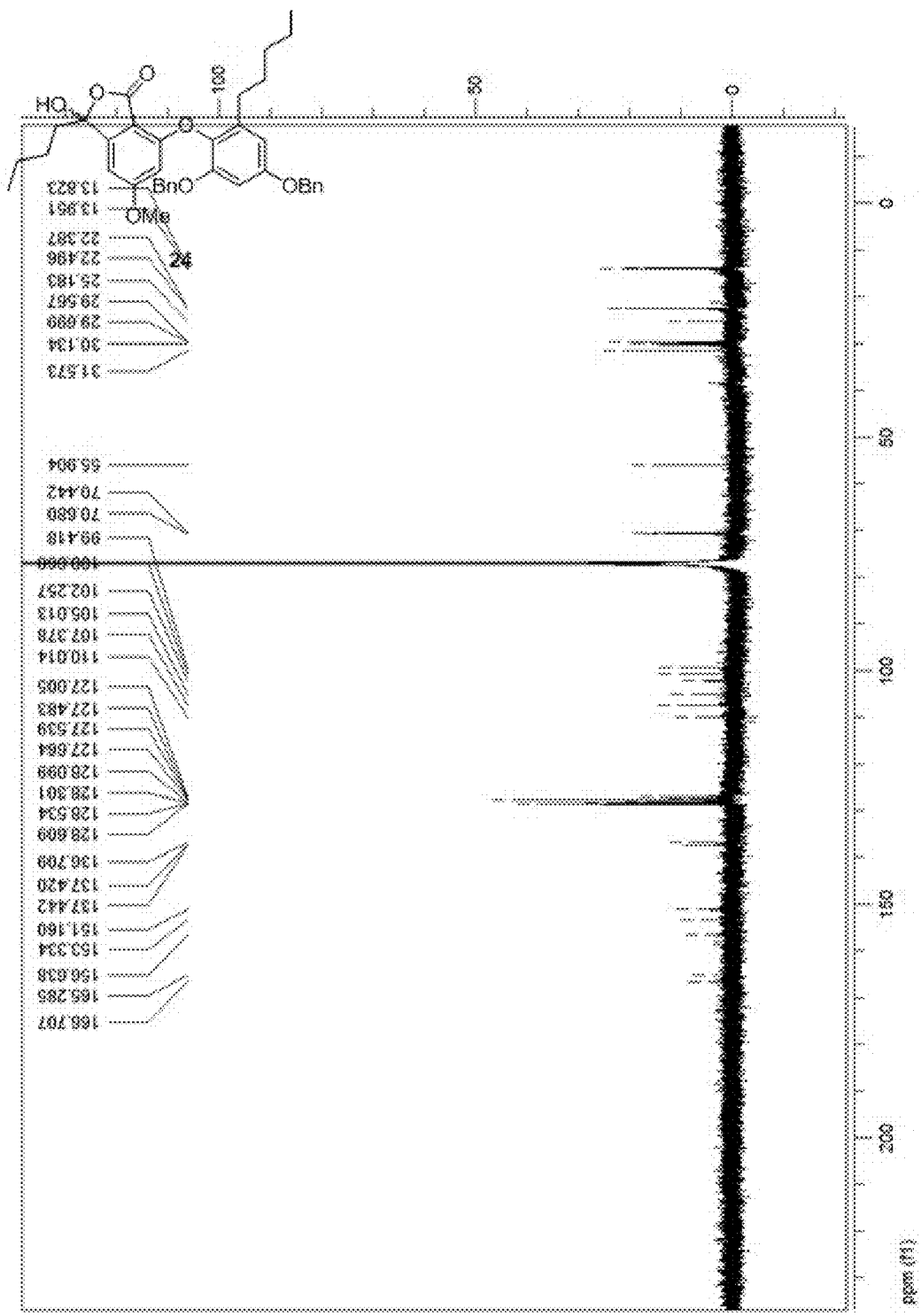
FIG. 41 is the 101 MHz $^{13}$C-NMR spectrum (in CD$_3$OD) of a compound of Formula 24 according to one example of the present invention.

FIG. 40 shows the 400 MHz $^1$H-NMR spectrum (in CD$_3$OD) of the compound of Formula 24, and FIG. 41 shows the 101 MHz $^{13}$C-NMR spectrum (in CD$_3$OD) of the compound of Formula 24.

$^1$H NMR (400 MHz, CDCl$_3$) δ=7.34 (m, 10H), 6.55 (s, 1H), 6.52 (s, 1H) 6.50 (s, 1H), 6.12 (s, 1H), 5.02 (s, 2H), 4.96 (s, 2H), 3.74 (s, 3H), 2.52 (m, 2H), 2.06 (m, 2H), 1.58 (m, 4H), 1.26 (m, 6H), 0.88 (m, 3H), 0.82 (m, 3H); $^{13}$C NMR (101 MHz, CDCl$_3$) δ=166.6, 165.3, 156.6, 153.3, 151.1, 137.4, 136.7, 128.6, 128.5, 128.3, 128.1, 127.8, 127.6, 127.5, 127.4, 127.0, 110.0, 107.4, 104.5, 102.2, 100.6, 99.4, 70.6, 70.4, 55.9, 31.6, 30.1, 29.7, 29.5, 25.1, 22.5, 22.4, 13.9, 13.8; HRMS (ESI-TOF) m/z calculated for C$_{38}$H$_{43}$O$_7$ [M+H]$^+$: 611.3009, found: 611.3009.

Example 4-5

Synthesis of Sakisacaulon A (5)

[Formula 5]

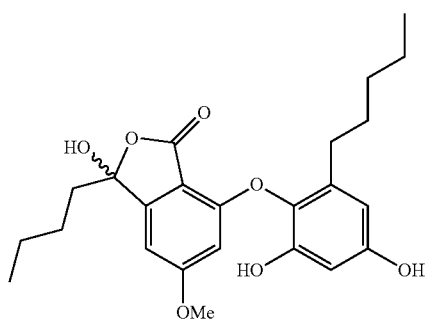

Palladium (10%, 10 mg) on carbon was added to a round-bottom flask filled with 7-(2,4-bis(benzyloxy)-6-pentylphenoxy)-3-butyl-3-hydroxy-5-methoxyisobenzofuran-1 (3H)-one) (23) (100 mg, 0.164 mmol) in 20 ml of MeOH. Under a hydrogen atmosphere, the mixture was stirred for 12 hours. The reaction mixture was filtered through a silica gel pad. The solvent was removed by concentration under reduced pressure, and the crude mixture was purified by C18 chromatography. The yield was 88%.

Figure 42:
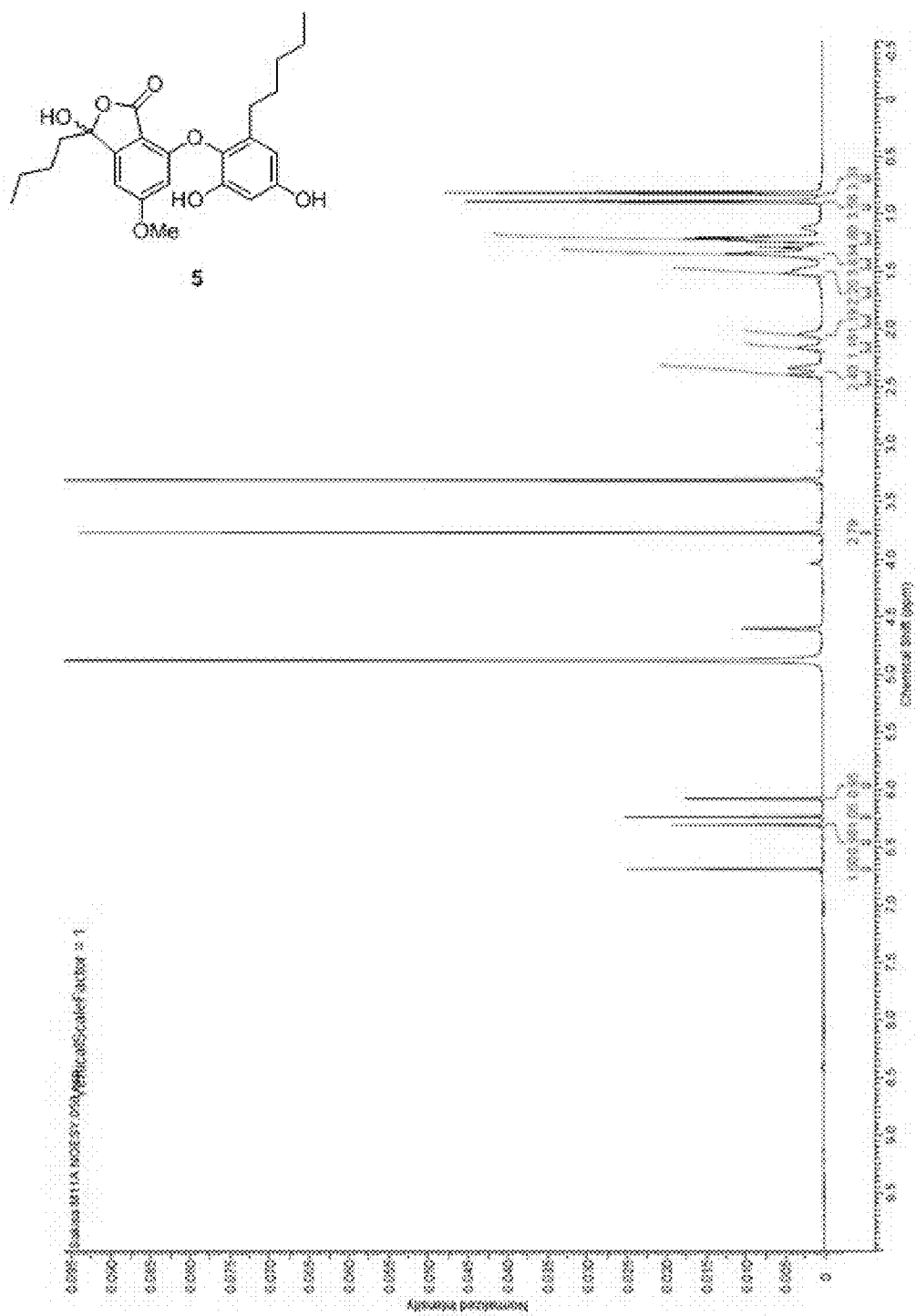
FIG. 42 is the 850 MHz $^1$H-NMR (in CD$_3$OD) spectrum of sakisacaulon A (Formula 5) according to one example of the present invention.
Figure 43:
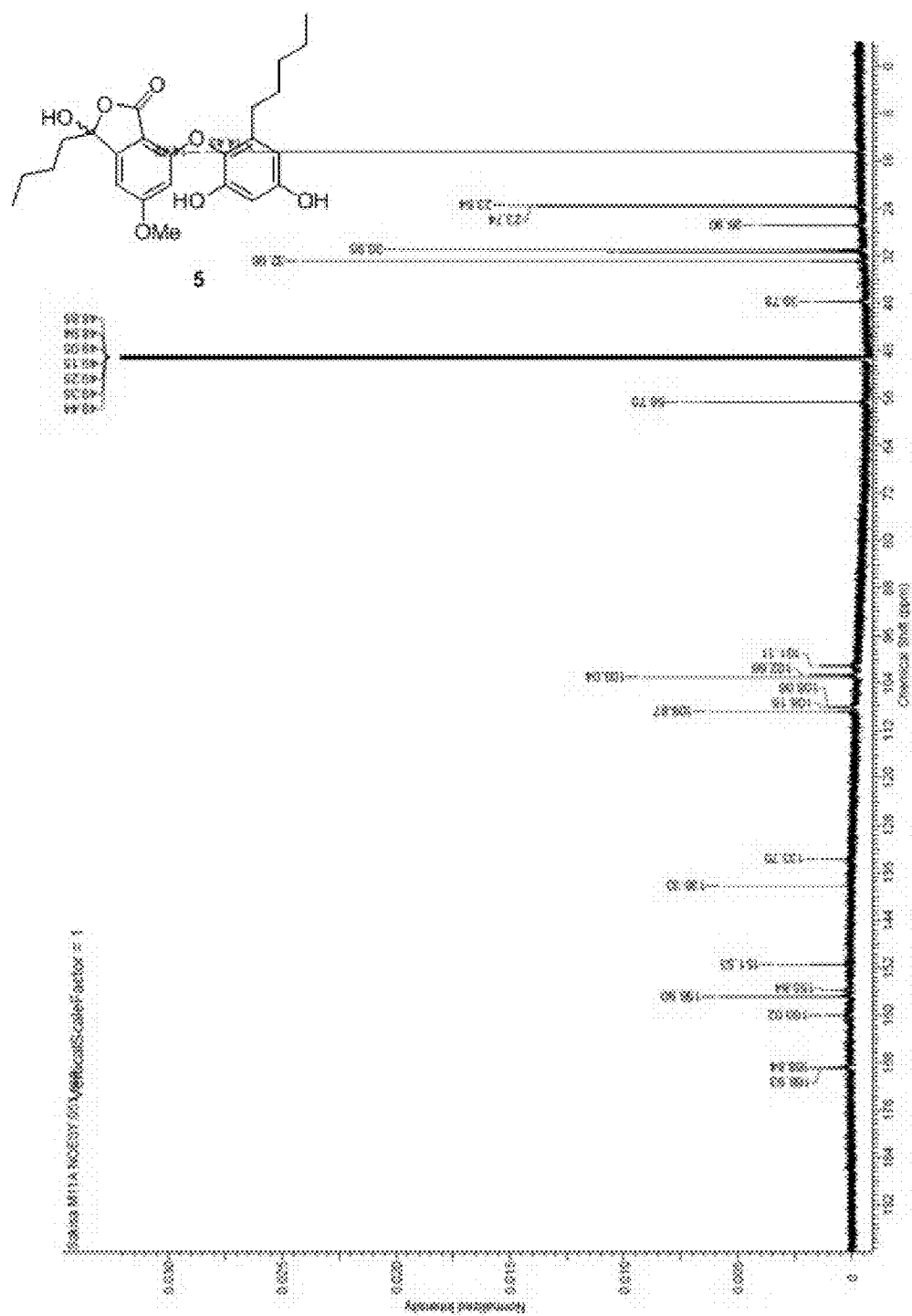
FIG. 43 is the 214 MHz $^{13}$C-NMR spectrum (in CD$_3$OD) of sakisacaulon A (Formula 5) according to one example of the present invention.

FIG. 42 shows the 850 MHz $^1$H-NMR (in $CD_3OD$) spectrum of sakisacaulon A (Formula 5), and FIG. 43 shows the 214 MHz $^{13}$C-NMR spectrum (in $CD_3OD$) of sakisacaulon A (Formula 5).

$^1$H NMR (850 MHz, $CD_3OD$) δ=6.69 (d, 1H), 6.31 (d, J=2.6, 1H), 6.23 (d, J=2.8, 1H), 6.08 (s, 1H), 3.77 (s, 3H), 2.40-2.33 (m, 2H), 2.16-2.04 (m, 2H), 1.52 (m, 2H), 1.34 (m, 4H), 1.21 (m, 4H), 0.89 (t, J=7.1, 3H), 0.82 (t, J=6.9, 3H); $^{13}$C NMR (214 MHz, $CD_3OD$) δ=168.9, 168.8, 106.0, 156.9, 155.8, 151.5, 138.3, 133.7, 108.9, 108.2, 108.1, 103.0, 102.7, 101.1, 56.7, 39.8, 32.9, 31.4, 31.0, 26.9, 23.7, 23.5, 14.5, 14.4; HRMS (ESI-TOF) m/z calculated for $C_{24}H_{31}O_7$ [M+H]$^+$: 431.2070, found: 431.2060.

INDUSTRIAL APPLICABILITY

The synthesis method according to the present invention can synthesize compounds that selectively inhibit PTP1B in a simple and economic manner, in which the compounds are five phenolic lichen metabolites isolated from an extract of the Antarctic lichen *Stereocaulon alpinum*.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

The invention claimed is:

1. A method of preparing a lobaric acid analogue of Formula 3 or 5, comprising subjecting a compound of Formula 10 to a coupling reaction with a compound of Formula 16 or 21, followed by a deprotection reaction:

[Formula 10]

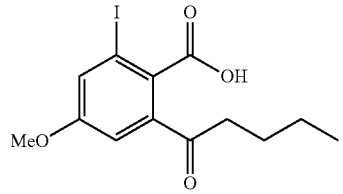

[Formula 16]

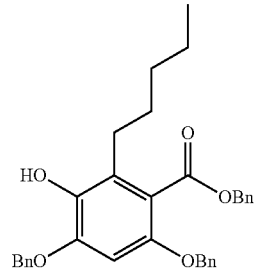

[Formula 21]

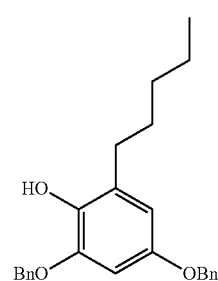

[Formula 3]

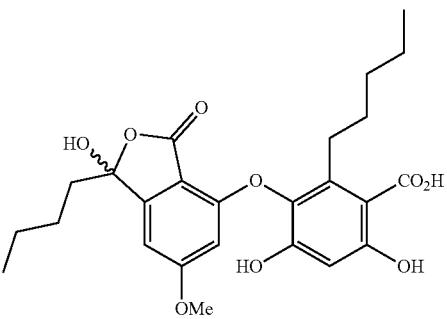

[Formula 5]

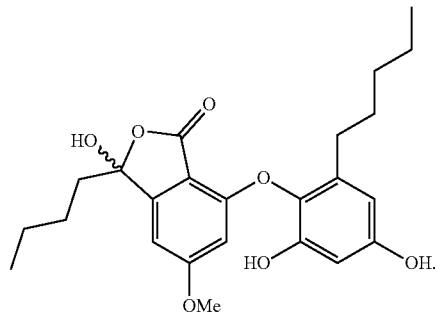

2. The method of claim 1, wherein the compound of Formula 10 is produced by a method comprising:

(a) obtaining a compound of Formula 7 by subjecting 4-halogen phthalic anhydride to Ullmann coupling and ring-opening reactions by adding a metal methoxide;
(b) obtaining a compound of Formula 8 by reacting the compound of Formula 7 with acetic anhydride;
(c) obtaining a compound of Formula 9 by subjecting a methyl ester moiety of the compound of Formula 8 to a Grignard reaction in a solvent; and
(d) obtaining the compound of Formula 10 by subjecting the compound of Formula 9 to ortho-iodination by adding an iodoacetate cation-containing compound:

[Formula 7]

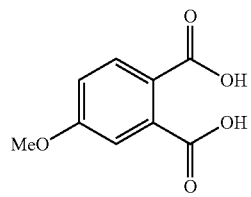

7

[Formula 8]

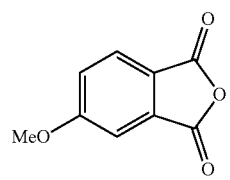

8

[Formula 9]

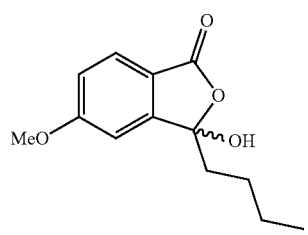

9

[Formula 10]

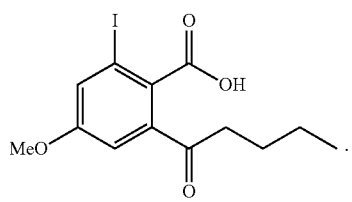

10

3. The method of claim 1, wherein the compound of Formula 16 is produced by a method comprising:
(a) obtaining a compound of Formula 13 by protecting dihydroxy group and carboxylic acid functional group of 2,4-dihydroxybenzoic acid, and then subjecting the 2,4-dihydroxybenzoic acid to ortho-iodination by addition of an iodoacetate cation-containing compound;
(b) obtaining a compound of Formula 14 by alkylating the compound of Formula 13 by addition of pentylboronic acid;
(c) obtaining an aldehyde compound of Formula 15 by formylating the compound of Formula 14 with a phosphorus oxychloride compound in DMF as a solvent; and
(d) obtaining the compound of Formula 16 by reacting the compound of Formula 15 with chloroperoxybenzoic acid in a solvent:

[Formula 13]

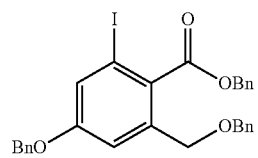

13

[Formula 14]

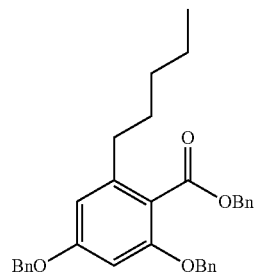

14

[Formula 15]

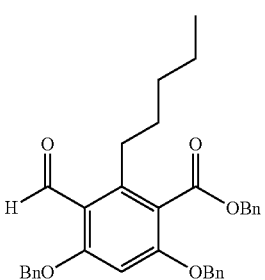

15

[Formula 16]

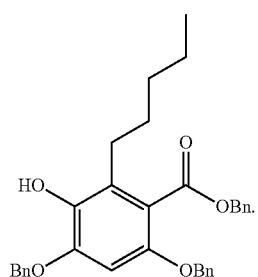

16

4. The method of claim 1, wherein the compound of Formula 21 is produced by a method comprising:
(a) obtaining a compound of Formula 20 by protecting the dihydroxy group of benzoic acid of the olivetol compound of Formula 17 in a solvent, followed by formylation with a phosphorus oxychloride compound; and
(b) obtaining the alcohol compound of Formula 21 by reacting the compound of Formula 20 with chloroperoxybenzoic acid in a solvent:

[Formula 17]

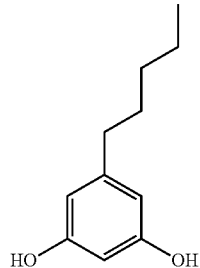

[Formula 20]

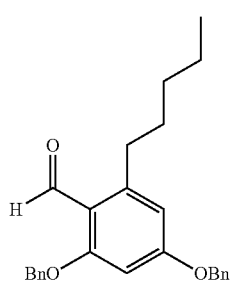

[Formula 21]

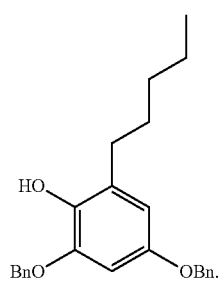

5. A method of preparing lobaric acid, comprising protecting a carboxylic acid of a lobaric acid analogue of Formula 3 to obtain a compound of Formula 23, and then relactonizing the compound of Formula 23 in a solvent to obtain lobaric acid of Formula 1:

[Formula 1]

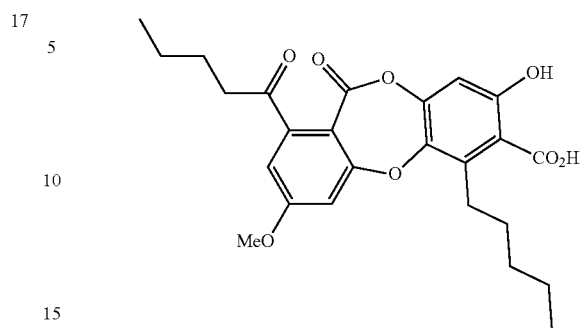

[Formula 23]

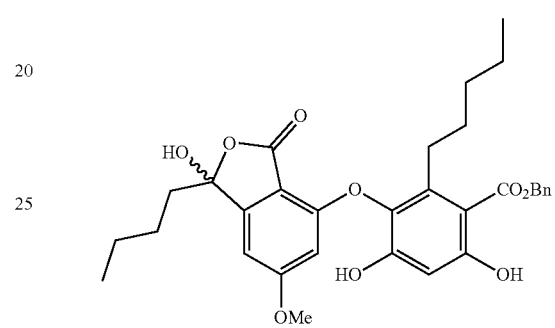

[Formula 3]

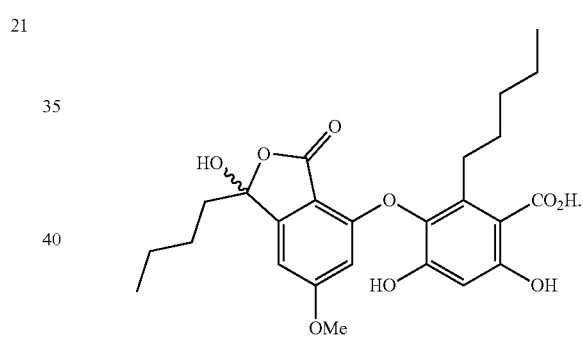

6. The method of preparing lobaric acid of claim 5, wherein the solvent is ethylene dichloride (EDC) or 4-dimethylaminopyridine (DMAP).

* * * * *

UNITED STATES PATENT AND TRADEMARK OFFICE
CERTIFICATE OF CORRECTION

PATENT NO. : 11,434,217 B2
APPLICATION NO. : 16/958794
DATED : September 6, 2022
INVENTOR(S) : Joung Han Yim It is certified that error appears in the above-identified patent and that said Letters Patent is hereby corrected as shown below:

In the Specification

Column 15, Line 8, "POC13" should be -- $POCl_3$ --.

Column 16, Line 11, "B rings-2" should be -- B ring-2 --.

Column 29, Line 65, "$NaH_2PO_4$—$H_2O$" should be -- $NaH_2PO_4$-$H_2O$ --.

Column 39, Line 36, "$\delta = 6.69$ (d, 1H)" should be -- $\delta = 6.69$ (d, $J$=1.4, 1H) --.

Signed and Sealed this
First Day of November, 2022

Katherine Kelly Vidal
*Director of the United States Patent and Trademark Office*